United States Patent
Joshi-Hangal et al.

(10) Patent No.: US 10,858,386 B2
(45) Date of Patent: Dec. 8, 2020

(54) DRUG COMPOUND AND PURIFICATION METHODS THEREOF

(71) Applicant: Otsuka Pharmaceutical Co., Ltd., Tokyo (JP)

(72) Inventors: Rajashree Joshi-Hangal, Pleasanton, CA (US); Nipun Davar, Pleasanton, CA (US); Stephen R. Priebe, Pleasanton, CA (US)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 16/674,786

(22) Filed: Nov. 5, 2019

(65) Prior Publication Data

US 2020/0172565 A1    Jun. 4, 2020

Related U.S. Application Data

(63) Continuation of application No. 16/053,354, filed on Aug. 2, 2018, now Pat. No. 10,519,190.

(60) Provisional application No. 62/540,706, filed on Aug. 3, 2017.

(51) Int. Cl.
| | |
|---|---|
| C07H 21/04 | (2006.01) |
| A61K 9/19 | (2006.01) |
| A61K 31/7084 | (2006.01) |
| F26B 5/06 | (2006.01) |
| C07H 19/173 | (2006.01) |
| A61P 35/00 | (2006.01) |

(52) U.S. Cl.
CPC .............. *C07H 21/04* (2013.01); *A61K 9/19* (2013.01); *A61K 31/7084* (2013.01); *C07H 19/173* (2013.01); *F26B 5/06* (2013.01); *A61P 35/00* (2018.01)

(58) Field of Classification Search
None
See application file for complete search history.

(56) References Cited

U.S. PATENT DOCUMENTS

| | | | |
|---|---|---|---|
| 6,905,669 B2 | 6/2005 | Dimartino | |
| 6,982,253 B2 | 1/2006 | Joshi-Hangal et al. | |
| 6,998,391 B2 | 2/2006 | Lyons et al. | |
| 7,135,464 B2 | 11/2006 | Joshi-Hangal et al. | |
| 7,144,873 B2 | 12/2006 | Joshi-Hangal et al. | |
| 7,250,416 B2 | 7/2007 | Phiasivongsa et al. | |
| 7,276,228 B2 | 10/2007 | Dimartino | |
| 7,700,567 B2 | 4/2010 | Phiasivongsa et al. | |
| 8,461,123 B2 | 6/2013 | Phiasivongsa et al. | |
| 9,358,248 B2 | 6/2016 | Phiasivongsa et al. | |
| 9,381,207 B2 | 7/2016 | Joshi-Hangal et al. | |
| 9,480,698 B2 | 11/2016 | Phiasivongsa et al. | |
| 9,913,856 B2 | 3/2018 | Joshi-Hangal et al. | |
| 10,456,415 B2 | 10/2019 | Phiasivongsa et al. | |
| 10,485,764 B2 | 11/2019 | Joshi-Hangal et al. | |
| 10,517,886 B2 | 12/2019 | Joshi-Hangal et al. | |
| 10,519,190 B2 | 12/2019 | Joshi-Hangal et al. | |
| 2002/0114809 A1 | 8/2002 | Rubinfeld et al. | |
| 2003/0147813 A1 | 8/2003 | Lyons | |
| 2004/0052864 A1 | 3/2004 | Rubinfeld et al. | |
| 2004/0109846 A1 | 6/2004 | Rubinfeld et al. | |
| 2004/0162263 A1 | 8/2004 | Sands et al. | |
| 2004/0224919 A1 | 11/2004 | Rubinfeld et al. | |
| 2005/0037992 A1 | 2/2005 | Lyons et al. | |
| 2005/0059682 A1 | 3/2005 | Rubinfeld | |
| 2005/0209186 A1 | 9/2005 | Lyons | |
| 2006/0014949 A1 | 1/2006 | Redkar et al. | |
| 2006/0063735 A1 | 3/2006 | Redkar et al. | |
| 2006/0069060 A1 | 3/2006 | Redkar et al. | |
| 2006/0074046 A1 | 4/2006 | Redkar et al. | |
| 2006/0128653 A1 | 6/2006 | Tang et al. | |
| 2006/0128654 A1 | 6/2006 | Tang et al. | |
| 2006/0140947 A1 | 6/2006 | Lyons et al. | |
| 2006/0205687 A1 | 9/2006 | Phiasivongsa et al. | |
| 2007/0105792 A1 | 5/2007 | Dimartino | |
| 2007/0117776 A1 | 5/2007 | Lyons | |
| 2007/0254835 A1 | 11/2007 | Lyons et al. | |
| 2008/0108559 A1 | 5/2008 | Dimartino | |
| 2010/0062992 A1 | 3/2010 | Redkar et al. | |
| 2016/0015805 A1 | 1/2016 | Azab et al. | |
| 2017/0000738 A1 | 1/2017 | Joshi-Hangal et al. | |

FOREIGN PATENT DOCUMENTS

| | | |
|---|---|---|
| WO | WO-02085400 A1 | 10/2002 |
| WO | WO-03065995 A2 | 8/2003 |
| WO | WO-03103687 A1 | 12/2003 |
| WO | WO-2006063111 A2 | 6/2006 |

(Continued)

OTHER PUBLICATIONS

International search report and written opinion dated Jan. 29, 2019 for PCT Application No. PCT/IB2018/000992.
Notice of Allowance dated Sep. 30, 2019 for U.S. Appl. No. 16/053,354.

*Primary Examiner* — Dale R Miller

(74) *Attorney, Agent, or Firm* — Wilson Sonsini Goodrich & Rosati

(57) ABSTRACT

The invention provides a method of preparing a lyophilized pharmaceutical composition containing a compound described herein or a pharmaceutically-acceptable salt thereof. The process comprises dissolving the compound in a solvent comprising dimethylsulfoxide and optionally one or more co-solvents to form a solution, and then removing the solvent and any co-solvents by a freeze-drying process. Also provided by the invention are lyophilized pharmaceutical compositions and their use in medicine and in particular in the treatment of cancer.

27 Claims, 40 Drawing Sheets

(56) References Cited

FOREIGN PATENT DOCUMENTS

| WO | WO-2006071491 | A1 | 7/2006 |
| WO | WO-2006099132 | A1 | 9/2006 |
| WO | WO-2013033176 | A1 | 3/2013 |
| WO | WO-2019014286 | A3 | 2/2019 |

21A 21B 24A  24B

DRUG COMPOUND AND PURIFICATION METHODS THEREOF

CROSS REFERENCE

This application is a continuation of U.S. patent application Ser. No. 16/053,354 filed Aug. 2, 2018, which claims the benefit of U.S. Provisional Application No. 62/540,706, filed Aug. 3, 2017, each of which is incorporated herein by reference in its entirety.

BACKGROUND

DNA methylation is a post replicative chemical modification of DNA. Different cancers can be stratified by their abnormal DNA methylation profiles (degree of global or specific DNA methylation) and the hypermethylation of specific genes can be associated with the prognosis for gastric, lung, esophageal, pancreatic, and colon cancer. DNA methylation patterns can also be used to predict response or resistance to therapy in glioma and melanoma. Azacitidine and decitabine are two FDA approved hypomethylating agents (HMAs) that exert their therapeutic effect by inhibiting DNA methylation levels.

Lyophilization, often referred to as freeze drying, is a method of dehydration in which a solvent-containing substrate is frozen and then subjected to a vacuum so that the solvent is removed by sublimation, i.e. direct conversion from the solid frozen state into the gaseous state.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, the invention provides a composition comprising:

a) a compound of the formula:

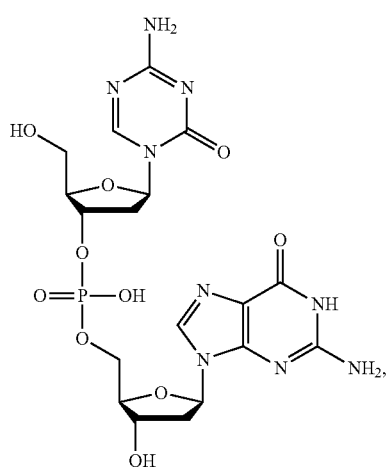

Formula (1)

or a pharmaceutically acceptable salt thereof, wherein the composition comprises at least 95% of the compound; and b) a nucleotide-based compound that is not a compound of Formula (1).

DETAILED DESCRIPTION

Figure 1:
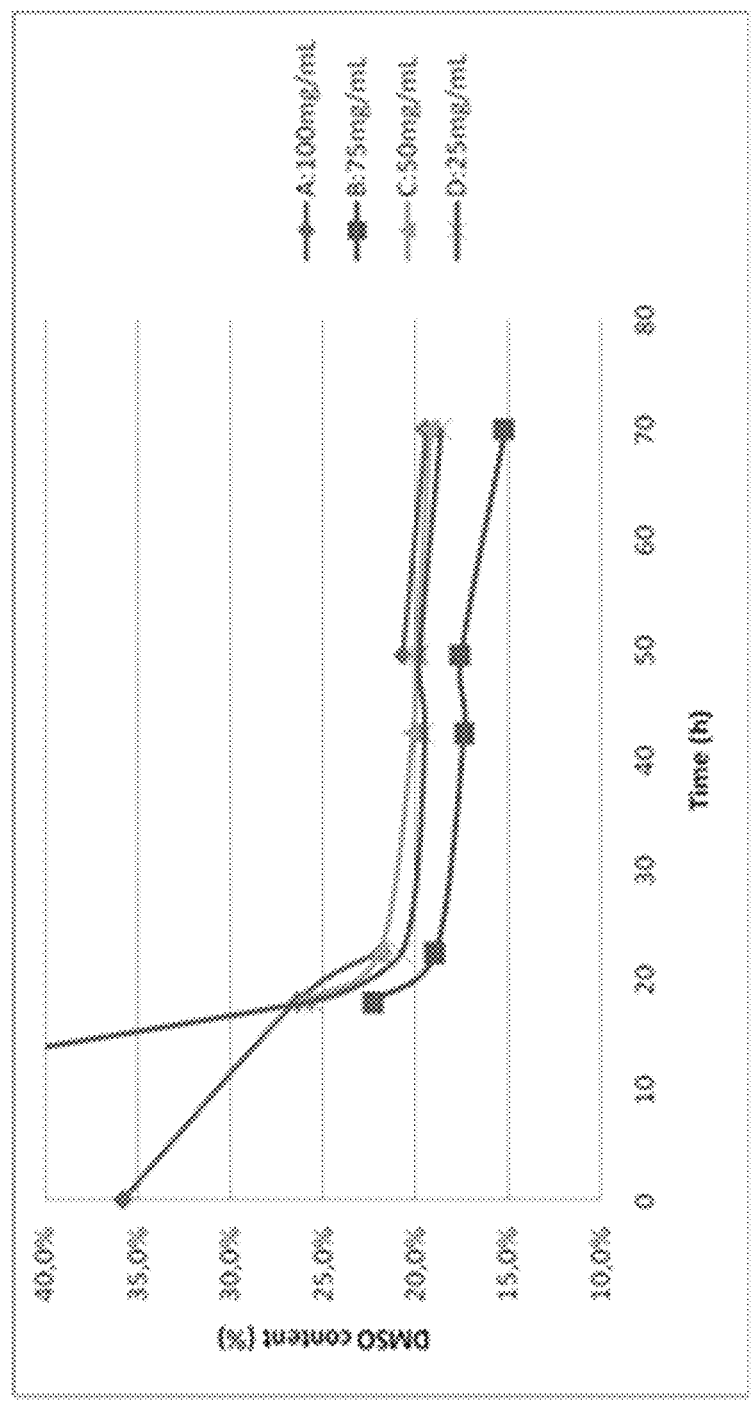
FIG. 1 is a plot of dimethyl sulfoxide (DMSO) removal with time as the lyophilization process described herein progresses. DMSO removal profiles for four formulations A, B, C, and D of different concentrations are shown in FIG. 1.

This application relates to lyophilized pharmaceutical compositions containing a dinucleotide derived from decitabine, and to methods for the preparation and use of decitabine-derived dinucleotide compositions.

The present disclosure relates to improved lyophilized compositions containing a compound of formula (1) or a pharmaceutically acceptable salt thereof, and to a method of preparing the improved lyophilized pharmaceutical compositions using a freeze drying process. The present disclosure also provides the use of the lyophilized pharmaceutical compositions in medicine, and, in particular, the use of the lyophilized pharmaceutical compositions in the treatment of cancers.

The present disclosure provides methods for lyophilization of a substrate comprising a non-aqueous solvent, for example, DMSO and a compound of formula (1), or a pharmaceutically-acceptable salt thereof. Generally, the methods involve two freezing stages with an intermediate warming stage (annealing stage) between the two freezing stages. The methods can be used for removal of the non-aqueous solvent from the substrate. In some embodiments, the compound within the substrate is a compound of formula (1):

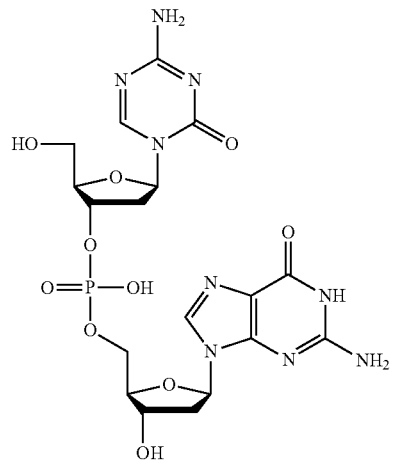

or a pharmaceutically acceptable salt thereof. The present disclosure also provides lyophilized compositions comprising a compound of formula (1) or a pharmaceutically acceptable salt thereof. In addition, the present disclosure provides uses of the lyophilized pharmaceutical compositions in medicine, particularly in the treatment of cancers.

By using two freezing stages and an intermediate warming stage (annealing stage) between the two freezing stages, DMSO can be removed much more quickly during the subsequent primary drying stage and that, consequently, the length of the secondary drying stage can be significantly reduced. The intermediate warming stage can provide increased porosity, thereby allowing the DMSO to sublime more readily. Thus, much more of the DMSO can be removed during the primary drying stage.

Freeze Drying Microscopy (FDM) studies on the formulations have shown that, even at temperatures below −30° C., on occasion, there can be some residual non-frozen solvent or co-solvent present. The term "frozen" as used herein therefore includes a state in which there is present a solid structure formed from solvent and/or co-solvent molecules but there can also be present some solvent and/or co-solvent in non-frozen, or liquid, form.

Method for Preparing Lyophilized Pharmaceutical Composition.

The methods provided herein include a method of preparing a lyophilized pharmaceutical composition containing a compound, for example, a compound of formula (1)) or a pharmaceutically-acceptable salt thereof, which method involves dissolving the compound of formula (1) or the pharmaceutically acceptable salt thereof in a non-aqueous solvent, which can contain DMSO, and optionally one or more co-solvents to form a solution, and then removing the solvent and any co-solvents by a freeze-drying process to give a lyophilized product; wherein the freeze-drying process can involve one or more of the following stages: (i) a first freezing stage in which the solution is frozen by reducing the temperature thereof to a temperature of no greater than −20° C.; (ii) a first warming stage in which the temperature of the frozen solution is raised to a temperature in the range from −15° C. to 5° C. at which the solution remains in a frozen state; (iii) a second freezing stage, which occurs after the first warming stage and in which the temperature of the solution in its frozen state is lowered to a temperature of no greater than −20° C.; (iv) a primary drying stage comprising a sublimation step in which DMSO and one or more co-solvents when present are removed by sublimation from the solution in the frozen state under reduced pressure to give a partially dried product; and (v) a secondary drying stage in which DMSO and one or more co-solvents when present are removed by evaporation from the partially dried product in a non-frozen state under reduced pressure to give the lyophilized product.

The sequence of freezing and intermediate warming stages (i), (ii), and (iii) can be repeated one or more times before proceeding to the primary drying stage (iv). For example, a first sequence of stages (i), (ii), and (iii) can be followed by a second sequence of stages (i), (ii), and (iii), and optionally by third and fourth sequences of stages (i), (ii), and (iii) before proceeding to the primary drying stage (iv).

The method described herein can, for example, reduce the overall time for the freeze-drying process by at least a day and, in some embodiments, by up to two days. The method described herein can further allow reconstitution of the solution more readily than compositions prepared using methods that omit the intermediate warming stage. For example, in some embodiments, the reconstitution time of the compositions can be reduced from a time in excess of 30 minutes to a time of less than 20 minutes and, in some embodiments, a time of less than 10 minutes.

The freeze-drying procedure can be carried out in a lyophilization apparatus. The lyophilization apparatus can have a chamber in which lyophilization containers (e.g. lyophilization vials) containing solution can be placed for freeze-drying. The chamber can be connected to a vacuum source (e.g. a vacuum pump) to enable the pressure within the chamber to be reduced. The apparatus can also have components for freezing or heating the contents of the chamber. Prior to freeze-drying, a bulk solution of the compound of formula (1) in DMSO and optionally one or more co-solvents can be prepared and filtered through a filter (e.g. a sterilising filter) before aliquots are filled into lyophilization containers (e.g. lyophilization vials) and transferred to the lyophilization apparatus. Prior to transfer to the lyophilization apparatus, the containers can be partially stoppered to prevent contamination but still permit escape of the solvent during the freeze-drying process.

Parameters of the freeze-drying process are set out in more detail with reference to particular embodiments, sets, subsets, ranges and individual values for each parameter are provided herein. Each embodiment, set, subset, range and individual value defined in relation to one parameter of the freeze-drying process can be combined with each embodiment, set, subset, range and individual value defined in relation to any other parameter of the freeze-drying process. This application therefore discloses all combinations of the embodiments, sets, subsets, ranges and individual values for each parameter of the freeze-drying process.

The temperatures referred to above and elsewhere herein in relation to the parameters of the lyophilization process are the temperatures of the shelves in the lyophilization apparatus. The shelves can be cooled by cooling fluids, the temperatures of which are monitored and provide a method of determining the shelf temperatures. The temperature measurements obtained from the cooling fluids can be cross-checked against temperatures obtained directly from the product in the lyophilization containers by inserting temperature probes into selected lyophilization containers.

In the first freezing stage (i), the solution can be frozen by reducing the temperature thereof to a temperature of no greater than about −20° C., for example, the temperature can be reduced to a value of no greater than about −30° C. (or no greater than about −35° C., or no greater than about −40° C., or no greater than about −41° C., or no greater than about −42° C., or no greater than about −43° C., or no greater than about −44° C.). For example, the solution can be frozen by reducing the temperature to a value in the range from about −40° C. to about −50° C., or about −42° C. to about −48° C., or about −43° C. to about −47° C., or about −44° C. to about −46° C., or at about −45° C.

The first freezing stage can involve a temperature ramping step wherein the temperature is reduced from an initial (e.g. ambient) temperature to a target temperature over a first time period, for example over a period of up to about 2 hours or up to about 1.5 hours or up to 1.25 hours, or up to about 1 hour.

Once the target temperature has been reached, the frozen solution can be held at the target temperature for a second time period, for example up to about 3 hours, or up to about 2.5 hours or up to about 2 hours, or up to about 1.5 hours.

Following the first freezing stage, the solution can be subjected to a first warming stage in which the temperature of the frozen solution is raised to a temperature in the range −15° C. and 4° C. at which the solution remains in a frozen state. For example, the frozen solution can be warmed to a temperature in the range from about −5° C. to about 5° C., or from about −3° C. to about 3° C., or from about −2° C. to about 2° C., or from about −1° C. to about 1° C., for example at about 0° C.

The first warming stage can involve a first time period over which the frozen solution is warmed to a target temperature and a second time period over which the frozen solution is held at the target temperature. For example, the first time period over which the frozen solution is warmed to a target temperature can be up to about 2 hours, or up to about 1.75 hours, or up to about 1.5 hours, or up to about 1.3 hours, or up to about 1.2 hours, or up to about 1.1 hours, or up to about 1 hour.

Following the first warming stage, the still-frozen solution can be subjected to a second freezing stage in which the temperature of the solution in the frozen state is lowered to a temperature of no greater than about −20° C. The temperature can be reduced to a value of no greater than about −30° C. (or no greater than about −35° C., or no greater than about −40° C., or no greater than about −41° C., or no greater than about −42° C., or no greater than about −43° C., or no greater than about 44° C.). For example, the temperature of the frozen solution can be reduced to a value in the range from about −40° C. to about −50° C., or about −42°

C. to about −48° C., or about −43° C. to about −47° C., or about −44° C. to about −46° C., for example, at about −45° C.

After the second freezing stage, the frozen solution can be subjected to a primary drying stage comprising a sublimation step in which dimethylsulfoxide and one or more co-solvents when present are removed by sublimation from the solution in its frozen state under reduced pressure to give a partially dried product. In the primary drying stage, the frozen solution can be warmed to facilitate faster sublimation of the DMSO, whilst maintaining the solution in a frozen state. For example, the frozen solution can be warmed to a temperature in the range from −25° C. to 0° C., or from −22° C. to −2° C., e.g. from about −20° C. to about −5° C.

In the primary drying stage, the frozen solution can be warmed in steps. For example, in a first warming step, the temperature can be raised from a temperature of no greater than about −30° C. to a temperature in the range from about −25° C. to about −19° C. (e.g. about −20° C.), and then held at that temperature for a defined holding period. At this temperature, residual unfrozen solvent and/or co-solvent can be removed by evaporation.

In a second warming step the temperature can be raised from a temperature in the range from about −25° C. to about −19° C. (e.g. about −20° C.), to a temperature in the range from about −10° C. to about 0° C. (e.g. about −5° C.) and then held at that temperature for further defined holding period. Further intermediate warming stages and holding periods can be added to the first and second warming stages. As an alternative to warming the frozen solution in stages, warming can be carried out in a continuous manner until a required target temperature is attained.

At the beginning of the primary drying period, the pressure in the vessel containing the frozen solution can be reduced (typically from atmospheric pressure) to a pressure at which removal of the DMSO and optionally other co-solvents can take place. The pressure can be reduced to a pressure of lower than 1 mBar, for example, below 500 µBar, or less than 100 µBar, or less than 50 µBar. For example, the pressure can be reduced to a pressure of less than 20 µBar, or less than 10 µBar, or from 1 to 10 µBar, or from 4 to 8 µBar, e.g. about 6 µBar.

The primary drying stage can involve an initial pressure-reducing stage in which the temperature is held constant and the pressure is reduced to a target value, followed by warming of the frozen solution as defined above. Alternatively, the reduction in pressure and the warming of the frozen solution can be carried out simultaneously.

The primary drying stage can take from about 20 to about 60 hours, for example, from about 30 to about 50 hours.

The progress of the primary drying stage can be monitored by one or more sensors or gauges present in a lyophilization chamber of the lyophilization apparatus. The sensors or gauges (such as a Pirani gauge) can be used to measure one or more parameters within the chamber, whereby defined changes in the one or more parameters can indicate the progress of the primary drying and provide a means of determining when sublimation of DMSO and optionally any co-solvents has been completed. For example, a sensor or gauge can measure pressure within the chamber or the conductivity of gas in the chamber.

During the sublimation process, the temperature must be below the critical temperature and pressure of the product so that the product remains frozen. Sublimation is a direct solid-to-gas DMSO phase change. If the conditions are above the critical temperature and pressure, the product is not frozen and, instead, is a liquid and the DMSO can change from a liquid-to-gas (boils).

The primary drying stage can be performed under pressures of from about 5 µBar to about 40 µBar. The freezing temperature of the product at these pressures is about −2° C. to about −4° C. The primary drying stage can be performed at temperatures from about −3° C. to about −9° C. At this temperature range, the vapor pressure is adequate for a quick sublimation, which leads to a better product. In some embodiments, the pressure is about 20 µBar. In some embodiments, the temperature is about −6° C.

Once sublimation of the DMSO has ceased, or has fallen below a certain level, the secondary drying stage is initiated. In the secondary drying stage, dimethylsulfoxide and one or more co-solvents when present are removed by evaporation from the partially dried product in a non-frozen state under reduced pressure to give a lyophilized product. Thus, in the secondary drying stage, a reduced pressure environment is maintained and the partially dried product is heated to a temperature at which point the product is no longer frozen. As the boiling point of DMSO is about 189° C., the partially dried product can be heated to a temperature of at least about 40° C., more usually at least about 45° C., for example at least about 50° C., or at least about 55° C. In some embodiments, the partially dried product is heated to a temperature in the range from about 55° C. to about 70° C., for example, about 65° C.

The secondary drying stage can involve one or more temperature ramping steps in which the partially dried product is heated to a target temperature, each temperature ramping step being followed by a temperature holding step. In one embodiment, there is a single temperature ramping step followed by a single temperature holding step.

During the secondary drying stage, unfrozen solvent molecules are removed to give a lyophilized product containing only low levels of residual DMSO.

The secondary drying stage can be performed at a temperature of about 30° C. to about 65° C., for example, about 40° C.

At the end of the secondary drying stage, an inert gas such as nitrogen is admitted into the lyophilization chamber and the containers (e.g. vials) containing the lyophilized product are fully sealed (e.g. by means of stopper and optionally also a cap) under inert gas.

The freeze-drying procedure can be carried out on a solution of a compound of the formula (1) or a pharmaceutically acceptable salt thereof in a non-aqueous solvent comprising dimethylsulfoxide and optionally one or more co-solvents.

A break temperature as described herein can refer to a pausing step in the lyophilization process for which a target shelf temperature has not been assigned. At the break temperature, the temperature in the chamber begins to rise as sublimation of the DMSO during the lyophilization process is completed. The break temperature can be indicated by the measured rising product temperature after the primary drying step when the process reaches a steady state.

In some embodiments, water contamination is avoided at any stage. Hydrate formation can disrupt the product's structure making the product not conducive to easy reconstitution.

In some embodiments, substantially no co-solvents are present; i.e. the solvent consists essentially of DMSO.

In other embodiments, one or more of the other non-aqueous co-solvents can be present. Where a co-solvent is present, the total volume of co-solvent can typically constitute no more than about 25% (v/v) of the total solvent. More usually, the total volume of co-solvent, when present, constitutes no more than about 20%, or no more than about 15%, or no more than about 10%, or no more than about 5% by volume of the total volume of solvent. For example, the total volume of co-solvent, can constitute from about 0% (v/v) to about 5% (v/v) of the total volume of solvent.

The solution to be lyophilized can contain an amount of the compound of formula (1) or the pharmaceutically acceptable salt thereof in the range from about 5 mg/ml to about 200 mg/ml, for example, in the range from about 10 mg/ml to about 150 mg/ml. For example, the solution can contain from about 20 mg/ml to about 120 mg/ml, or from about 22 mg/ml to about 110 mg/ml, or from about 25 mg/ml to about 105 mg/ml, or from about 25 mg/ml to about 100 mg/ml of the compound of formula (1) or the pharmaceutically acceptable salt thereof.

In some embodiments, the solution contains from about 40 mg/ml to about 110 mg/ml, or from about 50 mg/ml to about 105 mg/ml of the compound of formula (1) or the pharmaceutically acceptable salt thereof.

In some embodiments, the solution contains either 75 mg/ml; or 100 mg/ml of a sodium salt of the compound of formula (1).

Non-limiting examples of pressures that can be used during a method described herein include about 1 μBar, about 2 μBar, about 3 μBar, about 4 μBar, about 5 μBar, about 6 μBar, about 7 μBar, about 8 μBar, about 9 μBar, about 10 μBar, about 15 μBar, about 20 μBar, about 25 μBar, about 30 μBar, about 35 μBar, about 40 μBar, about 45 μBar, about 50 μBar, about 55 μBar, about 60 μBar, about 65 μBar, about 70 μBar, about 80 μBar, about 90 μBar, about 100 μBar, about 150 μBar, about 200 μBar, about 250 μBar, about 300 μBar, about 350 μBar, about 400 μBar, about 450 μBar, about 500 μBar, about 550 μBar, about 600 μBar, about 650 μBar, about 700 μBar, about 750 μBar, about 800 μBar, about 850 μBar, about 900 μBar, about 950 μBar, and about 1 mBar.

Non-limiting examples of pressures that can be used during a method described herein include about 0 PSI, about 0.1 PSI, about 0.15 PSI about 0.2 PSI, about 0.25 PSI, about 0.3 PSI, about 0.35 PSI, about 0.4 PSI, about 0.45 PSI, about 0.5 PSI, about 0.55 PSI, about 0.6 PSI, about 0.65 PSI, about 0.7 PSI, about 0.75 PSI, about 0.8 PSI, about 0.85 PSI, about 0.9 PSI, about 0.95 PSI, about 1 PSI, about 1.1 PSI, about 1.2 PSI, about 1.3 PSI, about 1.4 PSI, about 1.5 PSI, about 1.6 PSI, about 1.7 PSI, about 1.8 PSIG, about 1.9 PSI, about 2 PSI, about 2.1 PSI, about 2.2 PSI, about 2.3 PSI, about 2.4 PSI, about 2.5 PSI, about 2.6 PSI, about 2.7 PSI, about 2.8 PSI, about 2.9 PSI, about 3 PSI, about 3.5 PSI, about 4 PSI, about 4.5 PSI, about 5 PSI, about 6 PSI, about 7 PSI, about 8 PSI, about 9 PSI, or about 10 PSI.

Non-limiting examples of pressures that can be used during a method described herein include about 0.5 PSIG (PSI gauge), about 0.6 PSIG, about 0.7 PSIG, about 0.8 PSIG, about 0.9 PSIG, about 1 PSIG, about 1.1 PSIG, about 1.2 PSIG, about 1.3 PSIG, about 1.4 PSIG, about 1.5 PSIG, about 1.6 PSIG, about 1.7 PSIG, about 1.8 PSIG, about 1.9 PSIG, about 2 PSIG, about 2.5 PSIG, about 3 PSIG, about 3.5 PSIG, about 4 PSIG, about 4.5 PSIG, about 5 PSIG, about 6 PSIG, about 7 PSIG, about 8 PSIG, about 9 PSIG, about 10 PSIG, about 15 PSIG, about 20 PSIG, about 25 PSIG, about 30 PSIG, about 35 PSIG, about 40 PSIG, about 45 PSIG, about 50 PSIG, or about 55 PSIG.

Non-limiting examples of pressures that can be used during a method described herein include about 5 PSIA (PSI absolute), about 6 PSIA, about 7 PSIA, about 8 PSIA, about 9 PSIA, about 10 PSIA, about 10.5 PSIA, about 11 PSIA, about 11.5 PSIA, about 12 PSIA, about 12.5 PSIA, about 13 PSIA, about 13.5 PSIA, about 14 PSIA, about 14.1 PSIA, about 14.2 PSIA, about 14.3 PSIA, about 14.4 PSIA, about 14.5 PSIA, about 14.6 PSIA, about 14.7 PSIA, about 14.8 PSIA, about 14.9 PSIA, about 15 PSIG, about 16 PSIA, about 17 PSIA, about 18 PSIA, about 19 PSIA, or about 20 PSIA.

Non-limiting examples of pressures that can be used during a method described herein include about 1 micron (mTorr), about 2 microns, about 3 microns, about 4 microns, about 5 microns, about 6 microns, about 7 microns, about 8 microns, about 9 microns, about 10 microns, about 15 microns, about 20 microns, about 25 microns, about 30 microns, about 35 microns, about 40 microns, about 45 microns, about 50 microns, about 55 microns, about 60 microns, about 65 microns, about 70 microns, about 80 microns, about 90 microns, about 100 microns, about 150 microns, about 200 microns, about 250 microns, about 300 microns, about 350 microns, about 400 microns, about 450 microns, about 500 microns, about 550 microns, about 600 microns, about 650 microns, about 700 microns, about 750 microns, about 800 microns, about 850 microns, about 900 microns, about 950 microns, and about 1000 microns.

Reconstitution of Solution:

The requirements of a constituted solution are that there is no visible insoluble material and the solution is no less clear than the diluent after a predetermined amount of time. The volume for reconstitution can return the product to the same volume and concentration as the bulk solution used for filling or may be the volume intended for patient delivery in a clinical setting.

For reconstitution, a specified volume of a diluent can be drawn up into a syringe. The diluent can then be extruded into the center of the dried cake of the product and the timer started. The product is then inspected at approximately 5 second intervals to determine the time material dissolved.

Methods Used Herein to Assess Lyophilization Process.

Hastings Gauge (Thermocouple Gauge):

Thermocouple type vacuum gauges are an indirect measurement of pressure based upon conduction of heat through a gas. The pressure of a vessel can be measured by the temperature fluctuations of a "hot wire" caused by gas molecules colliding with the wire. When pressure is in the low vacuum range (for example, >100 microns), the number of gas molecules colliding with the hot wire is high. With each gas molecule picking up a quantity of heat upon collision with the wire, there can be a large cooling effect on the wire, reducing the relative temperature as measured by a thermocouple. With the wire held at a constant voltage, changes in temperature can be correlated with an associated vacuum level that can be indicated on an instrument.

When a Hastings gauge monitors the pressure inside, for example a lyophilizer chamber as used herein, the gauge can be used as an indicator of the gas environment within the chamber. The Hastings gauge is adjusted in a pure nitrogen environment; therefore, the gauge reads the chamber pressure based on the thermal conductivity of nitrogen. When the chamber environment includes solvent vapor from the product during primary and secondary drying, the Hastings gauge reads an artificially high pressure due to the difference in the thermal conductivity of the solvent vapor as compared to nitrogen. This offset can be measured by comparing the Hastings gauge reading to the capacitance manometer reading, which is used to control chamber pressure.

The Hastings gauge reading returns to match the capacitance manometer reading as the level of solvent vapor in the chamber environment drops, indicating the end of sublimation in primary drying or the end of desorption in secondary drying. The sensitivity of the Hastings gauge is dependent upon the change in thermal conductivity, which can depend on the relative difference in thermal conductivity of the solvent vapor and nitrogen as well as the ratio of solvent vapor to nitrogen in the chamber environment.

Residual Gas Analyzer (RGA):

The RGA is a mass spectrometer that can monitor the chamber environment using quadrupole mass analyzer technology at sub-atmospheric pressures. A MKS Microvision Plus RGA is connected to a port on the chamber. Test parameters and data collection are implemented using the Process Eye™ Professional Software. The RGA can resolve constituents in the environment with atomic masses from 1 to 90 in a pressure range of $2 \times 10^{-4}$ to $2 \times 10^{-9}$ Torr.

The RGA can be programmed to scan a chamber every 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, or an hour. In some embodiments, the RGA scans a chamber every 5 minutes.

An automatic valve isolates the RGA from the chamber until the pressure in the chamber is below 1000 microns. A small orifice can be in line between the chamber and the RGA to induce the pressure drop necessary to maintain the instrument pressure in the required range. The relative amount of DMSO and nitrogen present in the chamber are monitored during Primary Drying to confirm the end of the sublimation of ice. DMSO has a NIST reported primary ion at 63 atomic mass units (AMU) with the parent compound, 78 AMU, as the secondary peak.

Turbidity:

Turbidity monitors the transmission of light through a liquid sample to determine whether the sample is clear or the degree of opalescence in the sample. The analysis can be performed using a Hach Model 2100AN Laboratory Turbidimeter. The Hach Model 2100AN is a ratio turbidimeter that uses the ratio of transmitted to scattered light to reduce error in the measurement caused by colored solutions.

Prior to each use, the Turbidimeter is calibrated with a Hach StabCal® Calibration Kit and then checked using Hach Gelex® Secondary Turbidity Standards. Sample cells are cleaned and oiled to reduce interference by dirt or imperfections in the glass. Sample cell indexing matches cells with similar interference for sample comparison.

Reconstituted samples can be pooled to achieve at least 2.5 mL of sample, which is placed in the indexed sample cells for analysis. The turbidimeter measures the opalescence and returns a value in nephelometric turbidity units (NTU) ratio. This value was recorded by the instrument with a time and date stamp to track each sample.

High Temperature Differential Scanning Calorimetry (HT-DSC):

High temperature modulated differential scanning calorimetry (MDSC, 2° C./min) was used as a means of determining the thermal characteristics of solid materials. HT-DSC followed the current USP<891> Thermal Analysis, and was performed using a TA Instruments Q200. Test parameters and data analysis were conducted using TA Instruments Universal Analysis® software version 4.5A.

Briefly, solid material, with a weight of 3 mg to 6 mg, was placed in an aluminum sample pan with a crimped vented lid. Nitrogen, NF was used to purge the sample continuously at a flow rate of 50 mL/minute. The sample was heated from 20° C. to 200° C. at 10° C./min or 2° C./min (with a modulation of ±0.32° C. every 60 seconds). The instrument was calibrated at temperatures that spanned the range of high temperature analysis as performed herein.

Physical Inspection:

Physical inspection can be used to evaluate the uniformity of appearance of the end product in terms of, for example, color, texture, shape, and structure, and can provide insight into the relative effects of processing of the finished sample. The extent, range, and/or consistency for each attribute can be considered and recorded.

Color can be characterized as intensity of the color, hue, or tint indicating the color tone and shade that reflects lightness to darkness of the color. Product structure can be described as dense or open, granular, or geometric looking shapes, or a composition that makes up the arrangement, configuration, pattern, or organization of the structure. Texture can be characterized as being in a range from smooth to fine, appearing like powdered sugar or chalk with indistinguishable finite structure, to a coarse texture where structure is easily observed.

Each sample can be viewed at the bottom, sides and top surface of the cake while rotating the container to view all sides.

Thermogravimetric Analysis (TGA):

TGA can be used as a corroborative method for residual moisture determination where the change in weight is attributed to the evolution of volatile substances, such as water. In addition, TGA can be used to deter mine physico-chemical changes as the specimen begins to decompose at elevated temperatures.

TGA monitors the change in weight of a material as a function of temperature or time with heating. The analysis can be performed using a TA Instruments QSO per USP 891, Thermal Analysis. Test parameters and data analysis can conducted using TA Instruments Universal Analysis® software version 4.5A on a PC interface.

Solid material, with a weight of about 13 mg to about 19 mg, can be placed in an open ceramic sample pan. The sample is then heated from 25° C. to 400° C. using a warming rate of about 10° C. per minute to measure the weight loss across the temperature range. Nitrogen, NF is used to purge the sample continuously at a flow rate of 60 mL/minute. The instrument is calibrated at temperatures that span the range of high temperature analysis.

The lyophilized material is warmed and the sample weight can be monitored for any change. During warming, weight loss is correlated to the evolution of volatile components in the sample. Calculations identify the sample weight correlated to a temperature.

Lyophilized Pharmaceutical Compositions.

The present disclosure provides a lyophilized pharmaceutical composition, which is preparable by (or prepared by) a freeze-drying process as described herein.

The lyophilized pharmaceutical compositions of the present disclosure are characterized by enhanced solubility relative to known lyophilized formulations of compounds of the formula (1) and their salts. Accordingly, in another embodiment, the present disclosure provides a lyophilized pharmaceutical composition comprising a compound of formula (1) or a pharmaceutically acceptable salt thereof, which is obtainable by a freeze-drying process as defined herein and which has a dissolution time, at ambient temperature, and without the aid of mechanised stirring, in a non-aqueous solvent containing 65% (v/v) propylene glycol; 25% (v/v) glycerine; and 10% (v/v) ethanol, of no greater than 20 minutes.

In some embodiments, the lyophilized pharmaceutical composition has a dissolution time in the non-aqueous solvent of no greater than 15 minutes, or no greater than 12 minutes.

In particular embodiments, the lyophilized pharmaceutical composition has a dissolution time in the non-aqueous solvent of no greater than 10 minutes.

The lyophilized pharmaceutical compositions described herein are also characterised by reduced levels of residual DMSO solvent. Accordingly, in another embodiment, the present disclosure provides a lyophilized pharmaceutical composition comprising a compound of formula (1) or a pharmaceutically acceptable salt thereof, which is obtainable by a freeze-drying process as defined herein and wherein, in an amount of lyophilized composition obtained from 1 gram of solution, there is a residual DMSO content of no greater than 20 mg, or no greater than 19 mg. A solution can be the solution of the pharmaceutically acceptable salt thereof in a solvent comprising dimethylsulfoxide and optionally one or more co-solvents. The solvent can be non-aqueous, anhydrous or substantially-anhydrous.

In another embodiment, there is provided a lyophilized pharmaceutical composition comprising a compound of formula (1) or a pharmaceutically acceptable salt thereof, which is obtainable by a freeze-drying process as defined herein and wherein any residual DMSO is present in the composition in an amount corresponding to no more than 35 mg per 100 mg equivalent of the free base of the compound of formula (1).

The term "100 mg equivalent of the free base" can refer to the amount by weight of free base that can be present or, when the compound of formula (1) is in the form of a salt, to the amount by weight of the free base contained within the salt. For example, the amount of residual DMSO per 100 mg equivalent of the free base is no more than about 32 mg, or no more than about 31 mg, for example in the range from about 15 mg to about 35 mg, or from about 20 mg to about 32 mg, or from about 25 mg to about 30 mg.

In some embodiments, there is provided a lyophilized pharmaceutical composition comprising a compound of formula (1) or a pharmaceutically acceptable salt thereof, which is obtainable by a freeze-drying process as defined herein and which: (a) has a dissolution time, at ambient temperature, and without the aid of mechanised stirring, in a solvent containing 65% (v/v) propylene glycol; 25% (v/v) glycerine; and 10% (v/v) ethanol, of no greater than 20 minutes (or no greater than 15, or 12 or 10 minutes); and (b) has a residual DMSO content such that, in an amount of lyophilized composition obtained from 1 gram of solution, the residual DMSO content is no greater than 20 mg, or no greater than 19 mg. The solvent can be non-aqueous, anhydrous or substantially-anhydrous.

The lyophilized pharmaceutical compositions described herein, i.e. the compositions obtainable by the freeze-drying process as described herein, can also be characterised with regard to their enhanced porosity, and increased specific surface area compared to known compositions. The specific surface area can be measured using known techniques such as the Brunauer-Emmett-Teller (BET) adsorption method.

The lyophilized pharmaceutical compositions described herein can be provided in sealed containers such as vials (e.g. glass vials), optionally containing a protective atmosphere of an inert gas such as nitrogen or argon. The sealed containers can be opened when required and the contents reconstituted by dissolving in a reconstitution solvent, such as a non-aqueous, anhydrous or substantially-anhydrous solvent, prior to administration to a patient.

The present disclosure further provides a sealed pharmaceutical container containing a lyophilized pharmaceutical composition as described herein. The sealed pharmaceutical container can be, for example, a vial fitted with a stopper and optionally additional components (such as a collar) for holding the stopper in place. The sealed container can optionally contain a protective atmosphere of an inert gas such as nitrogen or argon.

In some embodiments, the present disclosure provides a sealed pharmaceutical container containing a lyophilized pharmaceutical composition as described herein wherein the composition contains the compound of formula (1) or a pharmaceutically acceptable salt thereof in an amount corresponding to about 100 mg equivalent of the free base of the compound of formula (1), and wherein no more than 35 mg of residual DMSO is present in the composition.

Reconstituted Formulations Prepared from the Lyophilized Pharmaceutical Compositions.

The lyophilized pharmaceutical compositions described herein can be reconstituted in solvents, such as non-aqueous, anhydrous or substantially-anhydrous solvents, to give injectable liquid compositions for administration to a subject. The liquid compositions can be for administration by subcutaneous injection. The present disclosure further provides a method for preparing an injectable liquid composition, which method can involve dissolving a lyophilized pharmaceutical composition as described herein in a solvent, particularly a non-aqueous solvent.

Non-limiting examples of suitable solvents include propylene glycol, glycerin, ethanol, and any combination of the foregoing. The formulations can be prepared as non-aqueous formulations. The formulations can be anhydrous or substantially anhydrous.

A mixture of solvents can contain a percentage of propylene glycol on either a mass or a volume basis. In some embodiments, the percentage of propylene glycol can be at least about 10%, at least about 20%, at least about 30%, at least about 40%, at least about 50%, at least about 10%, at least about 20%, at least about 30%, at least about 40%, or at least about 50%. In some embodiments, the percentage of propylene glycol can be at most 90%, at most 80%, at most 70%, at most 60%, at most about 90%, at most about 80%, at most about 70%, or at most about 60%. In some embodiments, the percentage of propylene glycol can be about 30% to about 90%, about 45% to about 85%, about 55% to about 75%, about 60% to about 70%, about 30% to about 90%, about 45% to about 85%, about 55% to about 75%, or about 60% to about 70%. In some embodiments, the percentage of propylene glycol can be 30%, 35%, 40%, 45%, 50%, 55%, 60%, 65%, 70%, 75%, 80%, 85%, 90%, about 30%, about 35%, about 40%, about 45%, about 50%, about 55%, about 60%, about 65%, about 70%, about 75%, about 80%, about 85%, or about 90%.

A mixture of solvents can contain a percentage of glycerin on either a mass or a volume basis. In some embodiments, the percentage of glycerin can be at least 5%, at least 10%, at least 15%, at least 25%, at least 30%, at least about 5%, at least about 10%, at least about 15%, at least about 25%, or at least about 30%. In some embodiments, the percentage of glycerin can be at most 70%, at most 60%, at most 50%, at most 40%, at most 30%, at most about 70%, at most about 60%, at most about 50%, at most about 40%, or at most about 30%. In some embodiments, the percentage of glycerin can be 0% to 50%, 5% to 45%, 15% to 35%, 20% to 30%, 0% to about 50%, about 5% to about 45%, about 15% to about 35%, or about 20% to about 30%. In some embodiments, the percentage of glycerin can be 0%, 5%, 10%, 15%, 20%, 25%, 30%, 35%, 40%, 45%, 50%, about 5%, about 10%, about 15%, about 20%, about 25%, about 30%, about 35%, about 40%, about 45%, or about 50%.

A mixture of solvents can contain a percentage of ethanol on either a mass or a volume basis. In some embodiments, the percentage of ethanol can be at least 1%, at least 3%, at least 5%, at least 10%, at least 15%, at least about 1%, at least about 3%, at least about 5%, at least about 10%, or at least about 15%. In some embodiments, the percentage of ethanol can be at most 30%, at most 25%, at most 20%, at most 15%, at most 10%, at most about 30%, at most about 25%, at most about 20%, at most about 15%, or at most about 10%. In some embodiments, the percentage of ethanol can be 0% to 30%, 0% to 25%, 0% to 20%, 5% to 15%, 0% to about 30%, 0% to about 25%, 0% to about 20%, or about 5% to about 15%. In some embodiments, the percentage of ethanol can be 0%, 1%, 2%, 3%, 4%, 5%, 6%, 7%, 8%, 9%, 10%, 11%, 12%, 13%, 14%, 15%, about 1%, about 2%, about 3%, about 4%, about 5%, about 6%, about 7%, about 8%, about 9%, about 10%, about 11%, about 12%, about 13%, about 14%, or about 15%.

In some embodiments, a solvent or a mixture of solvents contains 45% to 85% propylene glycol, 5% to 45% glycerin, and 0% to 30% ethanol. In some embodiments, a solvent or a mixture of solvents contains about 45% to about 85% propylene glycol, about 5% to about 45% glycerin, and 0% to about 30% ethanol. In some embodiments, a solvent or a mixture of solvents consists essentially of 45% to 85% propylene glycol, 5% to 45% glycerin, and 0% to 30% ethanol. In some embodiments, a solvent or a mixture of solvents consists essentially of about 45% to about 85% propylene glycol, about 5% to about 45% glycerin, and 0% to about 30% ethanol. In some embodiments, a solvent or a mixture of solvents is 45% to 85% propylene glycol, 5% to 45% glycerin, and 0% to 30% ethanol. In some embodiments, a solvent or a mixture of solvents is about 45% to about 85% propylene glycol, about 5% to about 45% glycerin, and 0% to about 30% ethanol.

In some embodiments, a solvent or a mixture of solvents comprises 55% to 75% propylene glycol, 15% to 35% glycerin, and 0% to 20% ethanol. In some embodiments, a solvent or a mixture of solvents comprises about 55% to about 75% propylene glycol, about 15% to about 35% glycerin, and 0% to about 20% ethanol. In some embodiments, a solvent or a mixture of solvents consists essentially of 55% to 75% propylene glycol, 15% to 35% glycerin, and 0% to 20% ethanol. In some embodiments, a solvent or a mixture of solvents consists essentially of about 55% to about 75% propylene glycol, about 15% to about 35% glycerin, and 0% to about 20% ethanol. In some embodiments, a solvent or a mixture of solvents is 55% to 75% propylene glycol, 15% to 35% glycerin, and 0% to 20% ethanol. In some embodiments, a solvent or a mixture of solvents is about 55% to about 75% propylene glycol, about 15% to about 35% glycerin, and 0% to about 20% ethanol.

In some embodiments, a solvent or a mixture of solvents comprises 60% to 70% propylene glycol; 20% to 30% glycerin; and 5% to 15% ethanol. In some embodiments, a solvent or a mixture of solvents comprises about 60% to about 70% propylene glycol; about 20% to about 30% glycerin; and about 5% to about 15% ethanol. In some embodiments, a solvent or a mixture of solvents consists essentially of 60% to 70% propylene glycol; 20% to 30% glycerin; and 5% to 15% ethanol. In some embodiments, a solvent or a mixture of solvents consists essentially of about 60% to about 70% propylene glycol; about 20% to about 30% glycerin; and about 5% to about 15% ethanol. In some embodiments, a solvent or a mixture of solvents is 60% to 70% propylene glycol; 20% to 30% glycerin; and 5% to 15% ethanol. In some embodiments, a solvent or a mixture of solvents is about 60% to about 70% propylene glycol; about 20% to about 30% glycerin; and about 5% to about 15% ethanol.

In some embodiments, a solvent or a mixture of solvents comprises 65% propylene glycol; 25% glycerin; and 10% ethanol. In some embodiments, a solvent or a mixture of solvents comprises about 65% propylene glycol; about 25% glycerin; and about 10% ethanol. In some embodiments, a solvent or a mixture of solvents consists essentially of 65% propylene glycol; 25% glycerin; and 10% ethanol. In some embodiments, a solvent or a mixture of solvents consists essentially of about 65% propylene glycol; about 25% glycerin; and about 10% ethanol. In some embodiments, a solvent or a mixture of solvents is 65% propylene glycol; 25% glycerin; and 10% ethanol. In some embodiments, a solvent or a mixture of solvents is about 65% propylene glycol; about 25% glycerin; and about 10% ethanol.

Excipients.

A pharmaceutical composition described herein can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, rectal, aerosol, parenteral, ophthalmic, pulmonary, transdermal, vaginal, otic, nasal, and topical administration.

A pharmaceutical composition can be administered in a local or systemic manner, for example, via injection of the compound directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated readily by combining the active compounds with pharmaceutically-acceptable carriers or excipients. Such carriers can be used to formulate tablets, powders, pills, dragees, capsules, liquids, gels, syrups, elixirs, slurries, and suspensions, for oral ingestion by a subject.

Pharmaceutical preparations for oral use can be obtained by mixing one or more solid excipient with one or more of the compounds described herein, optionally grinding the resulting mixture, and processing the mixture of granules, after adding suitable auxiliaries, if desired, to obtain tablets or dragee cores. Cores can be provided with suitable coatings. For this purpose, concentrated sugar solutions can be used, which can contain an excipient such as gum arabic, talc, polyvinylpyrrolidone, carbopol gel, polyethylene glycol, and/or titanium dioxide, lacquer solutions, and suitable organic solvents or solvent mixtures. Dyestuffs or pigments can be added to the tablets or dragee coatings, for example, for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. In some embodiments, the capsule comprises a hard gelatin capsule comprising one or more of pharmaceutical, bovine, and plant gelatins. A gelatin can be alkaline-processed. The push-fit capsules can contain the active ingredients in admixture with filler such as lactose, binders such as starches, and/or lubricants such as talc or magnesium stearate and, stabilizers. In soft capsules, the active compounds can be dissolved or suspended in suitable liquids, such as fatty oils, liquid paraffin, or liquid polyethylene glycols. Stabilizers can be added. All formulations for oral administration are provided in dosages suitable for such administration.

For buccal or sublingual administration, the compositions can be tablets, lozenges, or gels.

Parenteral injections can be formulated for bolus injection or continuous infusion. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. Aqueous injection suspensions can contain substances which increase the viscosity of the suspension, such as sodium carboxymethyl cellulose, sorbitol, or dextran. The suspension can also contain suitable stabilizers or agents which increase the solubility of the compounds to allow for the preparation of highly concentrated solutions. Alternatively, the active ingredient can be in powder form for constitution with a suitable vehicle, for example, sterile pyrogen-free water, 0.9% saline, or 5% dextrose in water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

Formulations suitable for transdermal administration of the active compounds can employ transdermal delivery devices and transdermal delivery patches, and can be lipophilic emulsions or buffered aqueous solutions, dissolved and/or dispersed in a polymer or an adhesive. Such patches can be constructed for continuous, pulsatile, or on demand delivery of pharmaceutical compounds. Transdermal delivery can be accomplished by means of iontophoretic patches. Additionally, transdermal patches can provide controlled delivery. The rate of absorption can be slowed by using rate-controlling membranes or by trapping the compound within a polymer matrix or gel. Conversely, absorption enhancers can be used to increase absorption. An absorption enhancer or carrier can include absorbable pharmaceutically acceptable solvents to assist passage through the skin. For example, transdermal devices can be in the form of a bandage comprising a backing member, a reservoir containing compounds and carriers, a rate controlling barrier to deliver the compounds to the skin of the subject at a controlled and predetermined rate over a prolonged period of time, and adhesives to secure the device to the skin or the eye.

For administration by inhalation, the active compounds can be in a form as an aerosol, a mist, or a powder. Pharmaceutical compositions are conveniently delivered in the form of an aerosol spray presentation from pressurized packs or a nebuliser, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone and PEG. In suppository forms of the compositions, a low-melting wax such as a mixture of fatty acid glycerides or cocoa butter can be used.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulation can be modified depending upon the route of administration chosen. Pharmaceutical compositions comprising a compounds described herein can be manufactured, for example, by mixing, dissolving, granulating, dragee-making, levigating, emulsifying, encapsulating, entrapping, or compression processes.

The pharmaceutical compositions can include at least one pharmaceutically acceptable carrier, diluent, or excipient and compounds described herein as free-base or pharmaceutically-acceptable salt form. The methods and pharmaceutical compositions described herein include the use of crystalline forms (also known as polymorphs), and active metabolites of these compounds having the same type of activity.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use herein include feed, food, pellet, lozenge, liquid, elixir, aerosol, inhalant, spray, powder, tablet, pill, capsule, gel, geltab, nanosuspension, nanoparticle, microgel, suppository troches, aqueous or oily suspensions, ointment, patch, lotion, dentifrice, emulsion, creams, drops, dispersible powders or granules, emulsion in hard or soft gel capsules, syrups, phytoceuticals, nutraceuticals, and any combination thereof.

Non-limiting examples of pharmaceutically-acceptable excipients suitable for use herein include granulating agents, binding agents, lubricating agents, disintegrating agents, sweetening agents, glidants, anti-adherents, anti-static agents, surfactants, anti-oxidants, gums, coating agents, coloring agents, flavouring agents, coating agents, plasticizers, preservatives, suspending agents, emulsifying agents, anti-microbial agents, plant cellulosic material and spheronization agents, and any combination thereof.

A composition described herein can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that drug release rates and drug release profiles can be matched to physiological and chronotherapeutic requirements or, alternatively, has been formulated to effect release of a drug at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

The disclosed compositions can optionally comprise from about 0.001% to about 0.005% weight by volume pharmaceutically acceptable preservatives. One non-limiting example of a suitable preservative is benzyl alcohol.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999), each of which is incorporated by reference in its entirety.

The disclosed methods include administration of a decitabine derivative dinucleotide, or a pharmaceutically acceptable salt thereof, in combination with a pharmaceutically acceptable carrier. The carrier can be selected to minimize any degradation of the active ingredient and to minimize any adverse side effects in the subject.

The compound of formula (1) or a pharmaceutically acceptable salt thereof herein can be conveniently formulated into pharmaceutical compositions composed of one or more pharmaceutically acceptable carriers. See e.g., *Remington's Pharmaceutical Sciences*, latest edition, by E.W. Martin Mack Pub. Co., Easton, Pa., which discloses typical carriers and conventional methods of preparing pharmaceutical compositions that can be used in conjunction with the preparation of formulations of the compound described herein and which is incorporated by reference herein. Such pharmaceuticals can be standard carriers for administration of compositions to humans and non-humans, including solutions such as, saline and buffered solutions at physiological pH. Other compositions can be administered according to standard procedures. For example, pharmaceutical compositions can also include one or more additional active ingredients such as antimicrobial agents, anti-inflammatory agents, and anesthetics.

Non-limiting examples of pharmaceutically-acceptable carriers include, but are not limited to, saline, Ringer's solution and dextrose solution. The pH of the solution can be from about 5 to about 8, and can be from about 7 to about 7.5. Further carriers include sustained release preparations such as semipermeable matrices of solid hydrophobic polymers containing the compound of formula (1) or a pharmaceutically-acceptable salt thereof, where the matrices are in the form of shaped articles, e.g., films, liposomes, microparticles, or microcapsules.

The disclosed methods relate to administering the compound of formula (1) or a pharmaceutically acceptable salt thereof as part of a pharmaceutical composition. In various embodiments, compositions described herein can comprise a liquid comprising an active agent in solution, in suspension, or both. Liquid compositions can include gels. In one embodiment, the liquid composition is aqueous. Alternatively, the composition can take form of an ointment. In another embodiment, the composition is an in situ gellable aqueous composition. In some embodiments, the composition is an in situ gellable aqueous solution.

Pharmaceutical formulations can include additional carriers, as well as thickeners, diluents, buffers, preservatives, and surface active agents in addition to the compounds disclosed herein. Pharmaceutical formulations can also include one or more additional active ingredients such as antimicrobial agents, anti-inflammatory agents, and anesthetics.

An excipient can fill a role as simple and direct as being an inert filler, or an excipient as used herein can be part of a pH stabilizing system or coating to insure delivery of the ingredients safely to the stomach.

The compound of formula (1) or a pharmaceutically-acceptable salt thereof can also be present in liquids, emulsions, or suspensions for delivery of active therapeutic agents in aerosol form to cavities of the body such as the nose, throat, or bronchial passages. The ratio of the compound of formula (1) or a pharmaceutically-acceptable salt thereof to the other compounding agents in these preparations can vary as the dosage form requires.

Depending on the intended mode of administration, the pharmaceutical compositions administered as part of the disclosed methods can be in the form of solid, semi-solid or liquid dosage forms, such as, for example, tablets, suppositories, pills, capsules, powders, liquids, suspensions, lotions, creams, gels, or the like, for example, in unit dosage form suitable for single administration of a precise dosage. The compositions can contain, as noted above, an effective amount of the compound of formula (1) or a pharmaceutically-acceptable salt thereof in combination with a pharmaceutically-acceptable carrier and, in addition, can include other medicinal agents, pharmaceutical agents, carriers, adjuvants, diluents, etc.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Pharmaceutically Acceptable Salts.

In each of the foregoing aspects and embodiments described herein, the compound of formula (1) can be used in the form of a salt or a non-salt.

Pharmaceutically-acceptable salts include, for example, acid-addition salts and base-addition salts. The acid that is added to a compound to form an acid-addition salt can be an organic acid or an inorganic acid. A base that is added to a compound to form a base-addition salt can be an organic base or an inorganic base. In some embodiments, a pharmaceutically-acceptable salt is a metal salt. In some embodiments, a pharmaceutically-acceptable salt is an ammonium salt.

Acid addition salts can arise from the addition of an acid to a compound described herein. In some embodiments, the acid is organic. In some embodiments, the acid is inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, citric acid, oxalic acid, maleic acid, hydroxymaleic acid, methylmaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid, p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid.

Non-limiting examples of suitable acid addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrogen phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methylmaleate salt, a glycolate salt, a malate salt, a cinnamate salt, a mandelate salt, a 2-phenoxybenzoate salt, a 2-acetoxybenzoate salt, an embonate salt, a phenylacetate salt, an N-cyclohexylsulfamate salt, a methanesulfonate salt, an ethanesulfonate salt, a benzenesulfonate salt, a p-toluenesulfonate salt, a 2-hydroxyethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, a glucose-6-phosphate salt, and an amino acid salt.

Metal salts can arise from the addition of an inorganic base to a compound described herein. The inorganic base consists of a metal cation paired with a basic counterion, such as, for example, hydroxide, carbonate, bicarbonate, or phosphate. The metal can be an alkali metal, alkaline earth metal, transition metal, or main group metal. Non-limiting examples of suitable metals include lithium, sodium, potassium, cesium, cerium, magnesium, manganese, iron, calcium, strontium, cobalt, titanium, aluminum, copper, cadmium, and zinc.

Non-limiting examples of suitable metal salts include a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, and a zinc salt.

Ammonium salts can arise from the addition of ammonia or an organic amine to a compound described herein. Non-limiting examples of suitable organic amines include triethyl amine, diisopropyl amine, ethanol amine, diethanol amine, triethanol amine, morpholine, N-methylmorpholine, piperidine, N-methylpiperidine, N-ethylpiperidine, dibenzyl amine, piperazine, pyridine, pyrrazole, pipyrrazole, imidazole, pyrazine, pipyrazine, ethylenediamine, N,N'-dibenzylethylene diamine, procaine, chloroprocaine, choline, dicyclohexyl amine, and N-methylglucamine.

Non-limiting examples of suitable ammonium salts include is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzyl amine salt, a piperazine salt, a pyridine salt, a pyrrazole salt, a pipyrrazole salt, an imidazole salt, a pyrazine salt, a pipyrazine salt, an ethylene diamine salt, an N,N'-dibenzylethylene diamine salt, a procaine salt, a chloroprocaine salt, a choline salt, a dicyclohexyl amine salt, and a N-methylglucamine salt.

One particular example of a salt of the compound of formula (1) is a sodium salt.

Therapeutic Uses.

The lyophilized pharmaceutical compositions according to the present disclosure can be used to treat a wide variety of diseases that are sensitive to the treatment with decitabine, including those described herein.

Accordingly, in other aspects, the present disclosure provides: (i) a lyophilized pharmaceutical composition as described herein for use in medicine; (ii) a lyophilized pharmaceutical composition as described herein for use in the treatment of a disease as described herein; (iii) a method of treating a disease as described herein, which method comprises mixing a lyophilized pharmaceutical composition as described herein with a pharmaceutically acceptable solvent and administering an effective amount of the mixture to a subject in need thereof; (iv) the use of a lyophilized pharmaceutical composition as described herein for the manufacture of a medicament for the treatment of a disease as described herein; (v) a method of treating cancer in a patient in need thereof, which method comprises reconstituting the lyophilized pharmaceutical composition as described herein in a pharmaceutically acceptable solvent to give a liquid formulation containing a compound of formula (1) or a pharmaceutically acceptable salt thereof, and administering a therapeutically effective amount of the liquid formulation to the patient.

Examples of diseases that can be treated using the lyophilized pharmaceutical compositions of the present disclosure include those involving undesirable or uncontrolled cell proliferation. Such indications include benign tumors, various types of cancers such as primary tumors and tumor metastasis, restenosis (e.g. coronary, carotid, and cerebral lesions), hematological disorders, abnormal stimulation of endothelial cells (atherosclerosis), insults to body tissue due to surgery, abnormal wound healing, abnormal angiogenesis, diseases that produce fibrosis of tissue, repetitive motion disorders, disorders of tissues that are not highly vascularized, and proliferative responses associated with organ transplants.

Generally, cells in a benign tumor retain their differentiated features and do not divide in a completely uncontrolled manner. A benign tumor is usually localized and nonmetastatic. Specific types benign tumors that can be treated using the present disclosure include hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas.

In a malignant tumor cells become undifferentiated, do not respond to the body's growth control signals, and multiply in an uncontrolled manner. The malignant tumor is invasive and capable of spreading to distant sites (metastasizing). Malignant tumors are generally divided into two categories: primary and secondary. Primary tumors arise directly from the tissue in which they are found. A secondary tumor, or metastasis, is a tumor which is originated elsewhere in the body but has now spread to a distant organ. The common routes for metastasis are direct growth into adjacent structures, spread through the vascular or lymphatic systems, and tracking along tissue planes and body spaces (peritoneal fluid, cerebrospinal fluid, etc.)

Examples of cancers are carcinomas, for example carcinomas of the bladder, breast, colon, kidney, epidermis, liver, lung, oesophagus, gall bladder, ovary, pancreas, stomach, cervix, thyroid, prostate, gastrointestinal system, or skin, hematopoieitic tumours such as leukaemia, B-cell lymphoma, T-cell lymphoma, Hodgkin's lymphoma, non-Hodgkin's lymphoma, hairy cell lymphoma, or Burkett's lymphoma; hematopoieitic tumours of myeloid lineage, for example acute and chronic myelogenous leukaemias, myelodysplastic syndrome, or promyelocytic leukaemia; thyroid follicular cancer; tumours of mesenchymal origin, for example fibrosarcoma or habdomyosarcoma; tumours of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

Specific types of cancers or malignant tumors, either primary or secondary, that can be treated using the compositions described herein include, for example, bladder cancer, breast cancer, ovarian cancer, skin cancer, bone cancer, prostate cancer, liver cancer, lung cancer, brain cancer, cancer of the larynx, gall bladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteo sarcoma, Ewing's sarcoma, veticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuronms, intestinal ganglloneuromas, hyperplastic corneal nerve tumor, marfanoid habitus tumor, Wilm's tumor, seminoma, ovarian tumor, leiomyomater tumor, cervical dysplasia and in situ carcinoma, neuroblastoma, retinoblastoma, soft tissue sarcoma, malignant carcinoid, topical skin lesion, mycosis fungoide, rhabdomyosarcoma, Kaposi's sarcoma, osteogenic and other sarcoma, malignant hypercalcemia, renal cell tumor, polycythermia vera, adenocarcinoma, glioblastoma multiforma, leukemias, lymphomas, malignant melanomas, epidermoid carcinomas, and other carcinomas and sarcomas.

In one embodiment, the cancer is selected from myelodysplastic syndrome, acute myelogenous leukaemia, ovarian cancer, liver cancer, and colorectal cancer.

Hematologic disorders include abnormal growth of blood cells, which can lead to dysplastic changes in blood cells and hematologic malignancies such as various leukemias. Examples of hematologic disorders include but are not limited to acute myeloid leukemia, acute promyelocytic leukemia, acute lymphoblastic leukemia, chronic myelogenous leukemia, the myelodysplastic syndromes, and sickle cell anemia.

Treatment of abnormal cell proliferation due to insults to body tissue during surgery can be possible for a variety of surgical procedures, including joint surgery, bowel surgery, and cheloid scarring. Diseases that produce fibrotic tissue include emphysema.

Repetitive motion disorders that can be treated using the present disclosure include carpal tunnel syndrome. An example of cell proliferative disorders that can be treated using the present disclosure is a bone tumor.

The proliferative responses associated with organ transplantation that can be treated using the present disclosure include those proliferative responses contributing to potential organ rejections or associated complications. Specifically, these proliferative responses can occur during transplantation of the heart, lung, liver, kidney, and other body organs or organ systems.

Abnormal angiogenesis that can be treated using the present disclosure include those abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopathy, and other ocular angiogenic diseases such as retinopathy of prematurity (retrolental fibroplastic), muscular degeneration, corneal graft rejection, neuroscular glaucoma and Oster Webber syndrome.

Diseases associated with abnormal angiogenesis require or induce vascular growth. For example, corneal angiogenesis involves three phases: a pre-vascular latent period, active neovascularization, and vascular maturation and regression. The identity and mechanism of various angiogenic factors, including elements of the inflammatory response, such as leukocytes, platelets, cytokines, and eicosanoids, or unidentified plasma constituents have yet to be revealed.

In some embodiments, the lyophilized pharmaceutical compositions of the present disclosure can be used for treating diseases associated with undesired or abnormal angiogenesis. The method of treatment can involve administering to a patient suffering from undesired or abnormal angiogenesis the pharmaceutical formulations of the present disclosure alone, or in combination with an anti-neoplastic agent whose activity as an anti-neoplastic agent in vivo is adversely affected by high levels of DNA methylation. The particular dosage of these agents required to inhibit angiogenesis and/or angiogenic diseases can depend on the severity of the condition, the route of administration, and related factors that can be decided by the attending physician. Generally, accepted and effective daily doses are the amount sufficient to effectively inhibit angiogenesis and/or angiogenic diseases.

The lyophilized pharmaceutical compositions of the present disclosure can be used to treat a variety of diseases associated with undesirable angiogenesis such as retinal/choroidal neuvascularization and corneal neovascularization. Examples of retinal/choroidal neuvascularization include, but are not limited to, Bests diseases, myopia, optic pits, Stargarts diseases, Pagets disease, vein occlusion, artery occlusion, sickle cell anemia, sarcoid, syphilis, pseudoxanthoma elasticum carotid abostructive diseases, chronic uveitis/vitritis, mycobacterial infections, Lyme's disease, systemic lupus erythematosis, retinopathy of prematurity, Eales disease, diabetic retinopathy, macular degeneration, Bechets diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularization of the angle) and diseases caused by the abnormal proliferation of fibrovascular or fibrous tissue including all forms of proliferative vitreoretinopathy. Examples of corneal neuvascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

In some embodiments, the lyophilized pharmaceutical compositions of the present disclosure can be used for treating chronic inflammatory diseases associated with abnormal angiogenesis. The method comprises administering to a patient suffering from a chronic inflammatory disease associated with abnormal angiogenesis the pharmaceutical formulations of the present disclosure alone, or in combination with an anti-neoplastic agent whose activity as an anti-neoplastic agent in vivo is adversely affected by high levels of DNA methylation. The chronic inflammation depends on continuous formation of capillary sprouts to maintain an influx of inflammatory cells. The influx and presence of the inflammatory cells produce granulomas and thus, maintains the chronic inflammatory state. Inhibition of angiogenesis using the pharmaceutical formulations of the present disclosure can prevent the formation of the granulomas, thereby alleviating the disease. Examples of chronic inflammatory disease include, but are not limited to, inflammatory bowel diseases such as Crohn's disease and ulcerative colitis, psoriasis, sarcoidois, and rheumatoid arthritis.

Inflammatory bowel diseases such as Crohn's disease and ulcerative colitis are characterized by chronic inflammation and angiogenesis at various sites in the gastrointestinal tract. For example, Crohn's disease occurs as a chronic transmural inflammatory disease that most commonly affects the distal ileum and colon but can also occur in any part of the gastrointestinal tract from the mouth to the anus and perianal area. Patients with Crohn's disease generally have chronic diarrhea associated with abdominal pain, fever, anorexia, weight loss and abdominal swelling. Ulcerative colitis is also a chronic, nonspecific, inflammatory and ulcerative disease arising in the colonic mucosa and is characterized by the presence of bloody diarrhea. These inflammatory bowel diseases are generally caused by chronic granulomatous inflammation throughout the gastrointestinal tract, involving new capillary sprouts surrounded by a cylinder of inflammatory cells. Inhibition of angiogenesis by the pharmaceutical formulations of the present disclosure should inhibit the formation of the sprouts and prevent the formation of granulomas. The inflammatory bowel diseases also exhibit extra intestinal manifestations, such as skin lesions. Such lesions are characterized by inflammation and angiogenesis and can occur at many sites other the gastrointestinal tract. Inhibition of angiogenesis by the lyophilized pharmaceutical compositions of the present disclosure should reduce the influx of inflammatory cells and prevent the lesion formation.

Sarcoidois, another chronic inflammatory disease, is characterized as a multi-system granulomatous disorder. The granulomas of this disease can form anywhere in the body and, thus, the symptoms depend on the site of the granulomas and whether the disease is active. The granulomas are created by the angiogenic capillary sprouts providing a constant supply of inflammatory cells. By using the lyophilized pharmaceutical compositions of the present invention to inhibit angionesis, such granulomas formation can be inhibited. Psoriasis, also a chronic and recurrent inflammatory disease, is characterized by papules and plaques of various sizes. Treatment using the pharmaceutical formulations of the present disclosure can reduce the likelihood of the formation of new blood vessels necessary to maintain the characteristic lesions and provide the patient relief from the symptoms.

Rheumatoid arthritis (RA) is also a chronic inflammatory disease characterized by non-specific inflammation of the peripheral joints. The blood vessels in the synovial lining of the joints can undergo angiogenesis. In addition to forming new vascular networks, the endothelial cells release factors and reactive oxygen species that lead to pannus growth and cartilage destruction. The factors involved in angiogenesis can actively contribute to, and help maintain, the chronically inflamed state of rheumatoid arthritis. Treatment using the pharmaceutical formulations of the present disclosure alone or in conjunction with other anti-RA agents can reduce the likelihood of the formation of new blood vessels necessary to maintain the chronic inflammation and provide the RA patient relief from the symptoms.

In some embodiments, the lyophilized pharmaceutical compositions of the present disclosure can be used for treating diseases associated with abnormal hemoglobin synthesis. The method of treatment can involve administering the pharmaceutical formulations of the present disclosure to a patient suffering from disease associated with abnormal hemoglobin synthesis. Decitabine-containing formulations stimulate fetal hemoglobin synthesis because the mechanism of incorporation into DNA is associated with DNA hypomethylation. Examples of diseases associated with abnormal hemoglobin synthesis include, but are not limited to, sickle cell anemia and β-thalassemia.

In some embodiments, the lyophilized pharmaceutical compositions of the present disclosure can be used to control intracellular gene expression. The method of treatment can involve administering the pharmaceutical formulations of the present disclosure to a patient suffering from a disease associated with abnormal levels of gene expression. DNA methylation is associated with the control of gene expression. Specifically, methylation in or near promoters inhibit transcription while demethylation restores expression. Examples of the possible applications of the described mechanisms include, but are not limited to, therapeutically modulated growth inhibition, induction of apoptosis, and cell differentiation.

In some embodiments, the lyophilized pharmaceutical compositions of the present disclosure can be used in the treatment of patients with genetic mutations associated with tumor hypermethylation such as patients with tumor types which contain the succinate dehydrogenase (SDH) mutation or deficiency which includes patients with non-KIT mutated gastrointestinal stromal tumors (GIST).

Gene activation facilitated by the lyophilized pharmaceutical compositions of the present disclosure can induce differentiation of cells for therapeutic purposes. Cellular differentiation is induced through the mechanism of hypomethylation. Examples of morphological and functional differentiation include, but are not limited to differentiation towards formation of muscle cells, myotubes, cells of erythroid and lymphoid lineages.

Myelodysplastic syndromes (MDS) are heterogeneous clonal hematopoietic stem cell disorders associated with the presence of dysplastic changes in one or more of the hematopoietic lineages, including dysplastic changes in the myeloid, erythroid, and megakaryocytic series. These changes result in cytopenias in one or more of the three lineages. Subjects afflicted with MDS typically develop complications related to anemia, neutropenia (infections), or thrombocytopenia (bleeding). Generally, from about 10% to about 70% of subjects with MDS develop acute leukemia. Representative myelodysplastic syndromes include acute myeloid leukemia, acute promyelocytic leukemia, acute lymphoblastic leukemia, and chronic myelogenous leukemia.

Acute myeloid leukemia (AML) is the most common type of acute leukemia in adults. Several inherited genetic disorders and immunodeficiency states are associated with an increased risk of AML. These include disorders with defects in DNA stability leading to random chromosomal breakage, such as Bloom's syndrome, Fanconi's anemia, Li-Fraumeni kindreds, ataxia-telangiectasia, and X-linked agammaglobulinemia.

Acute promyelocytic leukemia (APML) represents a distinct subgroup of AML. This subtype is characterized by promyelocytic blasts containing the 15; 17 chromosomal translocation. This translocation leads to the generation of a fusion transcript comprising a retinoic acid receptor sequence and a promyelocytic leukemia sequence.

Acute lymphoblastic leukemia (ALL) is a heterogenous disease with distinct clinical features displayed by various subtypes. Reoccurring cytogenetic abnormalities have been demonstrated in ALL. The most common associated cytogenetic abnormality is the 9; 22 translocation leading to development of the Philadelphia chromosome.

In some embodiments, the lyophilized pharmaceutical compositions of the present disclosure can be used to treat an MDS, for example an MDS selected from AML, APML and ALL.

Each of the foregoing therapeutic uses, the lyophilized pharmaceutical compositions of the disclosure can be reconstituted in a suitable solvent as described herein before administration to a subject, e.g. a mammalian subject such as a human patient.

Dosing and Administration.

Doses of lyophilized pharmaceutical compositions of the present disclosure, reconstituted or mixed as necessary with a pharmaceutically acceptable solvent or solvent mixture as described herein can be administered to a subject. Non-limiting examples of methods of administration include subcutaneous injection, intravenous injection, and infusion.

A dose of a formulation contains an amount that is therapeutically-effective for treating a disease. A therapeutically-effective amount of a compound of the present disclosure can be expressed as mg of the compound per kg of subject body mass. In some embodiments, a therapeutically-effective amount is 1-1,000 mg/kg, 1-500 mg/kg, 1-250 mg/kg, 1-100 mg/kg, 1-50 mg/kg, 1-25 mg/kg, or 1-10 mg/kg. In some embodiments, a therapeutically-effective amount is 5 mg/kg, 10 mg/kg, 25 mg/kg, 50 mg/kg, 75 mg/kg, 100 mg/kg, 150 mg/kg, 200 mg/kg, 250 mg/kg, 300 mg/kg, 400 mg/kg, 500 mg/kg, 600 mg/kg, 700 mg/kg, 800 mg/kg, 900 mg/kg, 1,000 mg/kg, about 5 mg/kg, about 10 mg/kg, about 25 mg/kg, about 50 mg/kg, about 75 mg/kg, about 100 mg/kg, about 150 mg/kg, about 200 mg/kg, about 250 mg/kg, about 300 mg/kg, about 400 mg/kg, about 500 mg/kg, about 600 mg/kg, about 700 mg/kg, about 800 mg/kg, about 900 mg/kg, or about 1,000 mg/kg.

A compound described herein can be present in a composition in a range of from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, from about 30 mg to about 35 mg, from about 35 mg to about 40 mg, from about 40 mg to about 45 mg, from about 45 mg to about 50 mg, from about 50 mg to about 55 mg, from about 55 mg to about 60 mg, from about 60 mg to about 65 mg, from about 65 mg to about 70 mg, from about 70 mg to about 75 mg, from about 75 mg to about 80 mg, from about 80 mg to about 85 mg, from about 85 mg to about 90 mg, from about 90 mg to about 95 mg, from about 95 mg to about 100 mg, from about 100 mg to about 125 mg, from about 125 mg to about 150 mg, from about 150 mg to about 175 mg, from about 175 mg to about 200 mg, from about 200 mg to about 225 mg, from about 225 mg to about 250 mg, or from about 250 mg to about 300 mg.

A compound described herein can be present in a composition in an amount of about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 225 mg, about 250 mg, or about 300 mg.

In some embodiments, a therapeutically-effective amount can be administered 1-35 times per week, 1-14 times per week, or 1-7 times per week. In some embodiments, a therapeutically-effective amount can be administered 1-10 times per day, 1-5 times per day, 1 time, 2 times, or 3 times per day.

The lyophilized pharmaceutical compositions described herein can be used either alone or in combination therapy with other chemotherapeutic agents or radiation therapy in the prophylaxis or treatment of a range of proliferative disease states or conditions. Examples of such disease states and conditions are set out above.

The lyophilized pharmaceutical compositions of the present disclosure, whether administered alone, or in combination with anti-cancer agents and therapies such as radiotherapy, can be administered to a subject in need of such administration, for example a human or animal patient, preferably a human.

Examples of chemotherapeutic agents that can be co-administered with the lyophilized pharmaceutical compositions as described herein include but are not limited to topoisomerase I inhibitors; other antimetabolites; tubulin targeting agents; DNA binder and topoisomerase II inhibitors; alkylating agents; monoclonal antibodies; anti-hormones; signal transduction inhibitors; proteasome inhibitors; DNA methyl transferase inhibitors; cytokines; interferons; interleukins; retinoids; chromatin targeted therapies, e.g. HDAC or HAT modulators; T-cell activating agents, including immunomodulating antibodies; cancer vaccines; hormonal agents; plant-derived agents; biologic agents; immunomodulating agents; radiotherapy; and other therapeutic or prophylactic agents; for example agents that reduce or alleviate some of the side effects associated with chemotherapy; for example anti-emetic agents and agents that prevent or decrease the duration of chemotherapy-associated neutropenia and prevent complications that arise from reduced levels of red blood cells or white blood cells, such as erythropoietin (EPO), granulocyte macrophage-colony stimulating factor (GM-CSF), and granulocyte-colony stimulating factor (G-CSF).

In one embodiment, the lyophilized pharmaceutical compositions described herein are used in combination with inhibitors of histone deacetylase (HDAC) to further modulate transcription of genes, e.g., to reestablish transcription of genes silenced by hypermethylation and acetylation of histones, in a synergistic manner.

Inhibitors of HDACs include, but are not limited to, the following structural classes: 1) hydroxamic acids, 2) cyclic peptides, 3) benzamides, and 4) short-chain fatty acids. Examples of hydroxamic acids and hydroxamic acid derivatives, include trichostatin A (TSA), suberoylanilide hydroxamic acid (SAHA), oxamflatin, suberic bishydroxamic acid (SBHA), m-carboxy-cinnamic acid bishydroxamic acid (CBHA), and pyroxamide. TSA was isolated as an antifungi antibiotic and found to be a potent inhibitor of mammalian HDAC. The finding that TSA-resistant cell lines have an altered HDAC evidences that this enzyme is an important target for TSA. Other hydroxamic acid-based HDAC inhibitors, SAHA, SBHA, and CBHA are synthetic compounds that are able to inhibit HDAC at micromolar concentration or lower in vitro or in vivo. These hydroxamic acid-based HDAC inhibitors all possess an essential structural feature: a polar hydroxamic terminal linked through a hydrophobic methylene spacer (e.g. 6 carbon at length) to another polar site, which is attached to a terminal hydrophobic moiety (e.g., benzene ring).

Cyclic peptides used as HDAC inhibitors can be cyclic tetrapeptides. Examples of cyclic peptides include, but are not limited to, trapoxin A, apicidin and FR901228. Trapoxin A is a cyclic tetrapeptide that contains a 2-amino-8-oxo-9, 10-epoxy-decanoyl (AOE) moiety. Apicidin is a fungal metabolite that exhibits potent, broad-spectrum antiprotozoal activity and inhibits HDAC activity at nanomolar concentrations. FR901228 is a depsipeptide that is isolated from *Chromobacterium violaceum*, and has been shown to inhibit HDAC activity at micromolar concentrations.

Examples of benzamides include but are not limited to MS-27-275. Examples of short-chain fatty acids include but are not limited to butyrates (e.g., butyric acid, arginine butyrate and phenylbutyrate (PB)). In addition, depudecin which has been shown to inhibit HDAC at micromolar concentrations can also be used in combination with a composition disclosed herein.

In one embodiment, an alkylating agent is used in combination with the present lyophilized pharmaceutical compositions. Examples of alkylating agents include bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), and platinum compounds (carboplastin and cisplatin).

In some embodiments, the lyophilized pharmaceutical composition described herein can be used in combination with a platinum compound such as cisplatin or carboplatin.

In some embodiments, the lyophilized pharmaceutical composition described herein can be used in combination with a member of the retinoids superfamily such as all-trans-retinol, all-trans-retinoic acid (tretinoin), 13-cis retinoic acid (isotretinoin) and 9-cis-retinoic acid.

In some embodiments, the lyophilized pharmaceutical composition described herein can be used in combination with a hormonal agent such as a synthetic oestrogen (e.g. diethylstibestrol), antiestrogen (e.g. tamoxifen, toremifene, fluoxymesterol and raloxifene), antiandrogen (bicalutamide, nilutamide, flutamide), aromatase inhibitor (e.g., aminoglutethimide, anastrozole and tetrazole), ketoconazole, goserelin acetate, leuprolide, megestrol acetate, and mifepristone.

In some embodiments, the lyophilized pharmaceutical composition described herein can be used in combination with a plant-derived agent such as a vinca alkaloid (e.g., vincristine, vinblastine, vindesine, vinzolidine and vinorelbine), camptothecin (20(S)-camptothecin, 9-nitro-20(S)-camptothecin, and 9-amino-20(S)-camptothecin), a podophyllotoxin (e.g., etoposide (VP-16) and teniposide (VM-26)), and taxane (e.g., paclitaxel and docetaxel).

In some embodiments, the lyophilized pharmaceutical composition described herein can be used in combination with a taxane such as paclitaxel and docetaxel.

In some embodiments, lyophilized pharmaceutical compositions described herein can be used in combination with an anthracycline, such as daunorubicin or idarubicin.

In some embodiments, the lyophilized pharmaceutical composition described herein can be used in combination with a biological agent such as an immuno-modulating protein (e.g. a cytokine), a monoclonal antibody against a tumour antigen, a tumour suppressor gene or a cancer vaccine.

Examples of interleukins that can be used in combination with the lyophilized pharmaceutical composition disclosed herein include, but are not limited to, interleukin 2 (IL-2), and interleukin 4 (IL-4), interleukin 12 (IL-12). Examples of interferons that can be used in conjunction with the lyophilized pharmaceutical composition described herein include, but are not limited to, interferon [alpha], interferon [beta](fibroblast interferon) and interferon [gamma] (fibroblast interferon). Examples of such cytokines include, but are not limited to erythropoietin (epoietin), granulocyte-CSF (filgrastim), and granulocyte, macrophage-CSF (sargramostim). Immuno-modulating agents other than cytokines include, but are not limited to *bacillus* Calmette-Guerin, levamisole, and octreotide.

Examples of monoclonal antibodies against tumour antigens that can be used in conjunction with the lyophilized pharmaceutical composition described herein include, but are not limited to, HERCEPTIN® (Trastruzumab), RITUXAN® (Rituximab), MYLOTARG® (anti-CD33), and CAMPATH® (anti-CD52).

In some embodiments, the lyophilized pharmaceutical composition described herein can be used in combination with a cancer vaccine, for example a cancer vaccine selected from a CTA cancer vaccine, such as a vaccine based on a CTA antigen selected from: NY-ESO-1, LAGE-1, MAGE-A1, -A2, -A3, -A4, -A6, -A10, -A12, CT7, CT10, GAGE1-6, GAGE 1-2, BAGE, SSX1-5, SSX 2, HAGE, PRAME, RAGE-1, XAGE-1, MUC2, MUC5B and HMW-MAA. Non-limiting examples of CTA vaccines include those based on MAGE-A3 (for example recMAGE-A3), NY-ESO-1 and PRAME.

In some embodiments, the lyophilized pharmaceutical composition described herein can be used in combination with a T-cell activating agent, for example a T-cell activating agent which is an antibody (optionally a mAb), for example selected from: (a) a CD137 agonist; (b) a CD40 agonist; (c) an OX40 agonist; (d) a PD-1 mAb; (e) a PD-L1 mAb; (f) a CTLA-4 mAb; and (g) combinations of (a)-(f). In some embodiments, the ancillary therapeutic component is Tremelimumab or Ipilimumab.

In some embodiments, the lyophilized pharmaceutical composition described herein can be used in combination with carboplatin for the treatment of platinum-resistant recurrent ovarian cancer.

In some embodiments, the lyophilized pharmaceutical composition described herein can be used in the treatment of hepatocellular carcinoma (e.g. post sorafenib failures).

In some embodiments, the lyophilized pharmaceutical composition described herein can be used in combination with irinotecan for the treatment of metastatic colon cancer.

In some embodiments, the lyophilized pharmaceutical composition described herein can be used in combination with 5-fluorouracil (5-FU), leuocovorin, oxaliplatin for the treatment of metastatic colon cancer.

In some embodiments, the lyophilized pharmaceutical composition described herein can be used in combination with cytarabine and fludarabine for the treatment of pediatric relapsed/refractory AML.

In some embodiments, the lyophilized pharmaceutical composition described herein can be used in combination with a JAK2 inhibitor for the treatment of myoproliferative neoplasms.

The lyophilized pharmaceutical composition described herein and any other therapeutic agents can be presented separately or presented together in a pharmaceutical package, kit, or patient pack.

The lyophilized pharmaceutical composition described herein and combinations with other therapeutic agents or radiation therapies as described above can be administered over a prolonged term to maintain beneficial therapeutic effects or can be administered for a short period only. Alternatively, the compositions and combinations can be administered in a pulsatile or continuous manner.

The lyophilized pharmaceutical composition described herein can be administered in an effective amount, i.e. an amount that is effective to bring about the desired therapeutic effect either alone (in monotherapy) or in combination with one or more chemotherapeutic agents or radiation therapy. For example, the effective amount can be a quantity of compound which, when administered to a subject suffering from cancer, slows tumour growth, ameliorates the symptoms of the disease and/or increases longevity.

The amount of the lyophilized pharmaceutical composition described herein administered to the subject can depend on the type and severity of the disease or condition and on the characteristics of the subject, such as general health, age, sex, body weight and tolerance to drugs. The skilled person is able to determine appropriate dosages depending on these and other factors.

Purity of Compounds Disclosed Herein.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

Impurities in the Lyophilized Pharmaceutical Compositions Described Herein.

Impurities can be formed by, for example, epimerization of the anomeric stereocenter in the decitabine fragment, synthesis by-products, degradation products, opening of the triazine ring with water, opening of the triazine ring with water followed by basic cleavage of the intermediate formamide, formation of a protected dimer and subsequent cleavage of the protecting groups, or incomplete deprotection of synthetic intermediates.

Lyophilized pharmaceutical compositions of the disclosure can comprise impurities, for example, a nucleotide, a nucleoside, a compound comprising a ribose core, a compound comprising a deoxyribose core, a compound comprising a deoxyribonucleoside, or a compound comprising a deoxyadenosine, wherein an impurity, for example, is not a compound of formula (1). In some embodiments, lyophilized pharmaceutical compositions of the disclosure comprise a compound comprising deoxyribose, a nitrogenous base (e.g., adenine), and a phosphate group, wherein an impurity, for example, is not a compound of formula (1).

Non-limiting examples of impurities in the lyophilized compositions of the disclosure include a compound of formula (2):

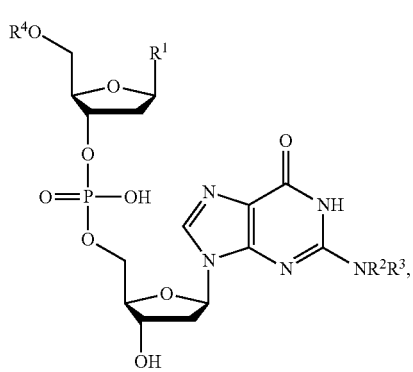

Formula (2)

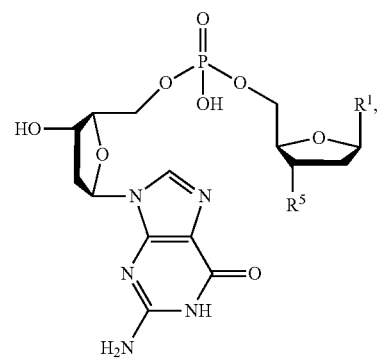

Formula (4)

or a pharmaceutically acceptable salt thereof, wherein the compound of formula (2) is not a compound of formula (1), wherein:

$R^1$ is a heteroaryl or a carbamide, each of which is independently substituted or unsubstituted; each $R^2$ and $R^3$ is independently alkyl, which is substituted or unsubstituted; or hydrogen; and $R^4$ is hydrogen or an acyl group, each of which is independently substituted or unsubstituted.

In some embodiments, $R^1$ is a carbamide that is substituted. In some embodiments, $R^1$ is a carbamide substituted with methane diamine. In some embodiments, $R^1$ is a carbamide substituted with N-(aminomethyl) formamide. In some embodiments, $R^1$ is heteroaryl. In some embodiments, $R^1$ is 4-amino-2H-1$\lambda^2$,3,5-triazin-2-one.

In some embodiments, each $R^2$ and $R^3$ is independently hydrogen. In some embodiments, $R^2$ is H and $R^3$ is alkyl substituted with hydroxy. In some embodiments, $R^2$ is H and $R^3$ is alkyl substituted with alkoxy. In some embodiments, $R^2$ is H and $R^3$ is methyl substituted with methoxy. In some embodiments, $R^4$ is hydrogen. In some embodiments, $R^4$ is an acyl group, such as acetyl.

In some embodiments, impurities in the lyophilized compositions of the disclosure includes a compound of formula (3):

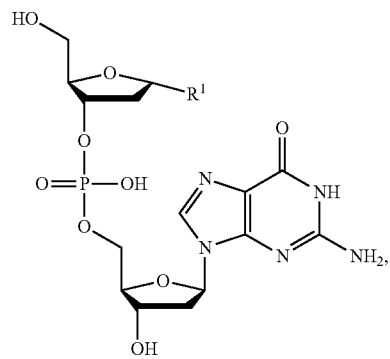

Formula (3)

or a pharmaceutically acceptable salt thereof, wherein $R^1$ is heteroaryl or a carbamide, each of which is independently substituted or unsubstituted.

In some embodiments, $R^1$ is heteroaryl, for example, 4-amino-2H-1$\lambda^2$,3,5-triazin-2-one. In some embodiments, $R^1$ is a substituted carbamide, for example, carbamide substituted with methane diamine.

In some embodiments, impurities in the lyophilized compositions of the disclosure include a compound of formula (4):

or a pharmaceutically acceptable salt thereof, wherein:

$R^1$ is heteroaryl, which is substituted or unsubstituted; and $R^5$ is hydroxy or a nucleotide.

In some embodiments, $R^1$ is heteroaryl, for example, 4-amino-2H-1$\lambda^2$,3,5-triazin-2-one or 2-amino-9$\lambda^2$-purin-6 (1H)-one. In some embodiments, $R^5$ is a hydroxyl group. In some embodiments, $R^5$ is a nucleotide, for example, a nucleotide of the formula:

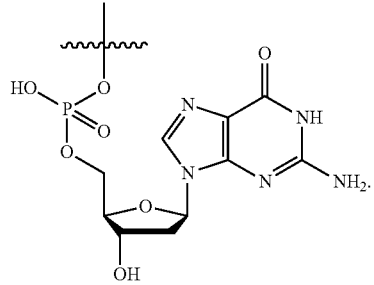

In some embodiments an impurity is a compound of the formula:

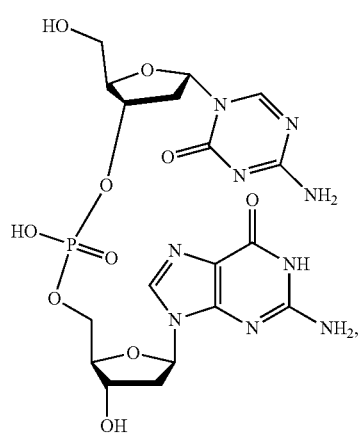

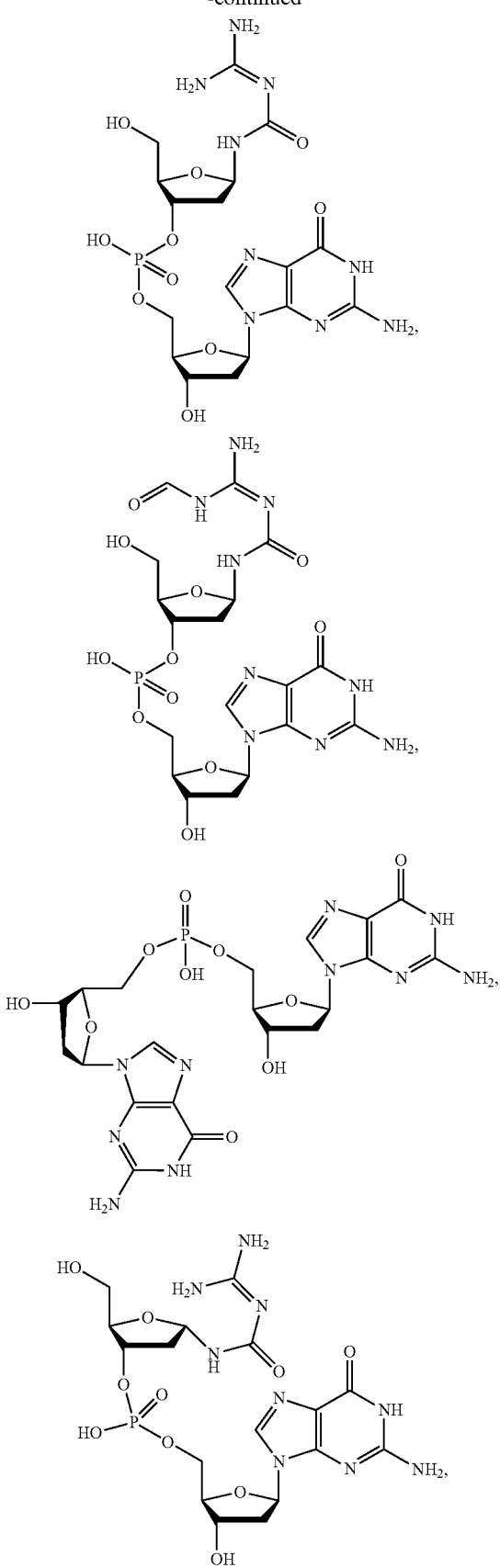
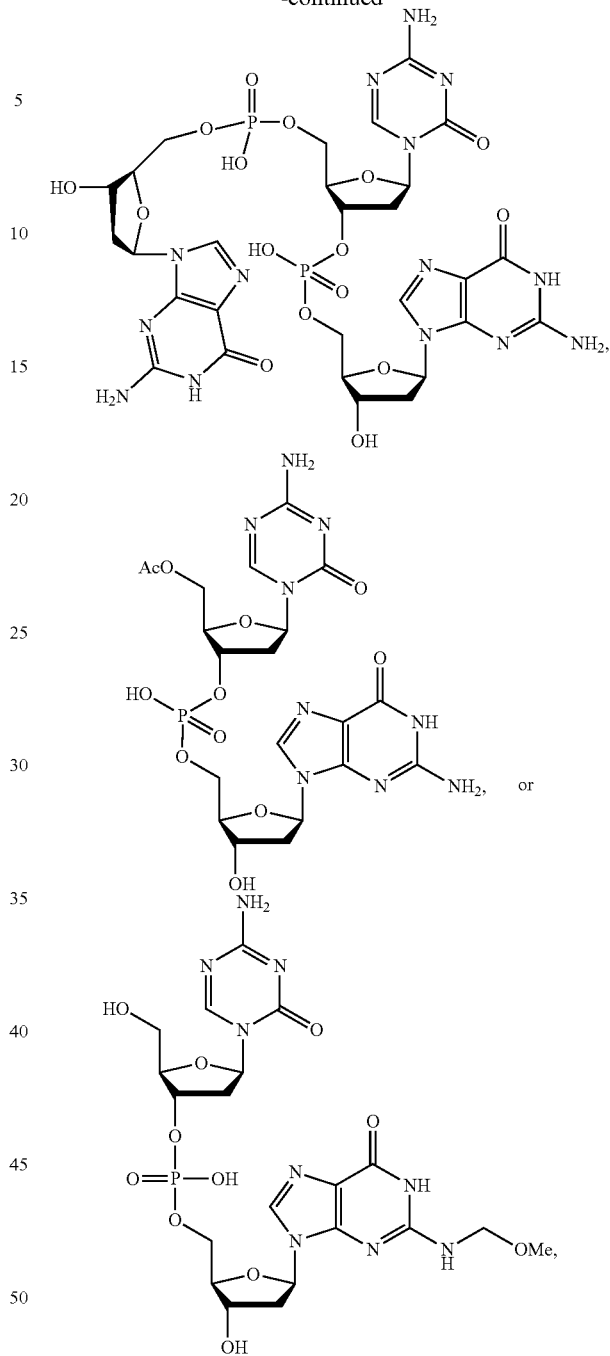

or a pharmaceutically acceptable salt thereof.

Impurities can be present in lyophilized compositions in an amount of up to about 0.01%, up to about 0.02%, up to about 0.03%, up to about 0.04%, up to about 0.05%, up to about 0.06%, up to about 0.07%, up to about 0.08%, up to about 0.09%, up to about 0.1%, up to about 0.12%, up to about 0.14%, up to about 0.16%, up to about 0.18%, up to about 0.2%, up to about 0.22%, up to about 0.24%, up to about 0.26%, up to about 0.28%, up to about 0.3%, up to about 0.32%, up to about 0.34%, up to about 0.36%, up to about 0.38%, up to about 0.4%, up to about 0.42%, up to about 0.44%, up to about 0.46%, up to about 0.48%, or up to about 0.5% of the lyophilized composition. In some embodiments, impurities can be present in lyophilized compositions in an amount of about 0.05% to about 0.1%. In some embodiments, impurities can be present in lyophilized compositions in an amount of about 0.05% to about 0.2%. In some embodiments, impurities can be present in lyophilized compositions in an amount of about 0.05% to about 0.3%. In some embodiments, impurities can be present in lyophilized compositions in an amount of about 0.05% to about 0.35%.

In some embodiments, impurities can be present in lyophilized compositions in an amount of about 0.05%. In some embodiments, impurities can be present in lyophilized compositions in an amount of about 0.1%. In some embodiments, impurities can be present in lyophilized compositions in an amount of about 0.15%.

Lyophilized compositions can comprise more than one impurity. For example, a lyophilized composition can comprise 1, 2, 3, 4, 5, 6, 7, 8, 9, or 10 impurities. In some embodiments, a lyophilized composition can comprise 3 impurities. In some embodiments, a lyophilized composition can comprise 4 impurities. In some embodiments, a lyophilized composition can comprise 5 impurities. In some embodiments, a lyophilized composition can comprise 6 impurities. In some embodiments, a lyophilized composition can comprise 7 impurities.

The ratio of the compound of formula (1) to an impurity in a pharmaceutical composition of the present disclosure can be, for example, about 20,000:about 1, about 19,000:about 1, about 18,000:about 1, about 17,000:about 1, about 16,000:about 1, about 15,000:about 1, about 14,000:about 1, about 13,000:about 1, about 12,000:about 1, about 11,000:about 1, about 10,000:about 1, about 9,900:about 1, about 9,800:about 1, about 9,700:about 1, about 9,600:about 1, about 9,500:about 1, about 9,400:about 1, about 9,300:about 1, about 9,200:about 1, about 9,100:about 1, about 9,000:about 1, about 8,900:about 1, about 8,800:about 1, about 8,700:about 1, about 8,600:about 1, about 8,500:about 1, about 8,400:about 1, about 8,300:about 1, about 8,200:about 1, about 8,100:about 1, about 8,000:about 1, about 7,900:about 1, about 7,800:about 1, about 7,700:about 1, about 7,600:about 1, about 7,500:about 1, about 7,400:about 1, about 7,300:about 1, about 7,200:about 1, about 7,100:about 1, about 7,000:about 1, about 6,900:about 1, about 6,800:about 1, about 6,700:about 1, about 6,600:about 1, about 6,500:about 1, about 6,400:about 1, about 6,300:about 1, about 6,200:about 1, about 6,100:about 1, about 6,000:about 1, about 5,900:about 1, about 5,800:about 1, about 5,700:about 1, about 5,600:about 1, about 5,500:about 1, about 5,400:about 1, about 5,300:about 1, about 5,200:about 1, about 5,100:about 1, about 5,000:about 1, about 4,900:about 1, about 4,800:about 1, about 4,700:about 1, about 4,600:about 1, about 4,500:about 1, about 4,400:about 1, about 4,300:about 1, about 4,200:about 1, about 4,100:about 1, about 4,000:about 1, about 3,900:about 1, about 3,800:about 1, about 3,700:about 1, about 3,600:about 1, about 3,500:about 1, about 3,400:about 1, about 3,300:about 1, about 3,200:about 1, about 3,100:about 1, about 3,000:about 1, about 2,900:about 1, about 2,800:about 1, about 2,700:about 1, about 2,600:about 1, about 2,500:about 1, about 2,400:about 1, about 2,300:about 1, about 2,200:about 1, about 2,100:about 1, about 2,000:about 1, about 1,900:about 1, about 1,800:about 1, about 1,700:about 1, about 1,600:about 1, about 1,500:about 1, about 1,400:about 1, about 1,300:about 1, about 1,200:about 1, about 1,100:about 1, about 1,000:about 1, about 990:about 1, about 980:about 1, about 970:about 1, about 960:about 1, about 950:about 1, about 800:about 1, about 700:about 1, about 600:1, about 500:about 1, about 400:about 1, about 300:about 1, about 200:about 1, about 100:about 1, about 95:about 1, about 90:about 1, about 85:about 1, about 80:about 1, about 75:about 1, about 70:about 1, about 65:about 1, about 60:about 1, about 55:about 1, about 50:about 1, about 45:about 1, about 40:about 1, about 35:about 1, about 30:about 1, about 25:about 1, about 20:about 1, about 19:about 1, about 18:about 1, about 17:about 1, about 16:about 1, about 15:about 1, about 14:about 1, about 13:about 1, about 12:about 1, about 11:about 1, or about 10:about 1.

The amount of an impurity in a composition of the present disclosure can be, for example, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, or about 100% by mass of a compound of formula (1).

The amount of Impurity 1 in a composition of the present disclosure can be, for example, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5%, by mass of a compound of formula (1). The amount of Impurity 1 in a composition of the present disclosure can range from, for example, about 0.01% to about 0.02%, 0.01% to about 0.03%, about 0.01% to about 0.04%, about 0.01% to about 0.05%, about 0.01% to about 0.08%, about 0.01% to about 0.1%, about 0.02% to about 0.03%, about 0.02% to about 0.04%, about 0.02% to about 0.05%, about 0.02% to about 0.08%, about 0.02% to about 0.1%, about 0.03% to about 0.04%, about 0.03% to about 0.05%, about 0.03% to about 0.06%, about 0.03% to about 0.1%, about 0.05% to about 0.1%, about 0.1% to about 0.5%, about 0.5% to about 1%, about 1% to about 1.5%, about 1.5% to about 2%, about 2% to about 2.5%, about 2.5% to about 3%, about 3% to about 3.5%, about 3.5% to about 4%, about 4% to about 4.5%, and about 4.5% to about 5%. In some embodiments, the amount of Impurity 1 in a composition disclosed herein is less than or equal to about 0.05%.

The amount of Impurity 2 in a composition of the present disclosure can be, for example, about 0.05%, about 0.06%, about 0.07%, about 0.08%, about 0.09%, about 0.1%, about 0.11%, about 0.12%, about 0.13%, about 0.14%, about 0.15%, about 0.2%, about 0.21%, about 0.22%, about 0.23%, about 0.24%, about 0.25%, about 0.26%, about 0.27%, about 0.28%, about 0.29%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5%, by mass of a compound of formula (1). The amount of Impurity 1 in a composition of the present disclosure can range from, for example, about 0.05% to about 0.06%, about 0.05% to about 0.07%, about 0.05% to about 0.08%, about 0.05% to about 0.09%, about 0.05% to about 0.1%, about 0.1% to about 0.2%, about 0.1% to about 0.5%, about 0.2% to about 0.3%, about 0.5% to about 1%, about 1% to about 1.5%, about 1.5% to about 2%, about 2% to about 2.5%, about 2.5% to about 3%, about 3% to about 3.5%, about 3.5% to about 4%, about 4% to about 4.5%, and about 4.5% to about 5%.

The amount of Impurity 3 in a composition of the present disclosure can be, for example, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5%, by mass of a compound of formula (1). The amount of Impurity 1 in a composition of the present disclosure can range from, for example, about 0.01% to about 0.02%, 0.01% to about 0.03%, about 0.01% to about 0.04%, about 0.01% to about 0.05%, about 0.01% to about 0.08%, about 0.01% to about 0.1%, about 0.02% to about 0.03%, about 0.02% to about 0.04%, about 0.02% to about 0.05%, about 0.02% to about 0.08%, about 0.02% to about 0.1%, about 0.03% to about 0.04%, about 0.03% to about 0.05%, about 0.03% to about 0.06%, about 0.03% to about 0.1%, about 0.05% to about 0.1%, about 0.1% to about 0.5%, about 0.5% to about 1%, about 1% to about 1.5%, about 1.5% to about 2%, about 2% to about 2.5%, about 2.5% to about 3%, about 3% to about 3.5%, about 3.5% to about 4%, about 4% to about 4.5%, and about 4.5% to about 5%. In some embodiments, the amount of Impurity 3 in a composition disclosed herein is less than or equal to about 0.05%. In some embodiments, the amount of Impurity 3 in a composition disclosed herein is about 0.08%.

The amount of Impurity 4 in a composition of the present disclosure can be, for example, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5%, by mass of a compound of formula (1). The amount of Impurity 1 in a composition of the present disclosure can range from, for example, about 0.01% to about 0.02%, 0.01% to about 0.03%, about 0.01% to about 0.04%, about 0.01% to about 0.05%, about 0.01% to about 0.08%, about 0.01% to about 0.1%, about 0.02% to about 0.03%, about 0.02% to about 0.04%, about 0.02% to about 0.05%, about 0.02% to about 0.08%, about 0.02% to about 0.1%, about 0.03% to about 0.04%, about 0.03% to about 0.05%, about 0.03% to about 0.06%, about 0.03% to about 0.1%, about 0.05% to about 0.1%, about 0.1% to about 0.5%, about 0.5% to about 1%, about 1% to about 1.5%, about 1.5% to about 2%, about 2% to about 2.5%, about 2.5% to about 3%, about 3% to about 3.5%, about 3.5% to about 4%, about 4% to about 4.5%, and about 4.5% to about 5%. In some embodiments, the amount of Impurity 3 in a composition disclosed herein is less than or equal to about 0.05%. In some embodiments, the amount of Impurity 4 in a composition disclosed herein is about 0.06%.

The amount of Impurity 5 in a composition of the present disclosure can be, for example, about 0.05%, about 0.06%, about 0.07%, about 0.08%, about 0.09%, about 0.1%, about 0.11%, about 0.12%, about 0.13%, about 0.14%, about 0.15%, about 0.2%, about 0.21%, about 0.22%, about 0.23%, about 0.24%, about 0.25%, about 0.26%, about 0.27%, about 0.28%, about 0.29%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5%, by mass of a compound of formula (1). The amount of Impurity 1 in a composition of the present disclosure can range from, for example, about 0.05% to about 0.06%, about 0.05% to about 0.07%, about 0.05% to about 0.08%, about 0.05% to about 0.09%, about 0.05% to about 0.1%, about 0.1% to about 0.2%, about 0.1% to about 0.5%, about 0.2% to about 0.3%, about 0.5% to about 1%, about 1% to about 1.5%, about 1.5% to about 2%, about 2% to about 2.5%, about 2.5% to about 3%, about 3% to about 3.5%, about 3.5% to about 4%, about 4% to about 4.5%, and about 4.5% to about 5%.

The amount of Impurity 6 in a composition of the present disclosure can be, for example, about 0.05%, about 0.06%, about 0.07%, about 0.08%, about 0.09%, about 0.1%, about 0.11%, about 0.12%, about 0.13%, about 0.14%, about 0.15%, about 0.2%, about 0.21%, about 0.22%, about 0.23%, about 0.24%, about 0.25%, about 0.26%, about 0.27%, about 0.28%, about 0.29%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, or about 5%, by mass of a compound of formula (1). The amount of Impurity 1 in a composition of the present disclosure can range from, for example, about 0.05% to about 0.06%, about 0.05% to about 0.07%, about 0.05% to about 0.08%, about 0.05% to about 0.09%, about 0.05% to about 0.1%, about 0.1% to about 0.2%, about 0.1% to about 0.5%, about 0.2% to about 0.3%, about 0.5% to about 1%, about 1% to about 1.5%, about 1.5% to about 2%, about 2% to about 2.5%, about 2.5% to about 3%, about 3% to about 3.5%, about 3.5% to about 4%, about 4% to about 4.5%, and about 4.5% to about 5%.

Non-limiting examples of methods that can be used to identify impurities of the present disclosure include high-performance liquid chromatography (HPLC), mass spectrometry (MS), Matrix Assisted Laser Desorption Ionization Time-of-Flight (MALDI-TOF), electrospray ionization Time-of-flight (ESI-TOF), gas chromatography-mass spectrometry (GC-MS), liquid chromatography-mass spectrometry (LC-MS), and two-dimensional gel electrophoresis.

HPLC can be used to identify impurities using high pressure to separate components of a mixture through a packed column of solid adsorbent material, denoted the stationary phase. The sample components can interact differently with the column based upon the pressure applied to the column, material used in stationary phase, size of particles used in the stationary phase, the composition of the solvent used in the column, and the temperature of the column. The interaction between the sample components and the stationary phase can affect the time required for a component of the sample to move through the column. The time required for component to travel through the column from injection point to elution is known as the retention time.

Upon elution from the column, the eluted component can be detected using a UV detector attached to the column. The wavelength of light at which the component is detected, in combination with the component's retention time, can be used to identify the component. Further, the peak displayed by the detector can be used to determine the quantity of the component present in the initial sample. Wavelengths of light that can be used to detect sample components include, for example, about 200 nM, about 225 nm, about 250 nm, about 275 nm, about 300 nm, about 325 nm, about 350 nm, about 375 nm, and about 400 nm.

Mass spectrometry (MS) can also be used to identify impurities of a compound of the present disclosure. To prepare samples for MS analysis, the samples, containing the proteins of interest, are digested by proteolytic enzymes into smaller peptides. The enzymes used for cleavage can be, for example, trypsin, chymotrypsin, glutamyl endopeptidase, Lys-C, and pepsin. The samples can be injected into a mass spectrometer. Upon injection, all or most of the impurities can be ionized and detected as ions on a spectrum according to the mass to charge ratio created upon ionization. The mass to charge ratio can then be used to determine the impurities present in the sample.

The present disclosure provides several embodiments of pharmaceutical formulations that provide advantages in stability, administration, efficacy, and modulation of formulation viscosity. Any embodiments disclosed herein can be used in conjunction or individually. For example, any pharmaceutically-acceptable excipient, method, technique, solvent, or compound disclosed herein can be used together with any other pharmaceutically-acceptable excipient, method, technique, solvent, or compound disclosed herein to achieve any therapeutic result. Compounds, excipients, and other formulation components can be present at any amount, ratio, or percentage disclosed herein in any such formulation, and any such combination can be used therapeutically for any purpose described herein and to provide any viscosity described herein.

EXAMPLES

Example 1. Preparation of a Lyophilized Formulation of a Sodium Salt of the Compound of Formula (1)

The sodium salt of the compound of formula (1) was dissolved in DMSO at a defined concentration using an overhead mixer in an appropriately sized stainless steel (SS) vessel. Upon complete solubilization of the drug in DMSO, samples of the bulk solution were tested using a UV or HPLC in-process method to determine that the amount of the sodium salt of the compound of formula 1 was within 95-105% of the target concentration. The bulk solution was filtered through a series of two pre-sterilized 0.2 micron sterilizing filters that were DMSO-compatible, and collected into a 2 L SS surge vessel. The filtration rate was continuously adjusted by visual monitoring of quantity available for filling in the surge vessel. One gram aliquots of the filtered bulk solution were then filled into 5 cc depyrogenated, clear glass vials. Each vial was automatically and partially stoppered on the fill line with a fluoropolymer coated, chlorobutyl rubber lyo stopper that was pre-sterilized. The product vials were transferred to a lyophilizer under aseptic transfer conditions for initiation of a lyophilization cycle. The lyophilizer used was a pilot scale lyophilizer, Lyobeta 35, IMA-Telstar, which has 1.02 m$^2$ of chamber space, an ice capacity of 35 kg, 22 kg/24 hr for condenser capacity.

The general lyophilization cycle for a compound of Formula (1) was:
1. The shelves were controlled at a target setpoint of 20° C. until the product was loaded onto the shelf. The temperature was held for 1 hour to allow all the product samples to equilibrate at the target temperature.
2. The shelves were chilled to a target shelf setpoint of −45° C. at an average controlled rate of 30° C./hour. The target shelf setpoint was held for 1 hour to allow all the product to equilibrate at the target temperature and for complete solidification.
3. The shelves were warmed at an average controlled rate of 30° C./hour to a target shelf temperature setpoint of 0° C. The target shelf was held at the setpoint for 2 hours to allow all the product samples to anneal at the target temperature.
4. The shelves were chilled to a target shelf setpoint of −45° C. at an average controlled rate of 30° C./hour. The target shelf setpoint was held for 2 hours to allow all the product samples to equilibrate at the target temperature and for complete solidification.
5. The condenser was chilled to below −40° C. and the chamber was evacuated to the target pressure. The target shelf setpoint was held for an additional 4 hours to allow any unfrozen DMSO to vaporize.
6. The chamber pressure was controlled at the target setpoint to allow the DMSO to sublime.
7. The shelves were warmed at an average controlled rate of 30° C./hour to a target shelf temperature setpoint of −6° C., and controlled at the target shelf setpoint for 80.5 hours until all the DMSO had sublimed.
8. The shelves were warmed to a target shelf temperature setpoint of 40° C. at an average controlled rate, and held at the target shelf setpoint to lower the residual DMSO levels.

9. The shelves were chilled to a target setpoint of 20° C. for unloading. The chamber pressure was raised to 14.7±0.7 PSIA by bleeding filtered Nitrogen, NF into the chamber. The vials were stoppered and unloaded.

The specific lyophilization parameters used for this study are provided in TABLE 1 below:

TABLE 1

| Step | Shelf Temp. Setpoint (° C.) | Soak Time (hours) | Ramping Rate (° C./hour) | Pressure Set point |
|---|---|---|---|---|
| Loading | 20 | 1 | | Evacuate to 12 PSIA to ensure chamber is airtight |
| | | | 30 | |
| Freezing | −45 | 1 | | |
| | | | 30 | |
| Annealing | 0 | 2 | | |
| | | | 30 | |
| Freezing | −45 | 2 | | |
| | −45 | 4 | | 20 microns |
| Primary Drying | | | 30 | |
| | −6 | 80.5 | | |
| Secondary Drying | 55 | 15 | 12 | 10 microns |
| Stoppering | | | 30 | |
| | 20 | | | 14.7 PSIA |

Figure 2:
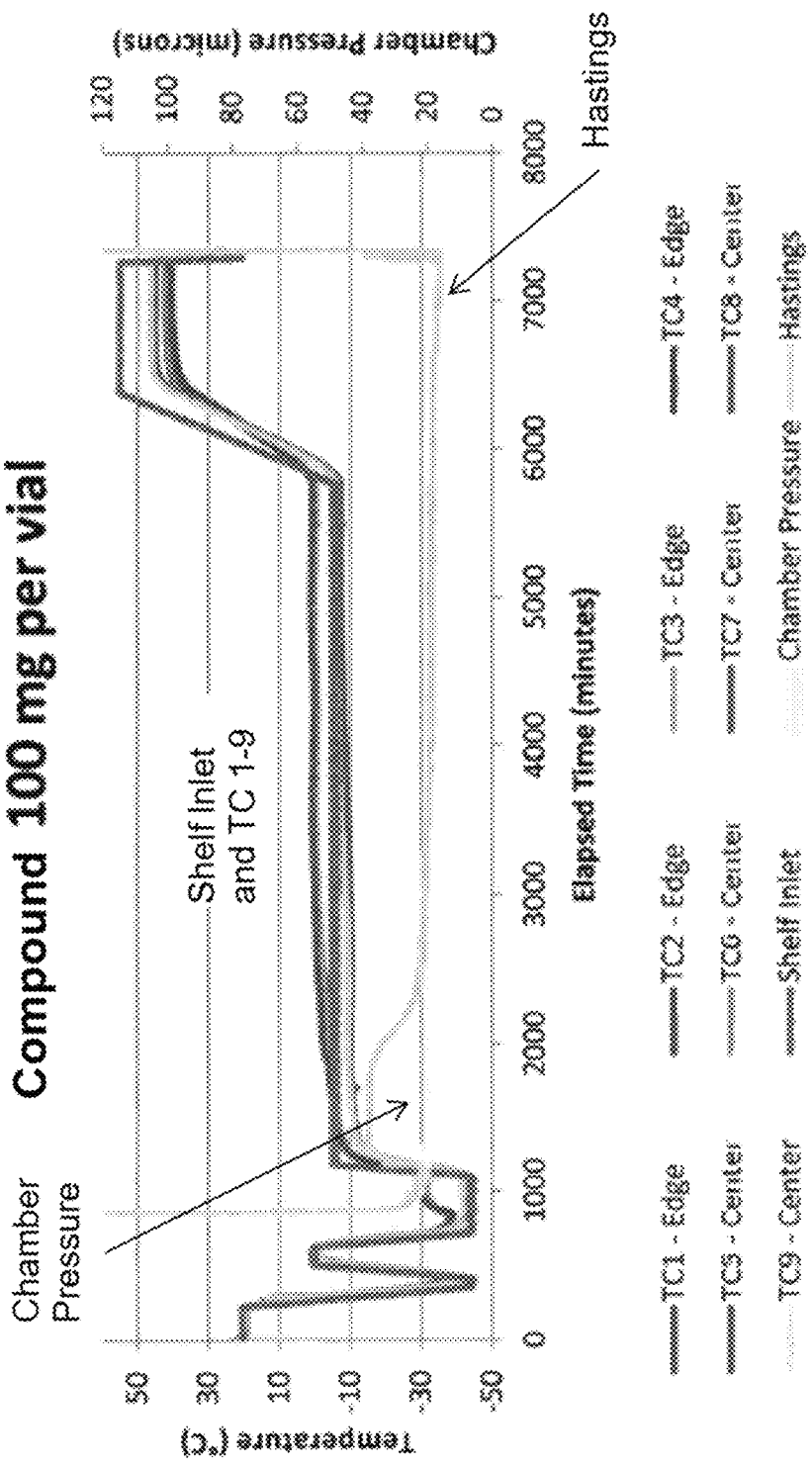
FIG. 2 depicts the lyophilization parameters for a target lyophilization process described herein.

The thermocouple and pressure results of the foregoing lyophilization cycle of TABLE 1 are shown in FIG. 2.

The summary of product temperatures at equilibrium of the foregoing lyophilization cycle parameters are show in TABLE 2 below:

TABLE 2

| Step | Target Shelf Temperature (° C.) | Product Temperatures[1] (° C.) Average (Min to Max) | |
|---|---|---|---|
| | | Center (T/C 5-9) | Edge (T/C 1-4) |
| Loading | 20 | 20 (19.8 to 20.3) | 19.7 (19.6 to 20) |
| Freeze | −45 | −41.7 (−42.7 to −40.5) | −37 (−38.2 to −36.2) |
| Annealing | 0 | 0 (−0.1 to 0.1) | 0.5 (0.5 to 0.6) |
| Freeze[2] | −45 | −43 (−43.5 to −42.4) | −38.9 (−39.4 to −38.4) |
| Freeze | −45 | −41.7 (−42.4 to −41.3) | −30.7 (−31.9 to −29.7) |
| Primary Drying | −6 | −6.3 (−7.1 to −5.7) | 0.1 (−0.2 to 0.7) |
| "Break" | — | −9.6 (−10.2 to −9.2) | −4 (−5.1 to −3.3) |
| Secondary Drying | 55 | 45.8 (45.1 to 46.6) | 41.5 (40.7 to 42.3) |

[1]Product Temperatures indicate temperature at end of segment.
[2]Indicates product temperatures immediately prior to evacuation.

A summary of the product break temperatures are shown below in TABLE 3.

TABLE 3

| Center | | | Edge | | |
|---|---|---|---|---|---|
| Thermo-couple | Temperature (° C.) | Time (hours) | Thermo-couple | Temperature (° C.) | Time (hours) |
| 5-center | −9.2 | 27.8 | 1-edge | −3.3 | 20.2 |
| 6-center | −9.6 | 22.8 | 2-edge | −3.5 | 19 |
| 7-center | −10.2 | 29.8 | 3-edge | −5.1 | 10.2 |
| 8-center | −9.5 | 27.4 | 4-edge | −4 | 11.1 |

TABLE 3-continued

| Center | | | Edge | | |
|---|---|---|---|---|---|
| Thermo-couple | Temperature (° C.) | Time (hours) | Thermo-couple | Temperature (° C.) | Time (hours) |
| 9-center | −9.5 | 23.5 | Average | −4 | 15.1 |
| Average | −9.6 | 26.3 | Minimum | −5.1 | 10.2 |
| Minimum | −10.2 | 22.8 | Maximum | −3.3 | 20.2 |
| Maximum | −9.2 | 29.8 | | | |

Figure 3:
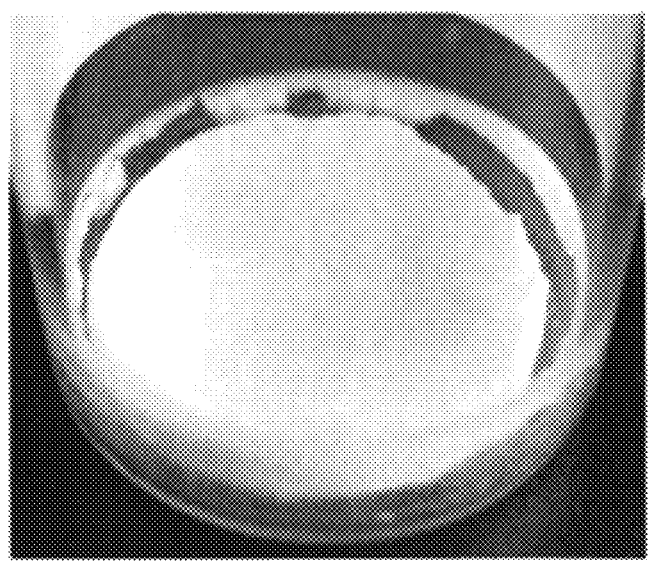
FIG. 3 provides a top view of a lyophilized product of a target lyophilization process described herein.

After lyophilization, the product appeared as a dense, white cake as shown in FIG. 3. The original fill height was 5-6 mm, while the product height was 4 mm with uniform shrinkage observed around the sides of 1 mm. The top of the cake appeared matte with areas of sheen while the sides and bottom appeared sheen. The top of the cake was concave and textured with striations and cracks. Upon inversion, the cake remained intact and moved to the top of the vial. Upon jarring, the cake moved to the top of the vial and broke apart into fragments and powder. A minimal amount of residual material as a thick, white film was present around the original fill height.

Reconstitution was performed by extruding 1 mL of diluent into each vial using a vial adapter or syringe and allowing the vials to sit undisturbed until clear. All the samples resulted in clear and colorless solutions. Due to the long reconstitution times, reconstitution times are reported in minutes for this study as shown in TABLE 4 below:

TABLE 4

| | Recon Time (min) | Turbidity (NTU) |
|---|---|---|
| Center | 25 | (0.92, 0.31, 2.6) |
| Edge | 25 | (1.7, 0.32, 0.64) |

Figure 4:
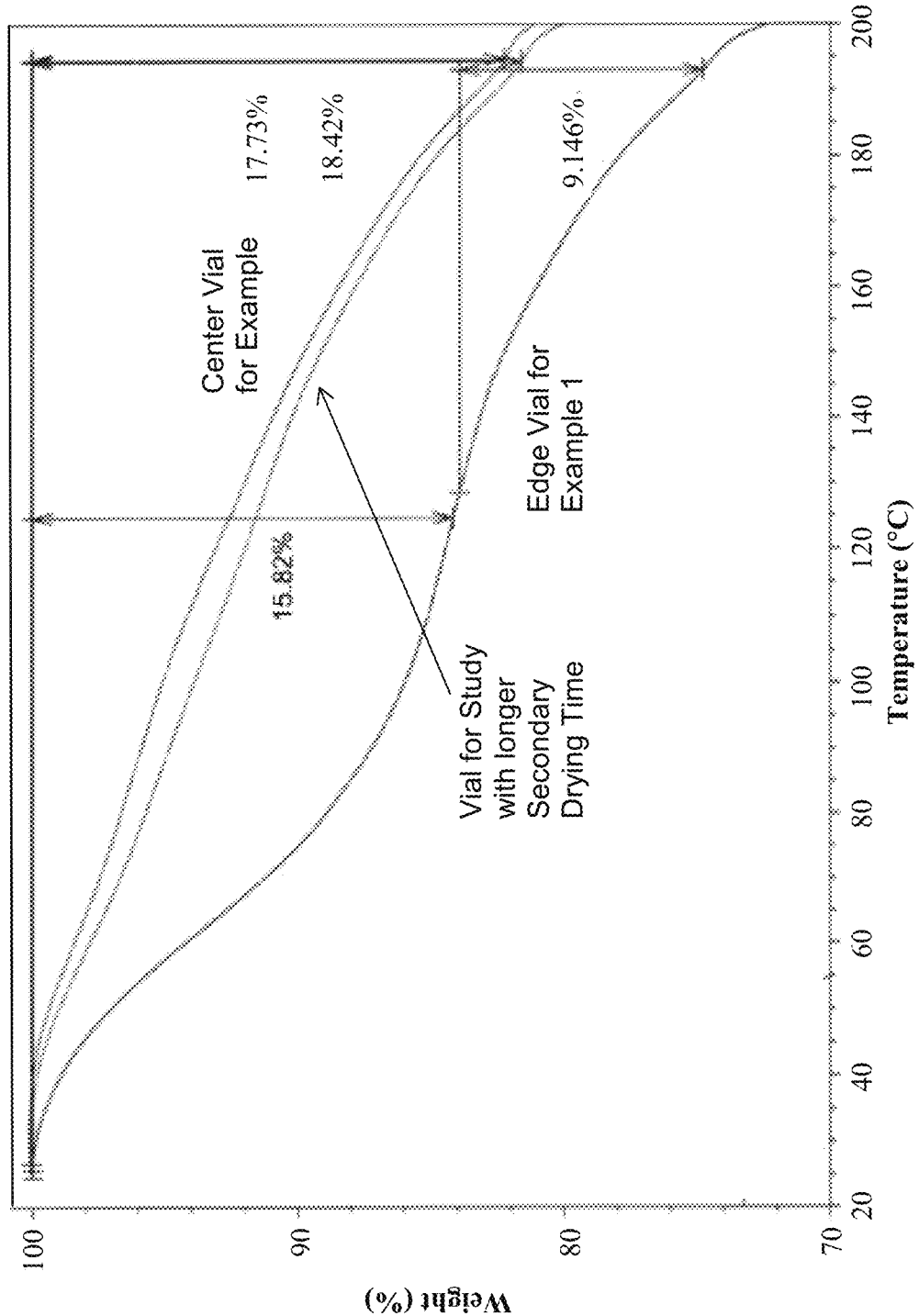
FIG. 4 provides an overlay of differential scanning calorimetry and thermogravimetric analysis thermograms of a target lyophilization process described herein.

FIG. 4 provides an overlay of the TGA results of the present lyophilization and a study with a longer secondary drying time. TGA results of the present lyophilization study showed some variability from 18% w/w to 25% w/w mass loss, while the one vial tested from the study with a longer secondary drying time had a weight loss of 18%.

DMSO amounts of the two lyophilization cycles are shown in TABLE 5 below:

TABLE 5

| Vial | Injection | Study 1 | Study 2 |
|---|---|---|---|
| 1 | 1 | 22.9 | 26.4 |
| | 2 | 22.3 | 27.4 |
| 2 | 1 | 22.5 | 23.1 |
| | 2 | 22.7 | 24.1 |
| 3 | 1 | 25.1 | 22.5 |
| | 2 | 24.9 | 23.9 |
| | Average | 23.4 | 24.6 |

Example 2: Full Load Confirmation Study of the Lyophilization Process of TABLE 1

The objective of this study was to run a full load of vials using the first GMP lots of the compound of Formula (1) to demonstrate that the refined cycle was safe, effective and robust. Bulk solution formulated with the compound of Formula (1) was filled at a target fill volume of 1 mL into 1620 vials on four trays. A large foreign particle which was bright white and floated was present in the solution at the end of compounding. Thermocouples were placed into 4 edge vials and 6 center vials. Upon completion of loading, the chamber was evacuated to within 11-13 PSIA to ensure a proper seal of the chamber. The product was freeze dried according to the process parameters in TABLE 6.

TABLE 6

| Step | Shelf Temp. Setpoint (° C.) | Soak Time (hours) | Ramping Rate (° C./hour) | Pressure Set point |
|---|---|---|---|---|
| Loading | 20 | 1 | | Evacuate to 12 PSIA to ensure chamber is airtight |
| | | | 30 | |
| Freezing | −45 | 1 | | |
| | | | 30 | |
| Annealing | 0 | 2 | | |
| | | | 30 | |
| Freezing | −45 | 2 | | |
| | −45 | 4 | | 20 microns |
| Primary Drying | | | 30 | |
| | −6 | 80.5 | | |
| Secondary Drying | | | 12 | |
| | 40 | 10 | | 200 microns |
| Stoppering | | | 30 | |
| | 20 | | | 14.7 PSIA |

Figure 37:
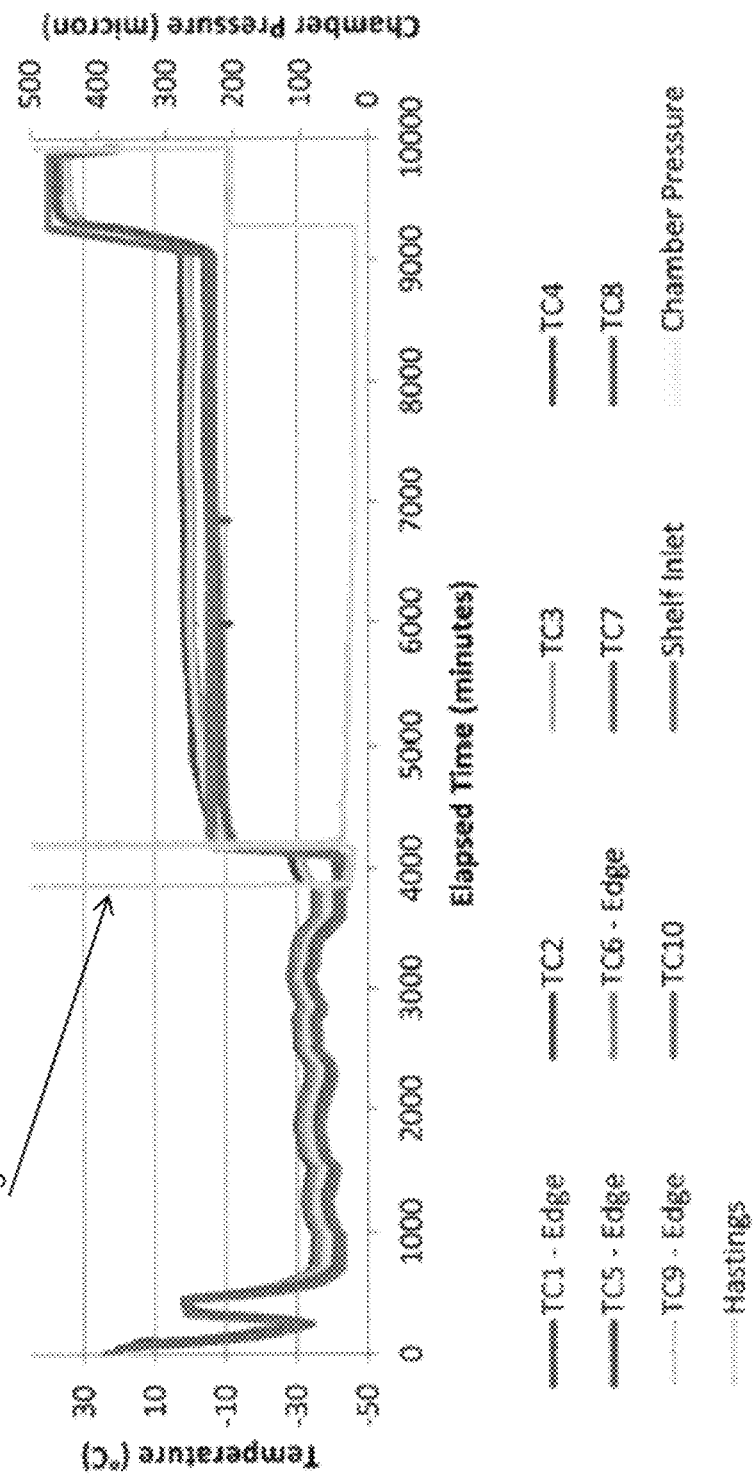
FIG. 37 provides the lyophilization cycle parameter results of TABLE 6.

FIG. 37 provides the lyophilization cycle parameter results.

Figure 38:
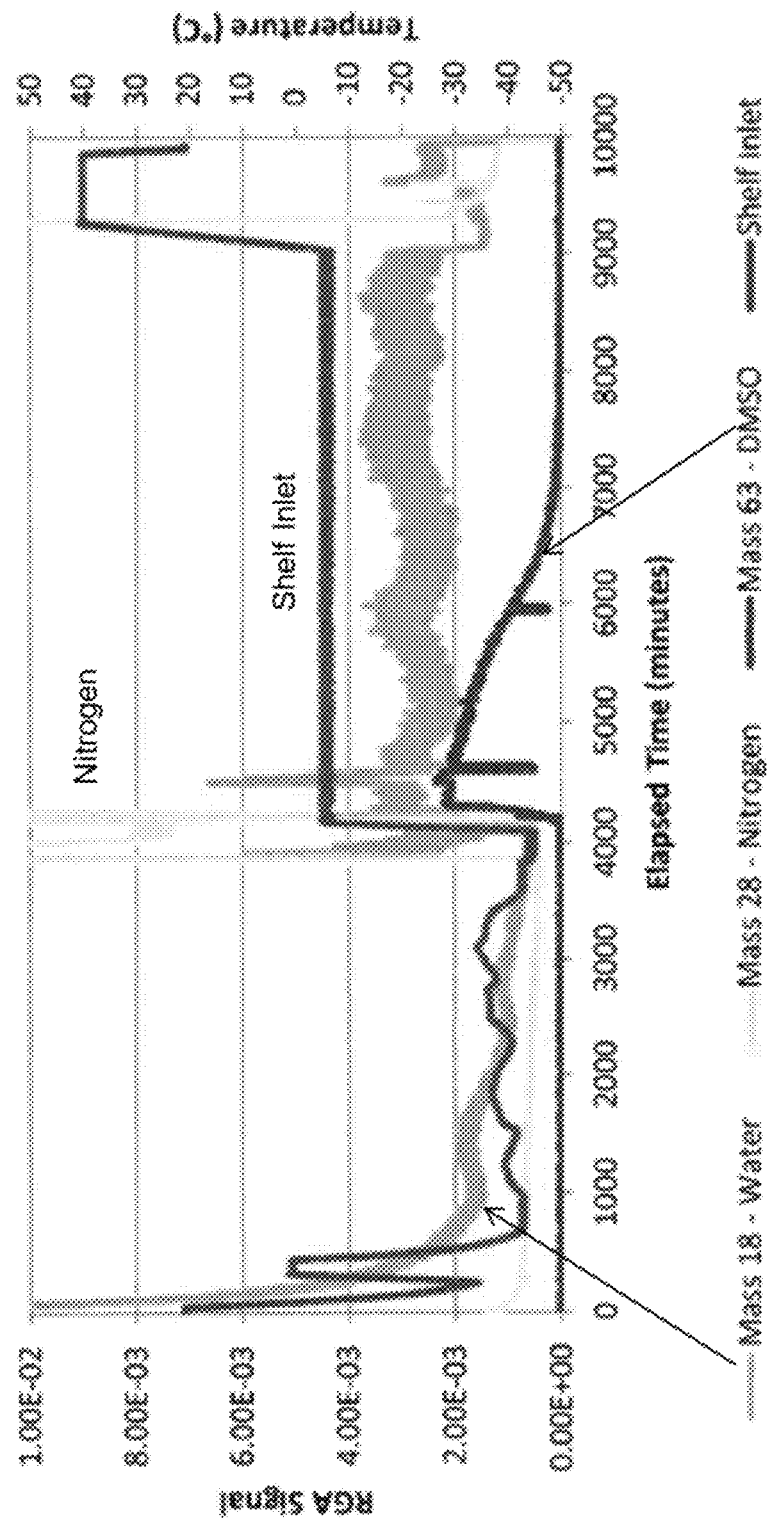
FIG. 38 provides the RGA data for the lyophilization parameters of TABLE 6.

FIG. 38 provides the RGA data for the lyophilization parameters of TABLE 6. The RGA detected DMSO in the chamber throughout primary drying. The signal approached baseline levels after approximately 55 hours in primary drying. The RGA did not detect a second increase in the DMSO level during secondary drying.

A summary of the product temperatures at equilibrium are provided in TABLE 7 below:

TABLE 7

| | | Product Temperatures[1] (° C.) Average (Min to Max) | |
|---|---|---|---|
| Step | Target Shelf Temperature (° C.) | Center (T/C 2, 3, 4, 7, 8, 10) | Edge (T/C 1, 5, 6, 9) |
| Loading | 20 | 20.1 (19.3 to 20.5) | 19.4 (18.6 to 20.4) |
| Freeze | −45 | −31.7 (−32.4 to −30.3) | −26.4 (−28.5 to −25.4) |
| Annealing | 0 | −1.3 (−2 to −0.6) | −0.1 (−1.1 to 0.6) |
| Freeze | −45 | −39.3 (−39.9 to −38.1) | −33.7 (−35.8 to −32.5) |
| Freeze[2] | −45 | −42.2 (−42.7 to −41.5) | −37.1 (−38.4 to −35.6) |
| Freeze | −45 | −41.6 (−42.6 to −40.4) | −30.3 (−31.7 to −28.4) |
| Primary Drying | −6 | −5.1 (−6.1 to −4) | 1.2 (0.3 to 2.6) |
| "Break" | — | −7.4 (−7.7 to −7.1) | −2.5 (−2.9 to −1.6) |
| Secondary Drying | 40 | 37.5 (37.1 to 38) | 35.1 (34.8 to 35.3) |

[1]Product Temperatures indicate temperature at end of segment.
[2]Indicates product temperatures immediately prior to evacuation.

A summary of product break temperatures is shown in TABLE 8 below:

TABLE 8

| Center | | | Edge | | |
|---|---|---|---|---|---|
| Thermo-couple | Temperature (° C.) | Time (hours) | Thermo-couple | Temperature (° C.) | Time (hours) |
| 2-center | −7.3 | 23.3 | 1-edge | −1.6 | 4820 |
| 3-center | −7.7 | 41.7 | 5-edge | −2.6 | 5395 |
| 4-center | −7.4 | 37 | 6-edge | −2.9 | 5275 |
| 7-center | −7.2 | 29.3 | 9-edge | −2.8 | 5000 |
| 8-center | −7.6 | 40.2 | Average | −2.5 | 15.8 |
| 10-center | −7.1 | 24.4 | Minimum | −2.9 | 10.8 |
| Average | −7.4 | 32.6 | Maximum | −1.6 | 20.3 |
| Minimum | −7.7 | 23.3 | | | |
| Maximum | −7.1 | 41.7 | | | |

At the completion of the study, a 100% inspection for physical appearance was performed. Reconstitution was performed on 9 center vials and 9 edge vials per tray. Turbidity testing was performed by pooling 3 reconstituted vials per sample.

Figure 39:
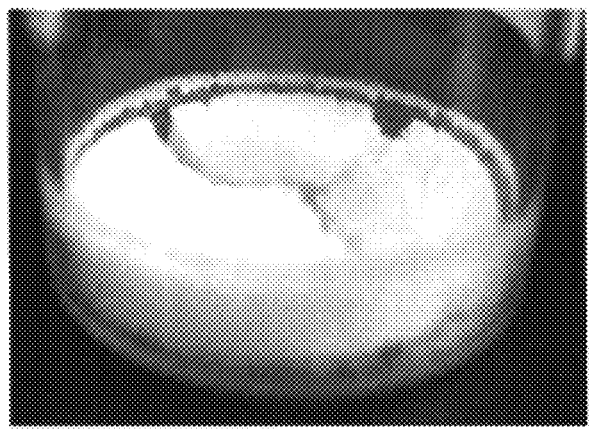
FIG. 39 shows the top view of a vial of the lyophilized product of TABLE 6.
Figure 40:
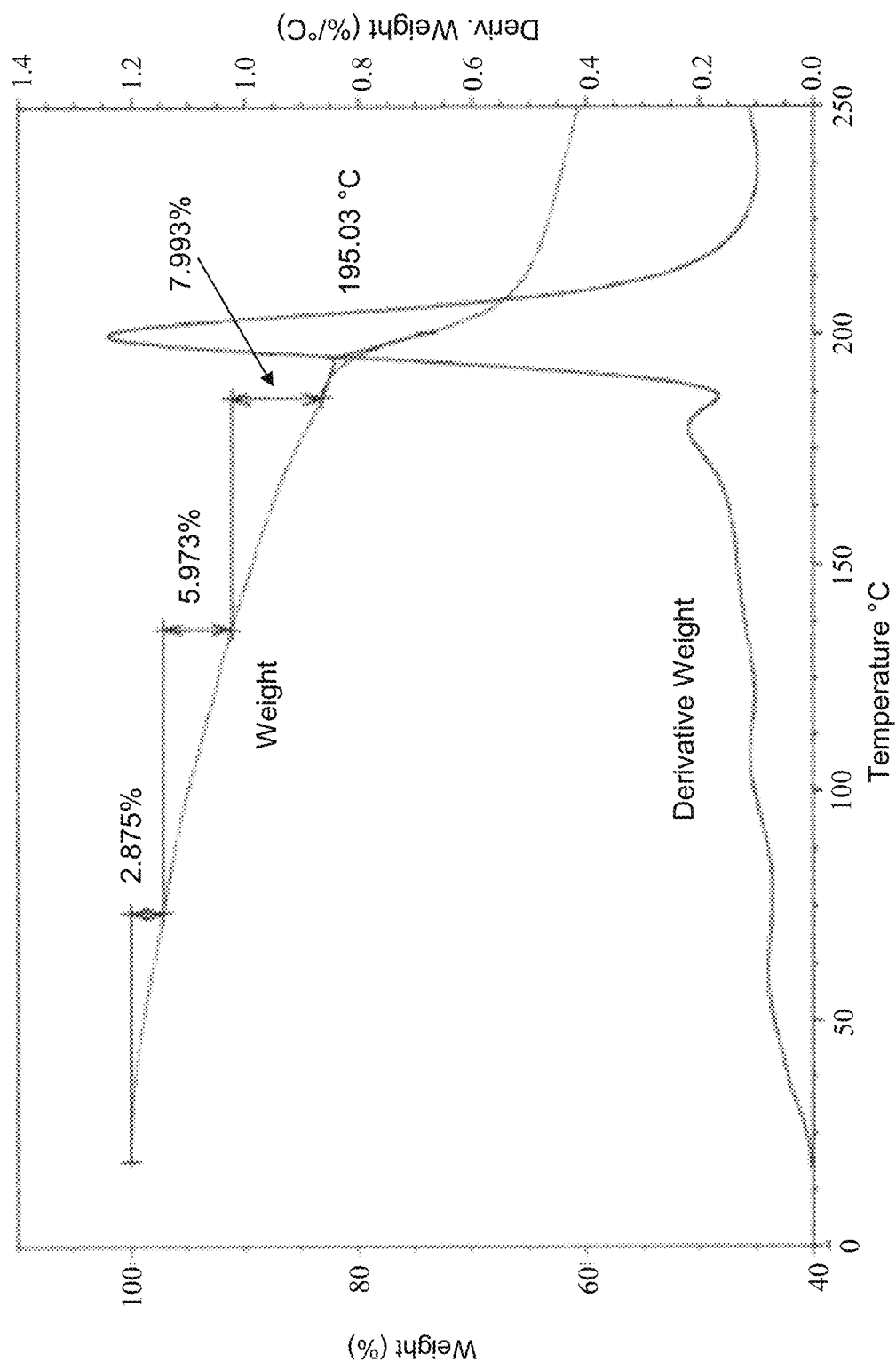
FIG. 40 provides a thermogravimetric analysis thermogram for a study of TABLE 6.

FIG. 39 shows the top view of a vial of the lyophilized product. The product appeared as a dense, yellow cake. The original fill height was 5 mm while the product height was 4 mm with uniform shrinkage observed around the sides of 1 mm. The top of the cake appeared matte with areas of sheen while the sides and bottom appeared matte. The top of the cake was concave and textured with cracks through the cake height. Upon inversion, the cake fell apart and moved to the top of the vial. Upon jarring, the cake moved to the top of the vial and broke apart into fragment and powder. A minimal amount of residual material as a thin, yellow film was present around the original fill height.

Reconstitution was performed by extruding 1 mL of the diluent into each vial using a vial adapter or syringe and allowing the vials to sit undisturbed until clear. All the samples resulted in clear and colorless solutions. Due to the long reconstitution times, reconstitution times are reported in minutes for this study. TABLE 9 provides the average reconstitution times and turbidity results for this study.

TABLE 9

| | Average Recon Time (min) | | Turbidity (NTU) | | |
|---|---|---|---|---|---|
| Tray | Center | Edge | Center | Edge | Appearance |
| 1 | 28 | 24 | (6, 0.84, 1.97) | (0.97, 0.98, 2.2) | Clear and Pale Yellow |
| 2 | 22 | 26 | (3.98, 6.75, 1.29) | (1.2, 1.14, 0.97) | Clear and Pale Yellow |
| 3 | 23 | 25 | (1.01, 0.91, 0.68) | (0.73, 0.79, 0.64) | Clear and Pale Yellow |
| 4 | 24 | 22 | (0.92, 0.85, 0.82) | (0.95, 1.58, 0.65) | Clear and Pale Yellow |

The TGA analysis results are provided in TABLE 40. The center product temperatures all remained below the critical temperature of −4° C. prior to reaching a break. The edge thermocouple product temperatures were all slightly above the critical temperature at the break; however, no indication of collapse or meltback was observed in the edge vials. Product temperatures reached a steady state after approximately 55 hours in primary drying. The TGA testing results showed a total weight loss of 17%, which was consistent with previous results.

Example 3: A Further Lyophilization Method for a Compound of Formula (1)

A series of vials containing the solution containing a compound of formula (1) were lyophilized using the specific cycle parameters set out below in TABLE 10.

TABLE 10

Lyophilization cycle operating parameters

| Stage | Event | T (° C.) | P | Time (h) |
|---|---|---|---|---|
| | Load | 5 | Atm | 0.0 |
| First freezing stage | Ramp temperature | −45 | Atm | 1 |
| First freezing stage | Hold temperature | −45 | Atm | 1.5 |
| First warming stage | Ramp temperature | 0 | Atm | 1.3 |
| First warming stage | Hold temperature | 0 | Atm | 2 |
| Second freezing stage | Ramp temperature | −45 | Atm | 2 |
| Second freezing stage | Hold temperature | −45 | Atm | 2 |
| Primary drying stage | Decrease and hold pressure | −45 | 6 µbar | 4 |
| Primary drying stage | Ramp temperature | −20 | 6 µbar | 3 |
| Primary drying stage | Hold temperature | −20 | 6 µbar | 12 |
| Primary drying stage | Ramp temperature | −5 | 6 µbar | 3 |
| Primary drying stage | Hold temperature | −5 | 6 µbar | 24 |
| Secondary drying stage | Ramp temperature | 65 | 6 µbar | 6 |
| Secondary drying stage | Hold temperature | 65 | 6 µbar | 15 |

Upon completion of the lyophilization cycle, the lyophilizer was back-filled with nitrogen, and the vials were completely and automatically stoppered. Vials were aseptically transferred to an isolator where each of the vials was automatically capped with a blue aluminum flip-off cap. Vials were visually inspected before proceeding with sampling for release testing, and the labeling and packaging operation. Vials were kept at 2-8° C. until ready. Each vial was labeled for its content.

Example 4: Comparative Tests

I. Lyophilized Formulations Made by the Process Disclosed Herein:

Bulk solutions were made containing the sodium salt of the compound of formula (1) at four different concentrations in DMSO and the resulting solutions (designated A to D) were filled into lyophilization vials and subjected to lyophilization using the protocol described above in Example 1. Pirani and Baratron gauges were used to determine the end of the primary drying (sublimation) stage. FIG. 1 shows the progressive reduction in DMSO content over time during the primary and secondary drying stages.

Following lyophilization, the lyophilized samples were analysed for purity (% purity by HPLC), DMSO residual content, and residual moisture. The samples were reconstituted by dissolving them in the non-aqueous solvent system described in TABLE 11 below and the reconstitution time and appearance of the reconstituted formulations were analysed.

TABLE 11

Solvent for reconstitution

| | % of each ingredient | Grade | Function |
|---|---|---|---|
| Propylene glycol | 65 | NF, PhEur | Solvent |
| Glycerin | 25 | NF, PhEur | Solvent |
| Alcohol/Ethanol | 10 | USP, PhEur | Thinning agent |

The results of the analyses are set out in TABLE 12 below. Results for four different concentrations, n=1

TABLE 12

| Sample ID → <br> Analysis ↓ | A (100 mg/mL) | B (75 mg/mL) | C (50 mg/mL) | D (25 mg/mL) |
|---|---|---|---|---|
| % Purity by HPLC (API purity 93.6%) | 93.2 | 93.1 | 93.2 | 93.2 |
| DMSO residual solvent % | 19.4 | 15.1 | 19.2 | 20.8 |
| Residual Moisture | <LOQ | <LOQ | <LOQ | <LOQ |
| Reconstitution time (manual) | 17 min 40 s | 12 min 51 s | 12 min 49 s | 18 min 51 s |
| Appearance of the reconstituted solution | Clear solution, slightly yellow | | | |

LOQ=limit of quantitation

II. Comparative Formulations:

Bulk solutions of the sodium salt of the compound of formula (1) at a concentration of 100 mg/mL were subjected to lyophilization using the apparatus described in EXAMPLE 3 above but a different temperature profile which did not include the first warming stage during the freezing of the solution but included freezing the formulation at different freezing rates. The characteristics of the Comparative formulations prepared in this way are shown in TABLE 13 below.

TABLE 13

| Identification N° → <br> Analysis | Specification | FP1 | FP2 Result | FP3 |
|---|---|---|---|---|
| Appearance of the cake (all vials) | Description | Compact cake detached from the walls | Compact cake detached from the walls | Firm cake with cracks adhering to the bottom of the vial |
| Appearance of the reconstituted solution and time for reconstitution | Clear solution free of particles | Clear solution with particles sticking to the walls >30 min for complete dissolution | Clear solution with particles sticking to the walls >30 min for complete dissolution | Clear solution with particles sticking to the wall >30 min for complete dissolution |

TABLE 13-continued

| Identification N° → Analysis | Specification | FP1 | FP2 Result | FP3 |
|---|---|---|---|---|
| Water content | Below 1% (tentative) | 0.02% | 0.005% | 0.001% |
| Residual Solvent DMSO | Report result for information | 19.1% (FP1-9) | 19.4% (FP2-9) | 19.4% (FP3-9) |

III. Comparison of Results Obtained from the Formulations Described in I and II

The results shown in step I above demonstrate that when an intermediate warming stage ("first warming stage") is included during the freezing of the solution prior to primary drying in accordance with the process disclosed herein, the result is a lyophilized dry formulation which can be reconstituted in under 20 minutes and under 15 minutes in some cases.

By comparison, the Comparative formulations FP1, FP2 and FP3 described in II above, made by a process that omitted the intermediate warming stage, took longer to reconstitute (over 30 minutes). The intermediate warming stage can have the effect of increasing the porosity of the lyophilized product and increasing the surface area available for contact with solvent molecules, thereby increasing the solubility of the formulations.

IV. Comparison of Drying Times with Example 4 in WO2013/033176

Example 4 in WO2013/033176 describes the lyophilization of a solution of the sodium salt of the compound of formula (1) using the cycle parameters shown in TABLE 14 below.

TABLE 14

| | | Temperature/Pressure/Time | | |
|---|---|---|---|---|
| Stage | Event | T (° C.) | P | Time (minutes) |
| Freezing stage | Ramp temperature | −40 | Atm | 133 |
| Freezing stage | Hold temperature | −40 | Atm | 360 |
| Primary drying stage | Ramp temperature and pressure | −5 | 100 mTorr | 117 |
| Primary drying stage | Hold temperature and pressure | −5 | 100 mTorr | 1440 |
| Primary drying stage | Ramp temperature | 10 | 100 mTorr | 50 |
| Primary drying stage | Hold temperature | 10 | 100 mTorr | 1440 |
| Secondary drying stage | Ramp temperature and pressure | 30 | 50 mTorr | 67 |
| Secondary drying stage | Hold temperature and pressure | 30 | 50 mTorr | 1440 |
| Secondary drying stage | Ramp temperature | 60 | 50 mTorr | 100 |
| Secondary drying stage | Hold temperature | 60 | 50 mTorr | 1440 |
| Total lyophilization time | | 6587 minutes = 109 hours and 47 minutes | | |

In the process of the present disclosure, an intermediate (first) warming stage was interposed between two freezing stages when the solution is initially frozen, and this is believed to result in a much more porous structure from which DMSO can more readily sublime during the primary drying stage. Thus, a greater proportion of the DMSO is removed during the primary drying stage with the result that much shorter secondary drying stage can be employed.

Therefore, in summary, the process of the present disclosure can reduce the time necessary to produce a lyophilized product that has greatly enhanced dissolution characteristics.

Example 5: Larger Scale Studies on the 75 mg/mL and 100 mg/mL Formulations A and B The results obtained in the experiments described in EXAMPLE 3 showed that the lowest residual DMSO levels were obtained with formulation B in which a bulk solution containing a concentration of 75 mg/mL of active compound was lyophilized. Confirmatory studies were therefore carried out on 75 mg/mL and 100 mg/mL solutions of the sodium salt of the compound of formula (1) in DMSO. The lyophilization was carried out at a 100 vial scale, and analysis was carried out on multiple samples. The protocol used was as described in EXAMPLE 3. The properties of the resulting lyophilized products were as shown in TABLE 15 below.

TABLE 15

| | Sample ID | |
|---|---|---|
| Analysis | 100 mg/mL | 75 mg/mL |
| Residual DMSO % w/w, n = 3 | 17.4 (24.2 mg/vial) | 18.7% (25.4 mg/vial) |
| Reconstitution time (min), n = 3 | 8 min* | 8 min* |
| Appearance, n = 3 | Clear and colorless** | |
| Water Content, n = 2 | <LOQ | <LOQ |
| Assay % w/w, n = 2 | 107.8 | 105 |

*The reconstitution time does not include dissipation of bubbles (about 10 minutes). However, the reconstitution was carried out manually and did not require mechanised mixing apparatus.

**Although not seen in this instance, there can be occasions when the solutions are slightly hazy and/or slightly off-white to yellow in color.

The results in TABLE 15 demonstrate that the process of the present disclosure can be used, for example, to prepare lyophilized formulations that have a reconstitution time of less than ten minutes (excluding the time taken for bubbles to clear) and that reconstitution can be carried out manually without the need for mechanized mixers.

Example 6: Preparation of the Sodium Salt of the Compound of Formula (1)

The sodium salt of the compound of formula (1) was prepared as described in U.S. Pat. No. 7,700,567 (the content of which is hereby incorporated by reference) by coupling 1s (where $R_1$=carbamate protective group) with phosphoramidite building block 1d:

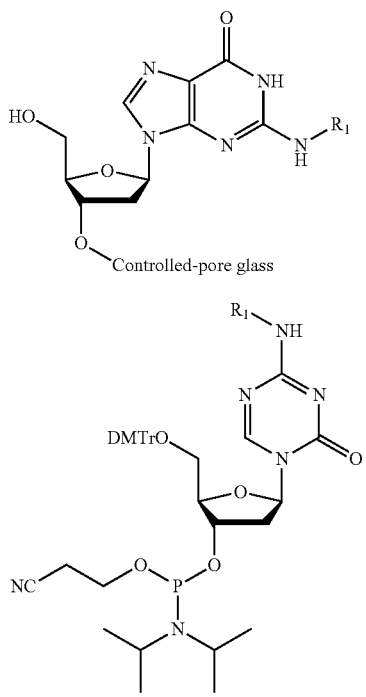

A protected 2'-deoxyguanosine-linked CPG solid support 1s (where $R_1$=tert-butyl phenoxyacetyl) was coupled with 2-2.5 equivalents of phenoxyacetyl decitabine phosphoramidite (1d, where $R_1$=phenoxyacetyl) in the presence of 60% of 0.3 M benzylthiotetrazole activator (in acetonitrile) for 10 minutes. The CPG solid support containing protected DpG dinucleotide was treated with 20 mL of 50 mM $K_2CO_3$ in methanol for 1 hour and 20 minutes. The coupled product was oxidized, the protective group was removed, and the resultant compound was washed, filtered, and purified by the ÄKTA Explorer 100 HPLC with a Gemini C18 preparative column (Phenomenex), 250×21.2 mm, 10 μm with guard column (Phenomenex), 50×21.2 mm, 10 μm, with 50 mM triethylammonium acetate (pH 7) in MilliQ water (Mobile Phase A) and 80% acetonitrile in MilliQ water (Mobile Phase B), with 2% to 20/25% Mobile Phase B in column volumes.

The ESI-MS (-ve) of DpG dinucleotide 2b:

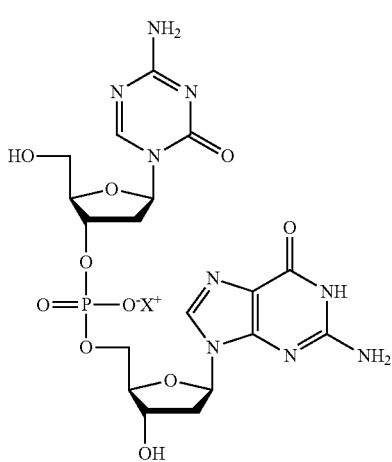

where $X^+$=triethylammonium (calculated exact mass for the neutral compound $C_{18}H_{24}N_9O_{10}P$ is 557.14), exhibited m/z 556.1 [M-H]$^-$ and 1113.1 for [2M-H]$^-$.

The sodium salt of the compound of formula (1), i.e. DpG dinucleotide 2b, where $X^+$=sodium, was obtained by re-dissolving the triethylammonium salt in 4 mL water, 0.2 mL 2M $NaClO_4$ solution. When 36 mL acetone was added, the dinucleotide precipitated. The solution was kept at −20° C. for several hours and centrifugated at 4000 rpm for 20 minutes. The supernatant was discarded and the solid was washed with 30 mL acetone followed by an additional centrifugation at 4000 rpm for 20 minutes. The precipitate, which was dissolved in water and freeze dried, exhibited m/z 556.0 [M-H]$^-$.

Example 7: Confirmation of Lyophilization Methods for a Compound Disclosed Herein

TABLE 16

| Step | Shelf Temp. Setpoint (° C.) | Soak Time (hours) | Ramping Rate (° C./hour) | Pressure Set point |
|---|---|---|---|---|
| Loading | 20 | 1 | 30 | Evacuate to about 621 Torr to ensure chamber is airtight |
| Freezing | −45 | 1 | 30 | |
| Annealing | 0 | 2 | 30 | |
| Freezing | −45 | 2 | | |
| Primary Drying | −45 | 4 | 30 | 20 microns |
| | −6 | 94.5 | | |
| Secondary Drying | 40 | 20.0 | 12 | 200 microns |
| Stoppering | | | 30 | |

The result of the lyophilization procedure shown in TABLE 16 was a clear reconstituted solution as opposed to a hazy solution obtained with other lyophilization procedures.

Example 8: Process Evaluation by Target and Boundary Studies for 100 mg of a Compound of Formula (1)/Vial for Injection Presentation To demonstrate the safety, efficacy, and robustness of the lyophilization process of EXAMPLE 7, a series of studies were performed in which various steps of the process were adjusted to be either at the target setpoint, or higher or lower than the target setpoint. The project was initially designed to consist of one study using the target process parameters followed by four studies using combinations of shelf temperatures±3° C. and chamber pressures±5 microns in primary drying and ±175 microns in secondary drying around the target conditions to demonstrate a proven acceptable range.

A deviation occurred during the initial studies where the chamber pressure in secondary drying was not increased based on the target chamber pressure of 200 microns. Therefore, three additional studies were included to demonstrate the actual target parameters and the high chamber pressure in secondary drying in combination with the high and low shelf temperature. A summary of the conditions performed in each study is included in TABLE 17.

TABLE 17

| Study | Freezing/Annealing Shelf Temperature | Primary Drying | | Secondary Drying | |
|---|---|---|---|---|---|
| | | Shelf Temperature | Chamber Pressure | Shelf Temperature | Chamber Pressure |
| A: Target | Target | Target | Target | Target | Low |
| B: HH | High | High | High | High | Low |
| C: LH | Low | Low | High | Low | Low |
| D: HL | High | High | Low | High | Low |
| E: LL | Low | Low | Low | Low | Low |
| F: Target | Target | Target | Target | Target | Target |
| G: LH | Low | Low | High | Low | High |
| H: HH | High | High | High | High | High |

During processing of Study G, the system proceeded to the primary drying shelf temperature without evacuating the chamber to the high boundary chamber pressure of 25 microns; however, no impact to the product was observed as the product temperatures remained frozen below the annealing temperature for the entire time.

The process data from Study H was not collected during the freezing, annealing and re-freezing process. The data collected at the end of the $2^{nd}$ freeze and in the ramp into primary drying indicates the lyophilizer performed the freezing, annealing, $2^{nd}$ freezing and evacuation steps as programmed. Therefore, no impact to the purpose of this study was observed as the high shelf temperature freezing process had been shown to be acceptable in Studies B and D.

All of the studies resulted in slightly friable cakes which, when reconstituted using the diluent, formed clear and colorless solutions with low turbidity. The low shelf temperature and low chamber pressure study required the longest time to complete sublimation. The high shelf temperature studies completed sublimation well within the allotted time while still maintaining the structure formed during freezing.

These target and boundary studies successfully demonstrated that the target lyophilization process has a range of ±3° C. around the target shelf temperature in each segment and ±5 microns around the target chamber pressure in primary drying and ±175 microns in secondary drying.

For all studies, the compound of Formula (1) was stored at 2° C.-8° C. until use. Upon use, the compound of Formula (1) was weighed and dispensed into approximately 90% of the total volume of DMSO. The quantity of the compound of Formula (1) was adjusted based on the reported Assay (as is, free acid) from the Certificate of Analysis for each lot. The DMSO was mixed vigorously with a magnetic stir bar for approximately 2 hours until all the compound was dissolved. Once all of the compound was dissolved, the solution was q.s. adjusted using additional DMSO to a final concentration of 100 mg/mL compound, assuming a density of 1.164 g/mL. The solution was then filtered through a 0.2 μm filer.

The general processing procedure is provided below:
1. The compound of Formula (1) solution was formulated and filtered according to the respective batch record procedures.
2. Washed 6R Type I tubing vials, Schott Part No 1123261, were filled to a target fill volume of 1 mL with the compound for Injection bulk solution.
3. West 20 mm, single vented 4432/50 G B2-TR stoppers, Part No 19700033, were partially inserted into the vials.
4. Thermocouples were placed in the bottom center of 10 product vials, 6 center and 4 edge.
5. Bottomless trays containing the product were placed on the shelves of a lyophilizer and the tray bottoms were removed. Bulk trays containing DMSO and spacers were placed on any shelves not containing product.
6. After loading the product, the chamber was evacuated to approximately 12 PSIA to ensure a good door seal.
7. The lyophilization cycle was completed according to the Program Table using the general parameters outlined in the following section. Data was recorded electronically every 5 minutes.

The target lyophilization cycle for a compound of Formula (1) for the comparison studies was:
1. The shelves were controlled at a target setpoint of 20° C. until the product was loaded onto the shelf. The temperature was held for 1 hour to allow all the product samples to equilibrate at the target temperature.
2. The shelves were chilled to a target shelf setpoint of −45° C. at an average controlled rate of 30° C./hour. The target shelf setpoint was held for 1 hour to allow all the product to equilibrate at the target temperature and for complete solidification.
3. The shelves were warmed at an average controlled rate of 30° C./hour to a target shelf temperature setpoint of 0° C. The target shelf was held at the setpoint for 2 hours to allow all the product samples to anneal at the target temperature.
4. The shelves were chilled to a target shelf setpoint of −45° C. at an average controlled rate of 30° C./hour. The target shelf setpoint was held for 2 hours to allow all the product samples to equilibrate at the target temperature and for complete solidification.
5. The condenser was chilled to below −40° C. and the chamber was evacuated to the target pressure. The target shelf setpoint was held for an additional 4 hours to allow any unfrozen DMSO to vaporize.
6. The chamber pressure was controlled at the target setpoint to allow the DMSO to sublime.
7. The shelves were warmed at an average controlled rate of 30° C./hour to a target shelf temperature setpoint of −6° C., and controlled at the target shelf setpoint for 80.5 hours until all the DMSO had sublimed.
8. The shelves were warmed to a target shelf temperature setpoint of 40° C. at an average controlled rate, and held at the target shelf setpoint to lower the residual DMSO levels.
9. The shelves were chilled to a target setpoint of 20° C. for unloading. The chamber pressure was raised to 14.7±0.7 PSIA by bleeding filtered Nitrogen, NF into the chamber. The vials were stoppered and unloaded.

TABLE 18 below provides a summary of the process parameters for the boundary studies.

TABLE 18

| | | Shelf Temperature Setpoint (° C.) | | | | |
|---|---|---|---|---|---|---|
| Step | Time | Target | HH | LH | HL | LL |
| Product Loading | 1 | 20 | 23 | 17 | 23 | 17 |
| Freezing Ramp | 2.2 | −45 | −42 | −48 | −42 | −48 |
| Freezing | 1 | −45 | −42 | −48 | −42 | −48 |
| Annealing Ramp | 1.5 | 0 | 3 | −3 | 3 | −3 |
| Annealing | 2 | 0 | 3 | −3 | 3 | −3 |
| Freezing Ramp | 1.5 | −45 | −42 | −48 | −42 | −48 |
| Freezing[1] | 5 | −45 | −42 | −48 | −42 | −48 |
| Primary Drying Ramp | 1.3 | −6 | −3 | −9 | −3 | −9 |

TABLE 18-continued

| Step | Time | Shelf Temperature Setpoint (° C.) | | | | |
|---|---|---|---|---|---|---|
| | | Target | HH | LH | HL | LL |
| Primary Drying | 80.5 | −6 | −3 | −9 | −3 | −9 |
| Secondary Drying Ramp | 3.8 | 40 | 43 | 37 | 43 | 37 |
| Secondary Drying | 10 | 40 | 43 | 37 | 43 | 37 |
| Stoppering/Unload | 0.7 | 20 | 23 | 17 | 23 | 17 |
| Primary Drying Chamber Pressure (microns) | — | 20 | 25 | 25 | 15 | 15 |
| Secondary Drying Chamber Pressure (microns) | — | 200 | 375 | 375 | 25 | 25 |

[1]Pull Vacuum after 2 hours to setpoint listed at end of table and maintain pressure throughout remainder of process.

The diluent used for the following studies was:

TABLE 19

| | % of each ingredient | Grade | Function |
|---|---|---|---|
| Propylene glycol | 65 | NF, PhEur | Solvent |
| Glycerin | 25 | NF, PhEur | Solvent |
| Alcohol/Ethanol | 10 | USP, PhEur | Thinning agent |

Study A: Target Study with Low Chamber Pressure.

The objective of this study was to reproduce the target lyophilization process to demonstrate consistency of the boundary studies with the target lyophilization parameters. Bulk solution was filled at a target fill volume of 1 mL into approximately 400 vials on one tray. Bulk trays with DMSO were used to emulate full load conditions. Thermocouples were placed into 4 edge vials and 6 center vials. Upon completion of loading, the chamber was evacuated to within 11-13 PSIA to ensure a proper seal of the chamber. The product was freeze dried according to the original target process parameters that did not include the 200 micron chamber pressure setpoint in secondary drying.

During compounding, one white particle, with a diameter of approximately 3-5 mm, was observed floating in the solution. This particle was thought to be foreign material as it appeared a brighter white than the drug substance and the particle floated while most of the drug substance sank. Therefore, the study progressed with this particle undissolved.

Figure 5:
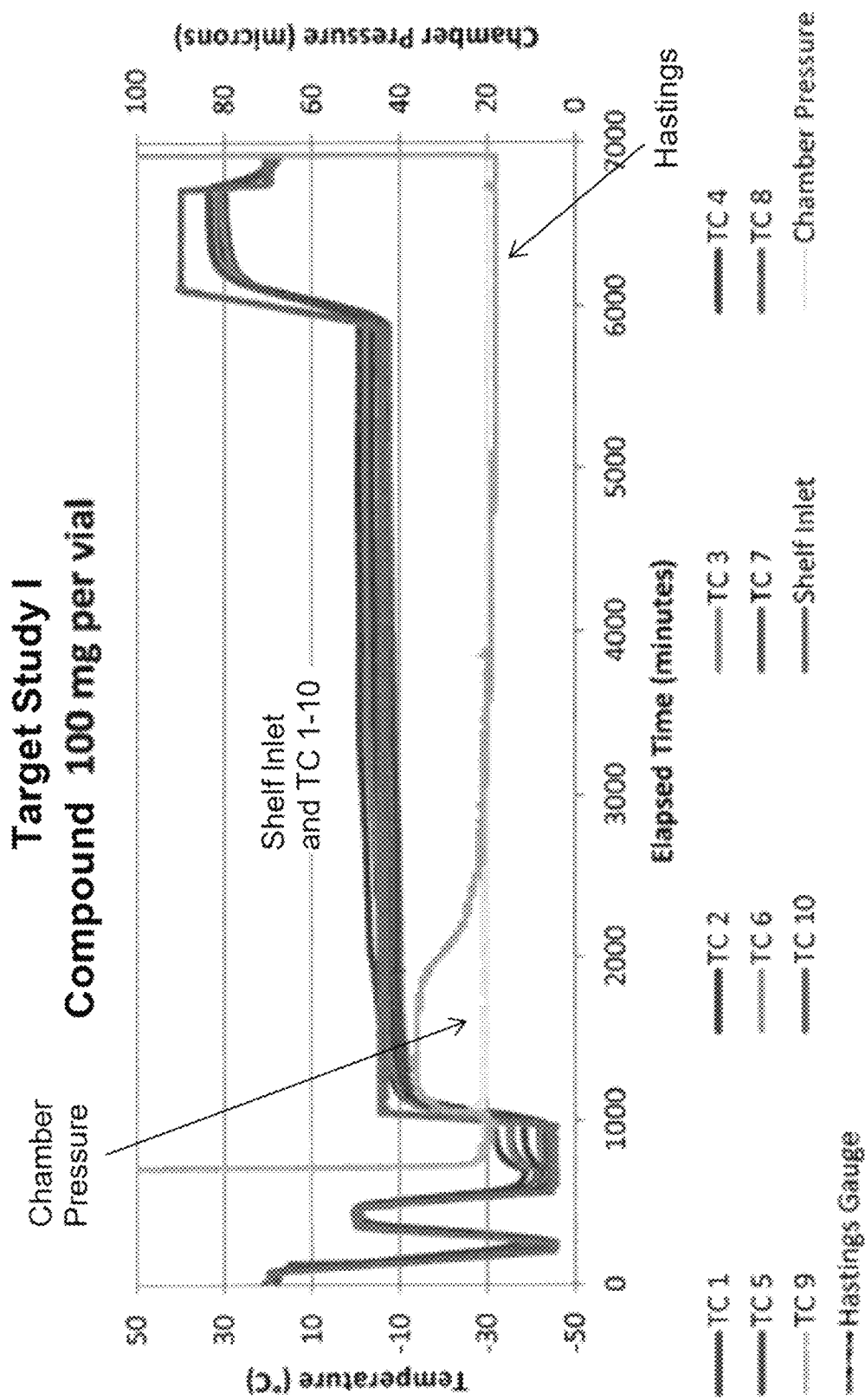
FIG. 5 depicts the lyophilization parameters for a target lyophilization process with low chamber pressure as described herein.

The lyophilization cycle parameter results are shown in FIG. 5.

A summary of the product temperatures at equilibrium are provided in TABLE 20 below:

TABLE 20

| Step | Target Shelf Temperature (° C.) | Product Temperatures[1] (° C.) Average (Min to Max) | |
|---|---|---|---|
| | | Center (T/C 5-10) | Edge (T/C 1-4) |
| Loading | 20 | 19 (18.9 to 19.1) | 18.3 (17.4 to 18.8) |
| Freeze | −45 | −43.4 (−44.2 to −42.8) | −40.2 (−42.2 to −37.2) |
| Annealing | 0 | −0.6 (−0.6 to −0.5) | −0.4 (−0.4 to −0.3) |
| Freeze[2] | −45 | −44.3 (−44.8 to −43.9) | −41.6 (−43.2 to −39.1) |
| Freeze | −45 | −42.8 (−43.6 to −41.9) | −35.2 (−38.5 to −31.8) |
| Primary Drying | −6 | −6.5 (−7.4 to −5.7) | −2.8 (−3.7 to −0.8) |
| "Break" | — | −9 (−9.8 to −8.2) | −5.3 (−6.8 to −4.2) |
| Secondary Drying | 40 | 33.1 (32.4 to 33.6) | 31.2 (29.9 to 32.4) |

[1]Product Temperatures indicate temperature at end of segment.
[2]Indicates product temperatures immediately prior to evacuation.

A summary of product break temperatures is shown in TABLE 21 below:

TABLE 21

| Center | | | Edge | | |
|---|---|---|---|---|---|
| Thermocouple | Temperature (° C.) | Time (hours) | Thermocouple | Temperature (° C.) | Time (hours) |
| 5 - center | −8.2 | 30.2 | 1 - edge | −5.1 | 22.5 |
| 6 - center | −9.8 | 29.2 | 2 - edge | −4.2 | 14.7 |
| 7 - center | −8.3 | 30.2 | 3 - edge | −5.1 | 24.5 |
| 8 - center | −9.5 | 27 | 4 - edge | −6.8 | 25.4 |
| 9 - center | −9 | 30.2 | — | — | — |
| 10 - center | −9.2 | 30.2 | — | — | — |
| Average | −9 | 29.5 | Average | −5.3 | 21.8 |
| Minimum | −9.8 | 27 | Minimum | −6.8 | 14.7 |
| Maximum | −8.2 | 30.2 | Maximum | −4.2 | 25.4 |

Figure 6:
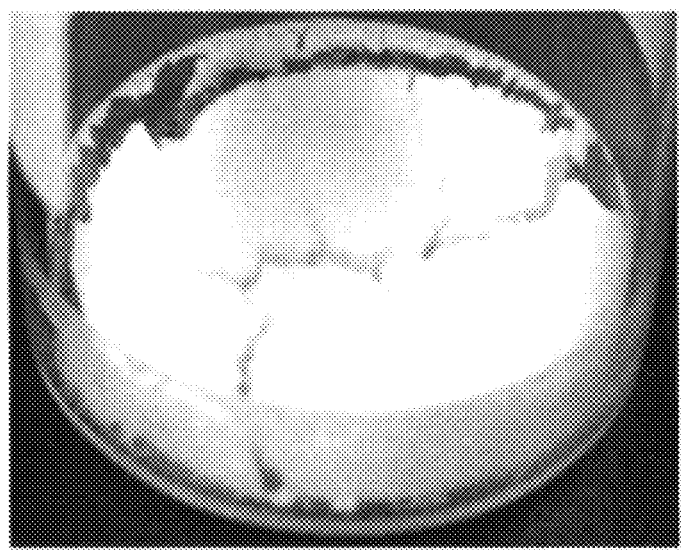
FIG. 6 provides a top view of a lyophilized product of a target lyophilization process with low chamber pressure as described herein.

At the completion of the study, a 100% inspection for physical appearance was performed. Reconstitution was performed on 9 vials. Turbidity testing was performed by pooling 3 reconstituted vials per sample. DSC and TGA were performed on two vials. FIG. 6 shows the top view of a vial of the lyophilized product. Physical appearance for the product vials showed a uniform, dense, white cake with uniform shrinkage around the sides.

Reconstitution was performed by extruding 1 mL of the diluent into each vial using a vial adapter or syringe and allowing the vials to sit undisturbed until clear. All the samples resulted in clear and colorless solutions. Due to the long reconstitution times, reconstitution times are reported in minutes for this study. TABLE 22 provides the average reconstitution time for this study. Reconstitution was performed with 1 mL of diluent and took approximately 20 minutes for the solution to fully clear. The reconstitution time was consistent or slightly shorter than previous studies with a compound of Formula (1) for Injection. Turbidity testing on all samples showed NTU values below 3, which are considered a clear solution with no more turbidity than the diluent.

TABLE 22

| Average Recon Time (min) | Turbidity (NTU) |
|---|---|
| 19.5 | (0.499, 0.599, 1.12) |

The TGA analysis results are provided in TABLE 23 below.

TABLE 23

| Vial | Weight Loss (% w/w) | Temperature Range (° C.) |
|---|---|---|
| 1 | 4.25 | 37 to 82 |
|   | 5.1 | 82 to 132 |
|   | 9.5 | 132 to 198 |
|   | Total: 18.85 | |
| 2 | 3.51 | 38 to 81 |
|   | 5.73 | 81 to 137 |
|   | 9.37 | 137 to 198 |
|   | Total: 18.61 | |

Figure 7:
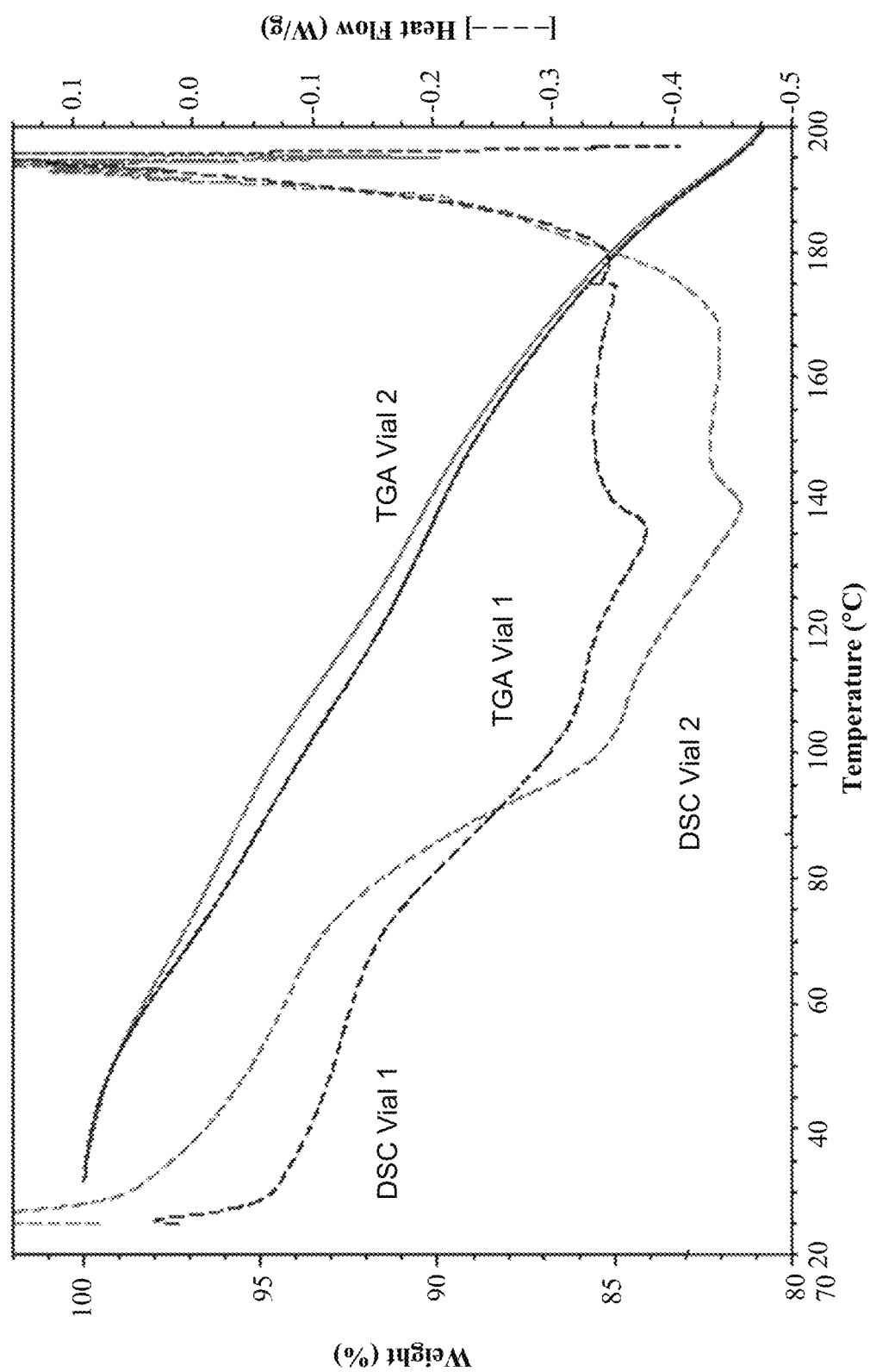
FIG. 7 provides an overlay of differential scanning calorimetry and thermogravimetric analysis thermograms of a target lyophilization process with low chamber pressure as described herein.

The DSC results are provided in FIG. 7 below. FIG. 7 provides an overlay between the DSC and TGA thermograms. TGA results showed approximately 19% w/w mass loss. The DSC showed a shift in baseline that correlated to the various weight loss events by TGA, which suggests the DSC changes were related to the evolution of residual DMSO from the samples. Product temperatures remained below the critical temperature of −4° C. prior to reaching a break for all the vials monitored with thermocouples. Product temperatures reached a steady state after approximately 64 hours in primary drying.

This study demonstrated that the recommended target parameters in primary drying with low pressure in secondary drying achieved an elegant product with consistent residual DMSO levels and low turbidity upon reconstitution. This study represents the effect of low pressure in secondary drying secondary drying with the target primary drying to establish the difference between the two pressure set points.

Study B: High Shelf Temperature, High Chamber Pressure

The objective of this study was to be the first of four boundary studies to show that the target lyophilization process was safe, effective, and robust. Bulk solution was filled at a target fill volume of 1 mL into approximately 400 vials on one tray. Bulk trays with DMSO were used to emulate full load conditions. Thermocouples were placed into 4 edge vials and 6 center vials. Upon completion of loading, the chamber was evacuated to within 11-13 PSIA to ensure a proper seal of the chamber. The product was freeze dried according to the High Shelf Temperature; High Chamber Pressure (HH) process parameters. Thus, the chamber pressure remained at 25 microns in secondary drying. The RGA was connected to the lyophilizer at a sample port located at the top of the lyophilizer chamber.

During compounding, the addition of the compound of Formula (1) was monitored. The material tended to clump, and the larger clumps would not properly wet. This tendency reduced the dissolution time and caused the material to float. Another wetted clump was observed to sink and stick to the bottom of the vessel. These materials remained undissolved and the materials were filtered for further analysis.

Figure 8:
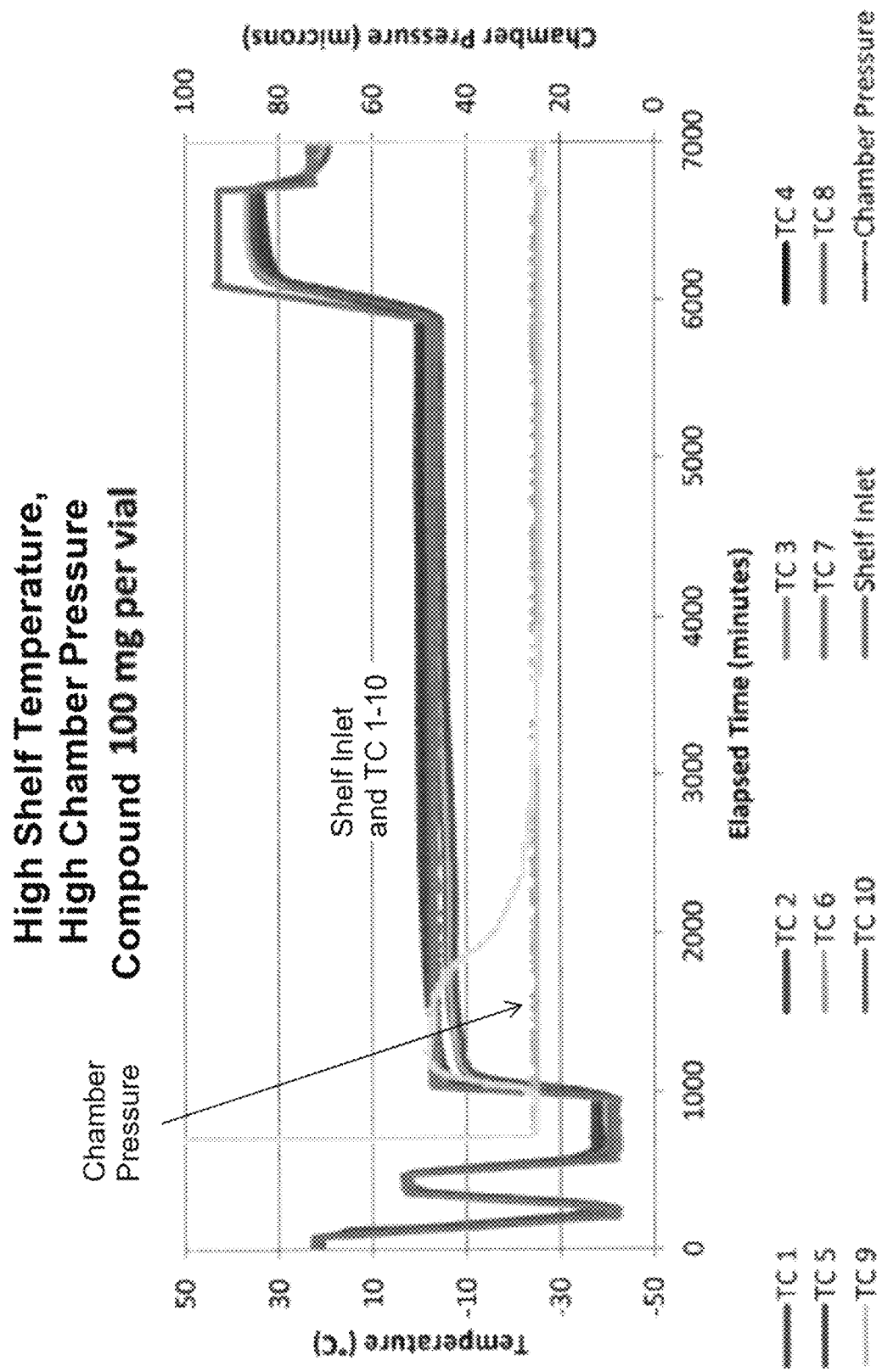
FIG. 8 depicts the lyophilization parameters for a high shelf temperature, high chamber pressure lyophilization process as described herein.

The lyophilization cycle parameter results are shown in FIG. 8.

A summary of the product temperatures at equilibrium are provided in TABLE 24 below:

TABLE 24

| Step | Target Shelf Temperature (° C.) | Product Temperatures[1] (° C.) Average (Min to Max) | |
|---|---|---|---|
| | | Center (T/C 5-10) | Edge (T/C 1-4) |
| Loading | 23 | 21.8 (21.6 to 21.9) | 21.1 (20.7 to 21.7) |
| Freeze | −42 | −40.3 (−40.7 to −39.8) | −37.9 (−39.5 to −36) |
| Annealing | 3 | −2.4 (2.4 to 2.5) | 2.6 (2.6 to 2.7) |
| Freeze[2] | −42 | −41.3 (−41.5 to −40.9) | −39.1 (−40.4 to −37.5) |
| Freeze | −42 | −40.5 (−40.9 to −39.8) | −39.1 (−40.8 to −37.2) |
| Primary Drying | −3 | −3.9 (−4.6 to −3.3) | −0.6 (−1.7 to −0.4) |
| "Break" | — | −6.5 (−7 to −5.7) | −3.5 (−4.1 to −3.1) |
| Secondary Drying | 43 | 36.5 (35.6 to 37) | 35.1 (33.5 to 37) |

[1]Product Temperatures indicate temperature at end of segment.
[2]Indicates product temperatures immediately prior to evacuation.

A summary of product break temperatures is shown in TABLE 25 below:

TABLE 25

| Center | | | Edge | | |
|---|---|---|---|---|---|
| Thermocouple | Temperature (° C.) | Time (hours) | Thermocouple | Temperature (° C.) | Time (hours) |
| 5 - center | −7 | 23.4 | 1 - edge | −3.1 | 7.9 |
| 6 - center | −6.8 | 23.9 | 2 - edge | −3.6 | 4.4 |
| 7 - center | −5.7 | 22.7 | 3 - edge | −3.2 | 12.4 |
| 8 - center | −6.3 | 27.8 | 4 - edge | −4.1 | 5.6 |
| 9 - center | −6.4 | 23.8 | | | |
| 10 - center | −7 | 28.2 | | | |
| Average | −6.5 | 25 | Average | −3.5 | 7.6 |
| Minimum | −7 | 22.7 | Minimum | −4.1 | 4.4 |
| Maximum | −5.7 | 28.2 | Maximum | −3.1 | 12.4 |

Figure 9:
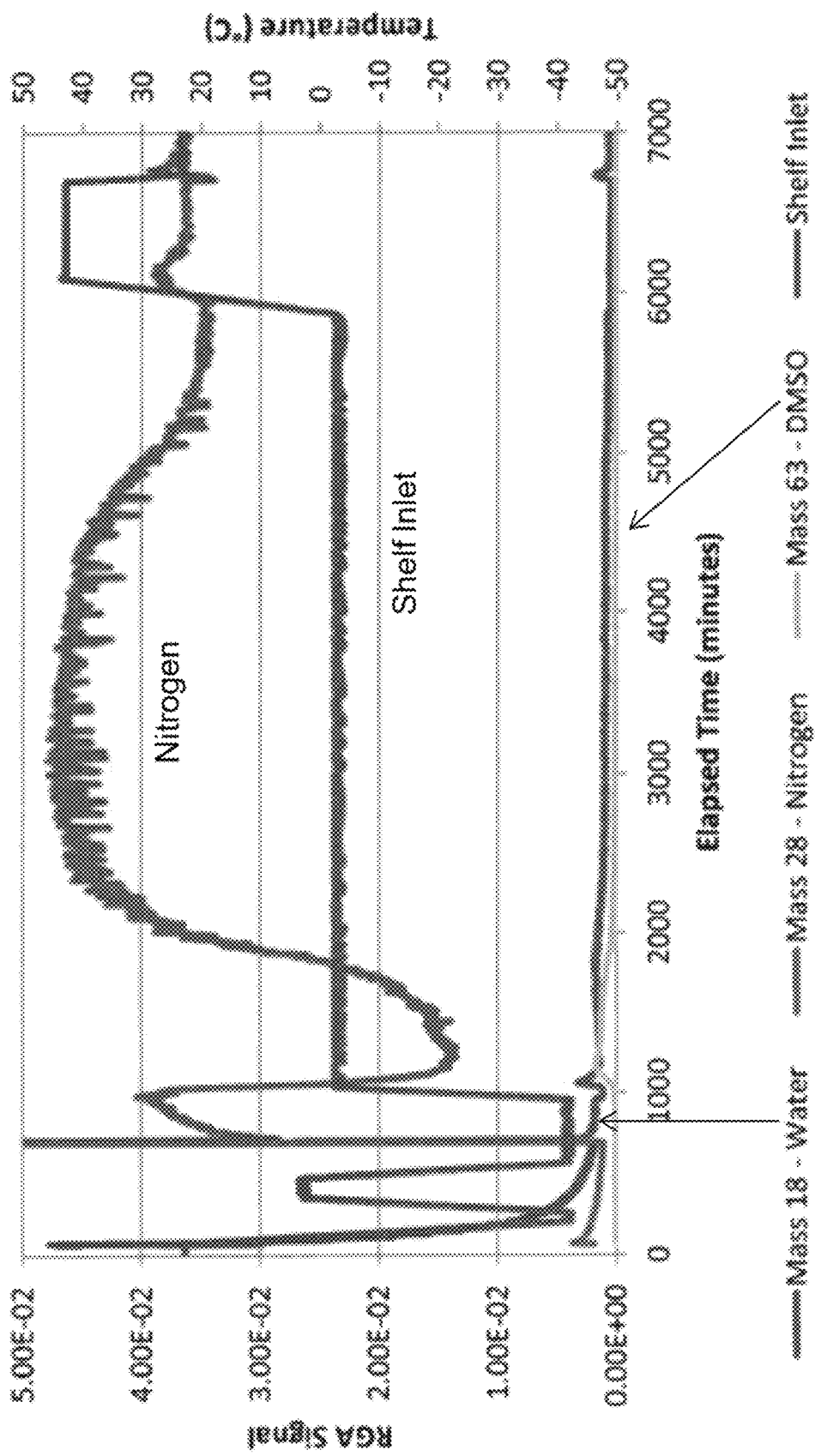
FIG. 9 depicts the residual gas analyzer results for a high shelf temperature, high chamber pressure lyophilization process as described herein.

The RGA data are shown in FIG. 9. The RGA data showed an increase in the DMSO signal at the beginning of primary drying. The DMSO levels returned to baseline levels after approximately 54 hours in primary drying.

Figure 10:
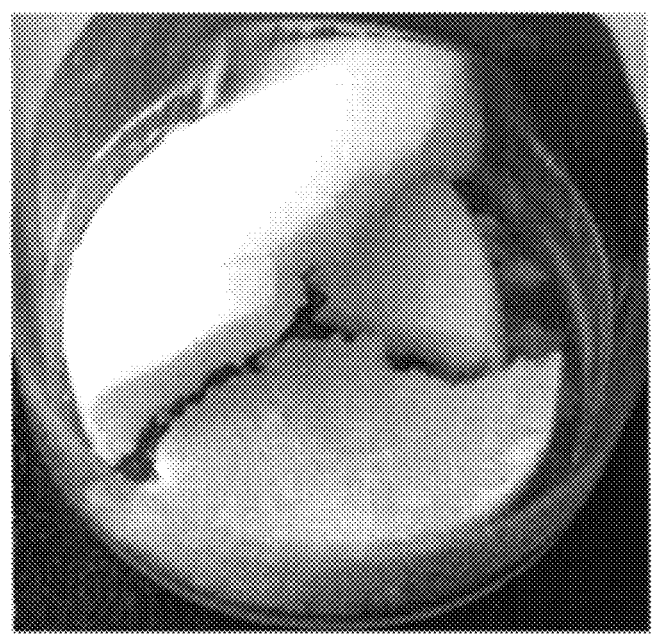
FIG. 10 provides a top view of a lyophilized product for a high shelf temperature, high chamber pressure lyophilization process as described herein.

At the completion of the study, a 100% inspection for physical appearance was performed. Reconstitution was performed on 9 vials. Turbidity testing was performed by pooling 3 reconstituted vials per sample. DSC and TGA were performed on two vials. FIG. 10 shows the top view of a vial of the lyophilized product. Physical appearance for the product vials showed a uniform, dense, white cake with uniform shrinkage around the sides.

Reconstitution was performed by extruding 1 mL of the diluent into each vial using a vial adapter or syringe and allowing the vials to sit undisturbed until clear. All the samples resulted in clear and colorless solutions. Reconstitution times are reported in minutes for this study. TABLE 26 provides the average reconstitution time for this study. Reconstitution was performed with 1 mL of diluent and took approximately 18 minutes for the solution to clear. Turbidity testing on all samples showed NTU values significantly higher than the target study. A retest was conducted and all three samples showed NTU values below 3. Previous testing has shown that if the pooled sample is not sufficiently mixed after pooling, then artificially-high turbidity results can occur.

TABLE 26

| Average Recon Time (min) | Turbidity (NTU) |
|---|---|
| 18 to 18.5 | (1.41, 4.92, 28.7) |
| | (0.647, 0.618, 0.674)[1] |

[1]Additional vials were tested after all the other studies were completed as the first set of vials was out of trend with the other studes.

The TGA analysis results are provided in TABLE 27 below.

TABLE 27

| Vial | Weight Loss (% w/w) | Temperature Range (° C.) |
|---|---|---|
| 1 | 3.25 | 33 to 84 |
| | 5.33 | 84 to 134 |
| | 9.49 | 134 to 197 |
| | Total: 18.07 | |
| 2 | 0.83 | 42 to 54 |
| | 2.44 | 54 to 84 |
| | 4.81 | 84 to 134 |
| | 9.27 | 134 to 197 |
| | Total: 17.35 | |

Figure 11:
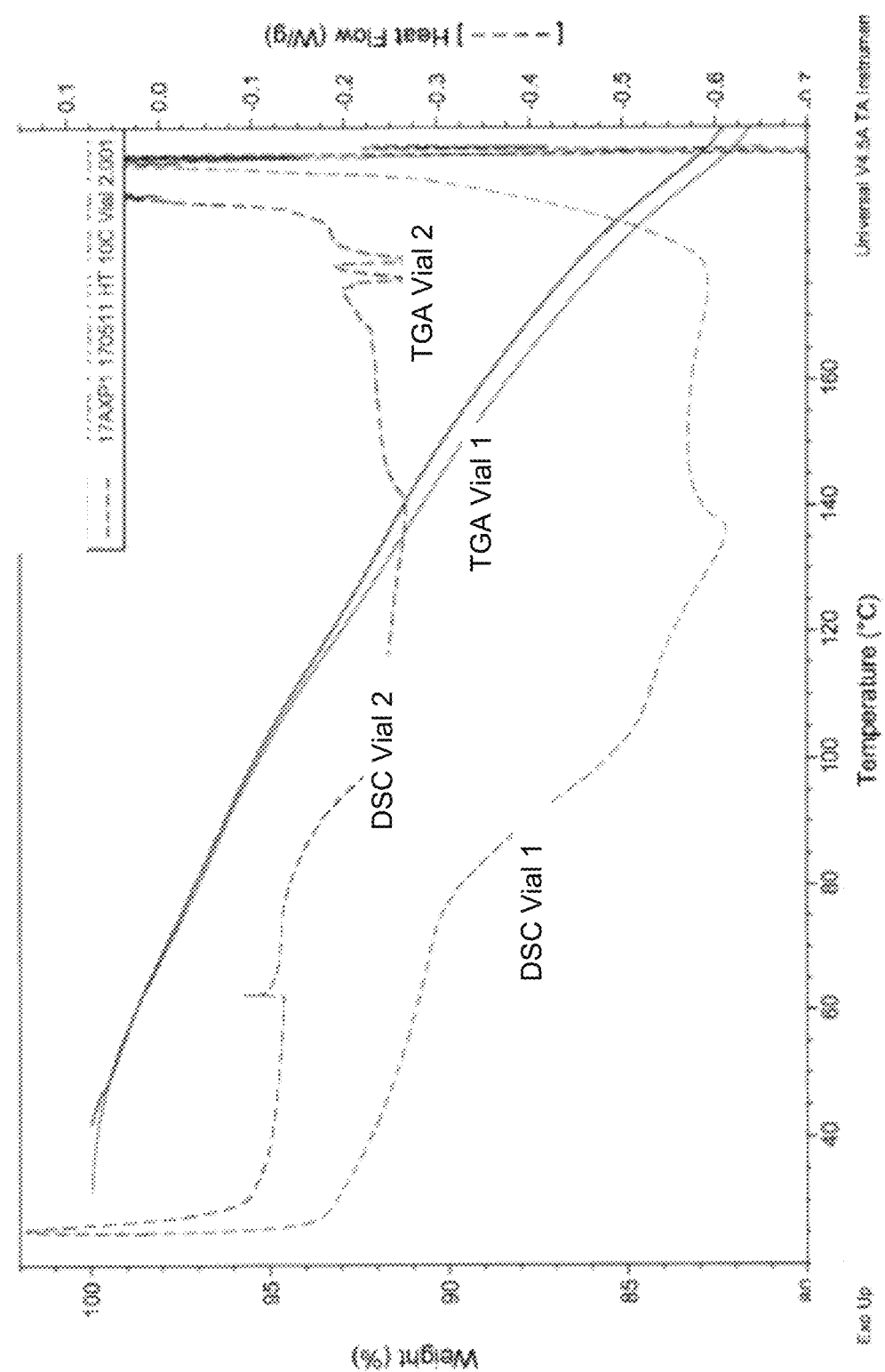
FIG. 11 provides an overlay of differential scanning calorimetry and thermogravimetric analysis thermograms for a high shelf temperature, high chamber pressure lyophilization process as described herein.

The DSC results are provided in FIG. 11 below. FIG. 11 provides an overlay between the DSC and TGA thermograms. TGA results showed approximately 17% to 18% w/w mass loss. The DSC showed a shift in baseline that correlated to the various weight loss events by TGA which was consistent with the target study.

Product temperatures remained below the critical temperature of −4° C. prior to reaching a break for all the center thermocouples. The edge thermocouples had break temperatures between −4° C. and −3° C.; however, no effect on the finished product was detected. The center thermocouple product temperatures were all within a range of −8° C. to −6° C. Product temperatures reached a steady state after approximately 54 hours in primary drying.

This study demonstrated that the high shelf temperature and high chamber pressure boundary conditions in primary drying with a relatively low chamber pressure in secondary drying achieved finished product similar to the target study.

Study C: Low Shelf Temperature, High Chamber Pressure

This study was the second of four boundary studies to show that the target lyophilization process was safe, effective, and robust. Bulk solution was filled at a target fill volume of 1 mL into approximately 400 vials on one tray. Bulk trays with DMSO were used to emulate full load conditions. Thermocouples were placed into 4 edge vials and 6 center vials. Upon completion of loading, the chamber was evacuated to within 11-13 PSIA to ensure a proper seal of the chamber. The product was freeze dried according to the Low Shelf Temperature; High Chamber Pressure (LH) process parameters. Thus, the chamber pressure remained at 25 microns in secondary drying. The RGA was connected to the lyophilizer at a sample port located at the top of the lyophilizer chamber.

During compounding, the compound of Formula (1) was checked for larger chunks. These chunks were broken up prior to adding the compound to the DMSO to assist in dissolution. Complete dissolution of the compound was achieved in approximately 1 hour. This result suggested that the previous issues with achieving a clear and colorless solution were a result of the dissolution properties of the compound and potentially the low shear mixing of a magnetic stir bar.

Figure 12:
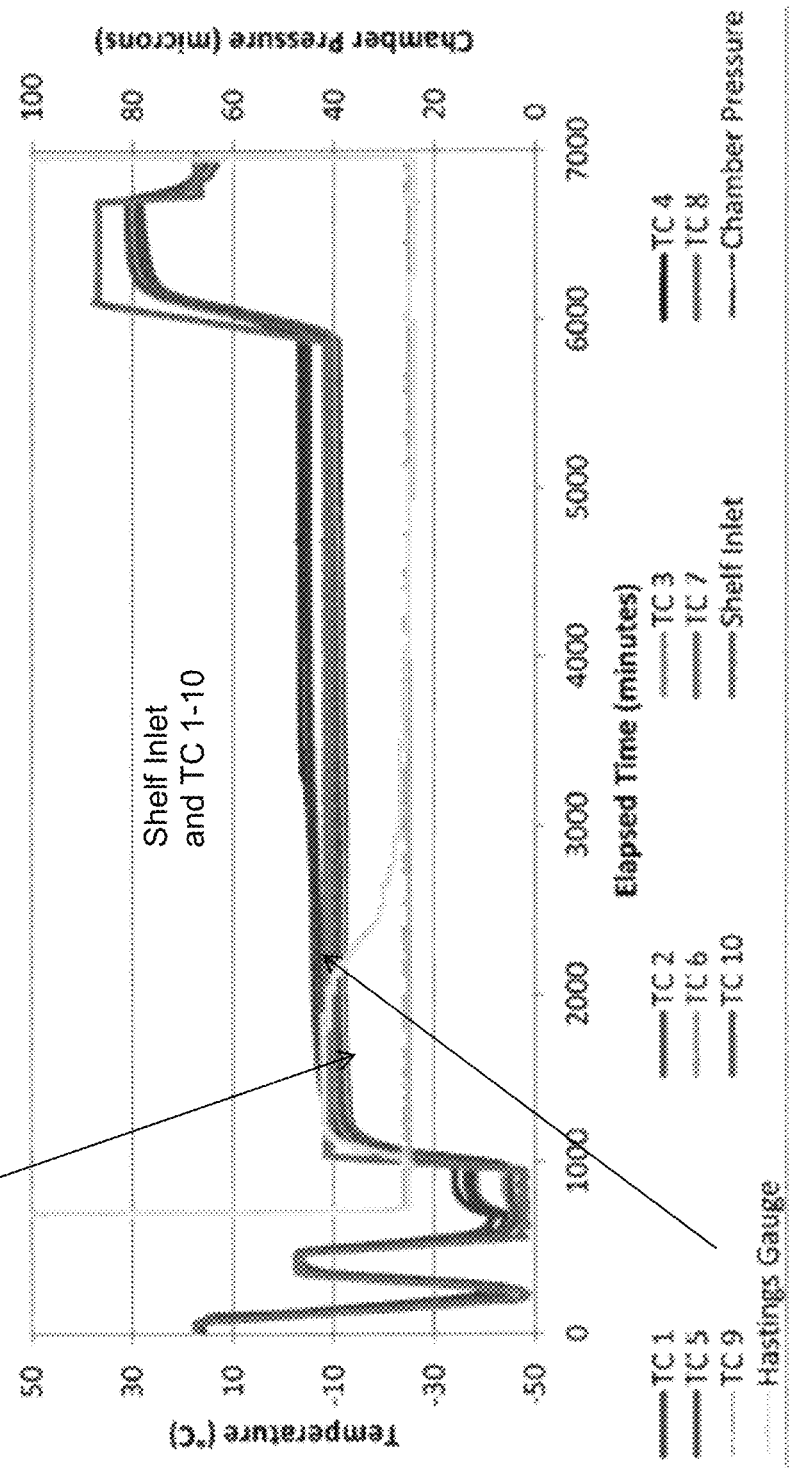
FIG. 12 depicts the lyophilization parameters for a low shelf temperature, high chamber pressure lyophilization process as described herein.

The lyophilization cycle parameter results are shown in FIG. 12.

A summary of the product temperatures at equilibrium are provided in TABLE 28 below:

TABLE 28

| | | Product Temperatures[1] (° C.) Average (Min to Max) | |
|---|---|---|---|
| Step | Target Shelf Temperature (° C.) | Center (T/C 5-10) | Edge (T/C 1-4) |
| Loading | 17 | 16.6 (16.5 to 16.7) | 16.3 (15.9 to 16.5) |
| Freeze | −48 | −46.1 (−46.4 to −45.2) | −41.9 (−43.9 to −39.9) |
| Annealing | −3 | −3.5 (−3.5 to −3.3) | −3 (−3.1 to −2.8) |
| Freeze[2] | −48 | −47 (−47.3 to −46.6) | −43.4 (−45 to −41.9) |
| Freeze | −48 | −45.1 (−45.7 to −43.8) | −36.6 (−38.3 to −34.1) |
| Primary Drying | −9 | −9.5 (−10.8 to −8.1) | −4.4 (−4.9 to −3.2) |
| "Break" | — | −11.3 (−12.1 to −10.2) | −6.8 (−7.8 to −5.9) |
| Secondary Drying | 37 | 30.4 (28.5 to 31.2) | 29.2 (28.3 to 29.8) |

[1]Product Temperatures indicate temperature at end of segment.
[2]Indicates product temperatures immediately prior to evacuation.

A summary of product break temperatures is shown in TABLE 29 below:

TABLE 29

| Center | | | Edge | | |
|---|---|---|---|---|---|
| Thermo-couple | Temperature (° C.) | Time (hours) | Thermo-couple | Temperature (° C.) | Time (hours) |
| 5 - center | −11.6 | 35.5 | 1 - edge | −5.9 | 28.3 |
| 6 - center | −10.2 | 34.3 | 2 - edge | −6.3 | 28.9 |
| 7 - center | −12.1 | 38.7 | 3 - edge | −7.8 | 20.4 |
| 8 - center | −11 | 35.1 | 4 - edge | −7.1 | 23.8 |
| 9 - center | −11.6 | 32.7 | | | |
| 10 - center | −11 | 32.4 | | | |
| Average | −11.3 | 34.8 | Average | −6.8 | 25.4 |
| Minimum | −12.1 | 32.4 | Minimum | −7.8 | 20.4 |
| Maximum | −10.2 | 38.7 | Maximum | −5.9 | 28.9 |

Figure 13:
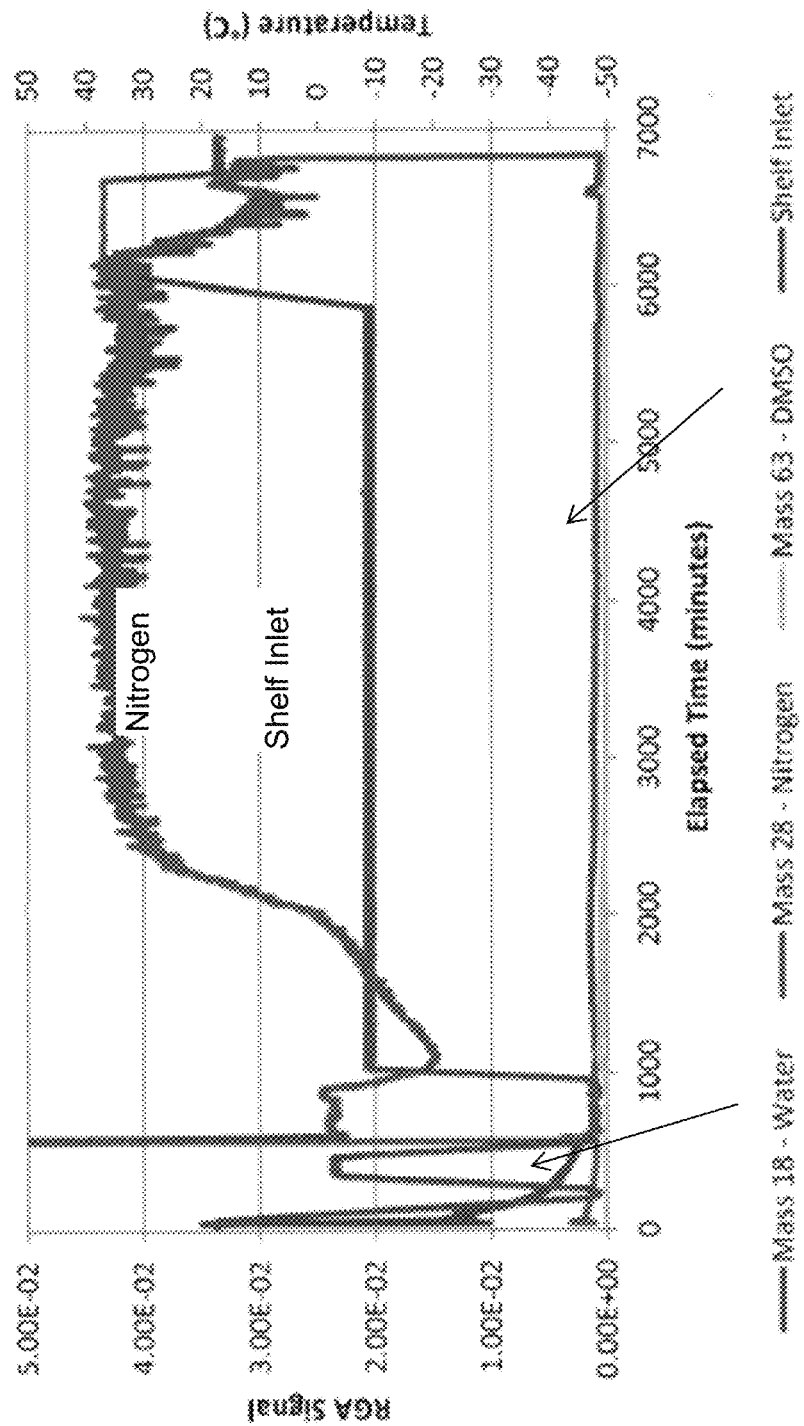
FIG. 13 depicts the residual gas analyzer results for a low shelf temperature, high chamber pressure lyophilization process as described herein.

The RGA data are shown in FIG. 13. The RGA data showed an increase in the DMSO signal at the beginning of primary drying. The DMSO levels returned to baseline levels after approximately 64 hours in primary drying.

Figure 14:
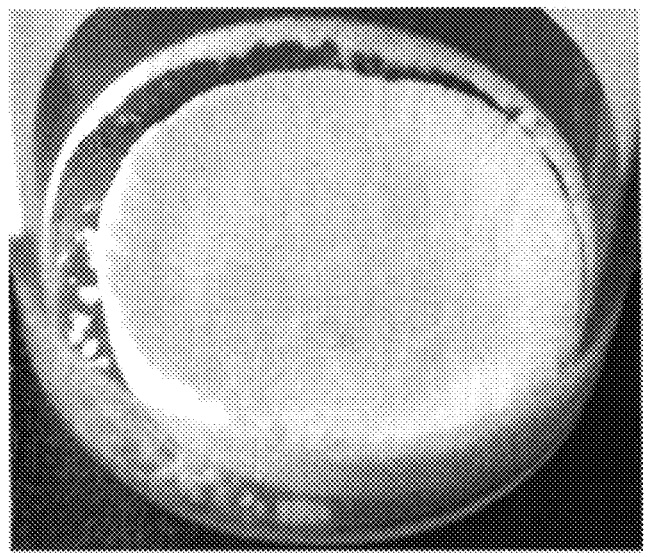
FIG. 14 provides a top view of a lyophilized product for a low shelf temperature, high chamber pressure lyophilization process as described herein.

At the completion of the study, a 100% inspection for physical appearance was performed. Reconstitution was performed on 9 vials. Turbidity testing was performed by pooling 3 reconstituted vials per sample. DSC and TGA were performed on two vials. FIG. 14 shows the top view of a vial of the lyophilized product. Physical appearance for the product vials showed a uniform, dense, white cake with uniform shrinkage around the sides.

Reconstitution was performed by extruding 1 mL of the diluent into each vial using a vial adapter or syringe and allowing the vials to sit undisturbed until clear. All the samples resulted in clear and colorless solutions. Reconstitution times are reported in minutes for this study. TABLE 30 provides the average reconstitution time for this study. Reconstitution took about 18 to 19 minutes for the solution to clear. Turbidity testing on all samples showed NTU values below 3, which are considered a clear solution with no more turbidity than the diluent.

TABLE 30

| Average Recon Time (min) | Turbidity (NTU) |
|---|---|
| 18 to 19 | (0.9, 0.841, 0.901) |

The TGA analysis results are provided in TABLE 31 below.

TABLE 31

| Vial | Weight Loss (% w/w) | Temperature Range (° C.) |
|---|---|---|
| 1 | 4.63 | 33 to 88 |
|   | 4.3 | 88 to 134 |
|   | 9.51 | 134 to 198 |
|   | Total: 18.44 | |
| 2 | 5.73 | 33 to 89 |
|   | 3.88 | 89 to 135 |
|   | 9.44 | 135 to 198 |
|   | Total: 17.35 | |

Figure 15:
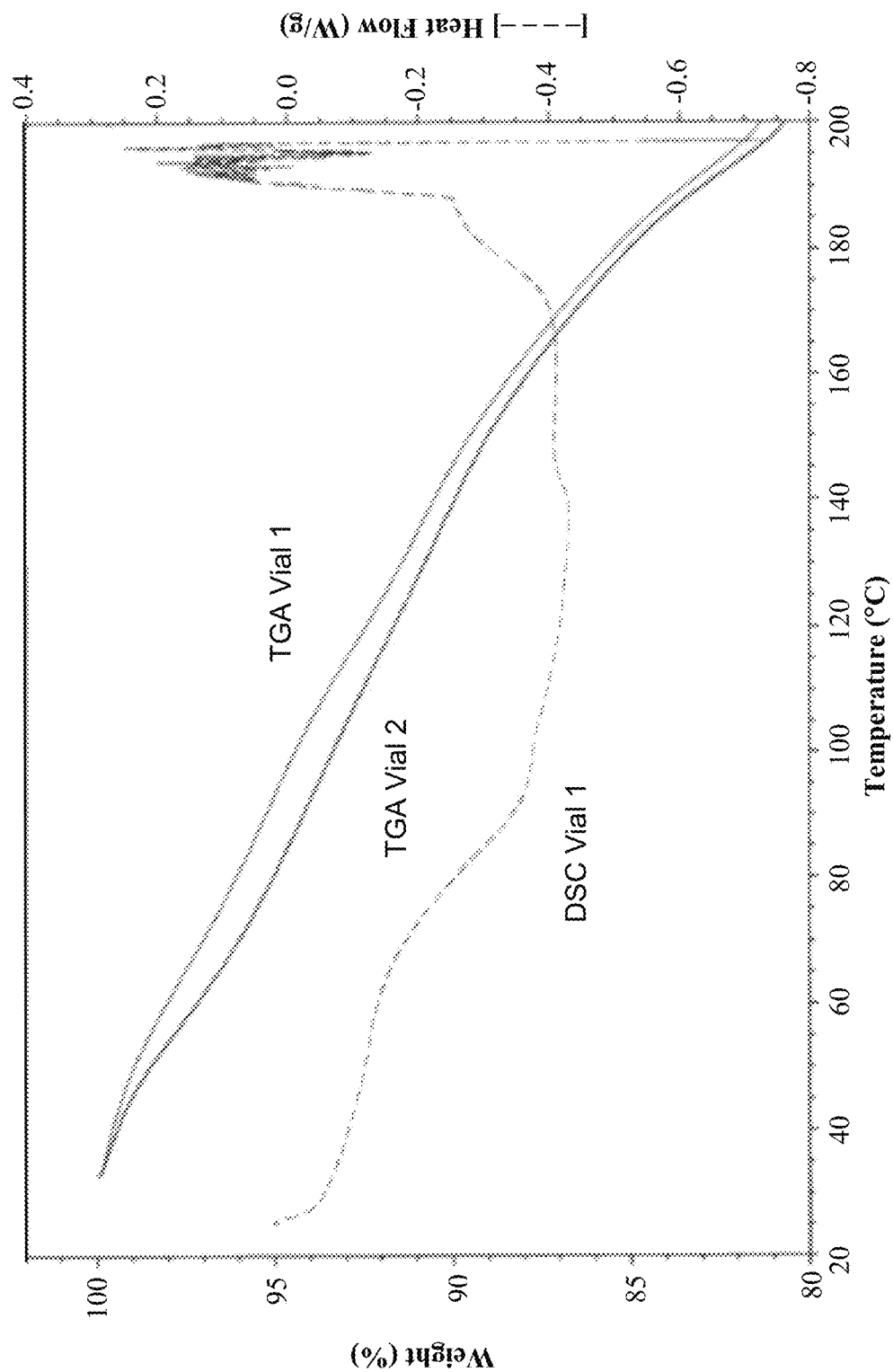
FIG. 15 provides an overlay of differential scanning calorimetry and thermogravimetric analysis thermograms for a low shelf temperature, high chamber pressure lyophilization process as described herein.

The DSC results are provided in FIG. 15 below. FIG. 15 provides an overlay between the DSC and TGA thermograms. TGA results showed approximately 19% w/w mass loss. The DSC showed a shift in baseline that correlated to the various weight loss events by TGA, which was consistent with the target study.

Product temperatures remained below the critical temperature of −4° C. prior to reaching a break for all the monitored vials. The center thermocouple product temperatures were all below the target range of −8° C. to −6° C. based on thermal analysis data. Product temperatures reached a steady state after approximately 76 hours in primary drying.

This study demonstrated that the low shelf temperature and high chamber pressure boundary conditions in primary drying with a relatively low chamber pressure in secondary drying achieved finished product similar to the target study.

Study D: High Shelf Temperature, Low Chamber Pressure

This study was the third of four boundary studies to show that the target lyophilization process was safe, effective, and robust. Bulk solution was filled at a target fill volume of 1 mL into approximately 400 vials on one tray. Bulk trays with DMSO were used to emulate full load conditions. Thermocouples were placed into 4 edge vials and 6 center vials. Upon completion of loading, the chamber was evacuated to within 11-13 PSIA to ensure a proper seal of the chamber. The product was freeze dried according to the High Shelf Temperature; Low Chamber Pressure (HL) process parameters. Thus, the chamber pressure remained at 15 microns in secondary drying. The RGA was connected to the lyophilizer at a sample port located at the top of the lyophilizer chamber.

During compounding, the compound of Formula (1) was inspected for chunks and the chunks were broken into smaller pieces prior to addition to the DMSO. Dissolution was completed in approximately 2.5 hours due to a larger chunk forming during addition of the compound to the DMSO.

Figure 16:
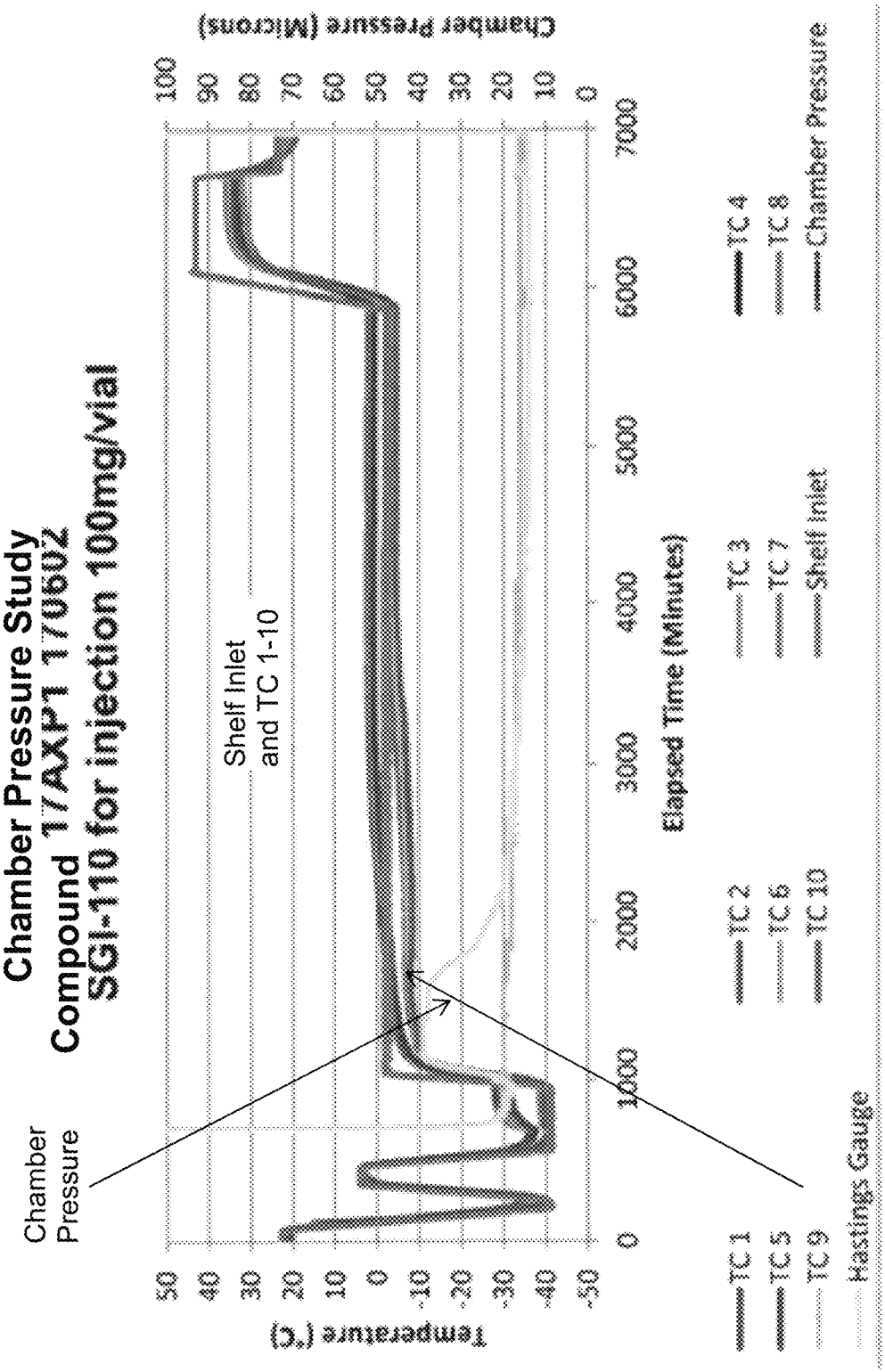
FIG. 16 depicts the lyophilization parameters for a high shelf temperature, low chamber pressure lyophilization process as described herein.

The lyophilization cycle parameter results are shown in FIG. 16.

A summary of the product temperatures at equilibrium are provided in TABLE 32 below:

TABLE 32

| Step | Target Shelf Temperature (° C.) | Product Temperatures[1] (° C.) Average (Min to Max) | |
|---|---|---|---|
|  |  | Center (T/C 5-10) | Edge (T/C 1-4) |
| Loading | 23 | 21.8 (21.6 to 21.9) | 20.6 (20.3 to 20.9) |
| Freeze | −42 | −39.5 (−39.8 to −39) | −35.8 (−36.4 to −34.5) |
| Annealing | 3 | 3 (2.8 to 3.1) | 3 (2.9 to 3.2) |
| Freeze[2] | −42 | −40.4 (−40.7 to −40.1) | −37.2 (−37.7 to −36) |
| Freeze | −42 | −39.1 (−39.7 to −38.6) | −30.1 (−32.1 to −28) |
| Primary Drying | −3 | −3.8 (−4.8 to −3.2) | 1.3 (0.6 to 2) |
| "Break" | — | −6.5 (−7 to −5.7) | −2.2 (−3 to −1.2) |
| Secondary Drying | 43 | 35.1 (34 to 35.8) | 32.8 (31.8 to 34) |

[1]Product Temperatures indicate temperature at end of segment.
[2]Indicates product temperatures immediately prior to evacuation.

A summary of product break temperatures is shown in TABLE 33 below:

TABLE 33

| Center | | | Edge | | |
|---|---|---|---|---|---|
| Thermocouple | Temperature (° C.) | Time (hours) | Thermocouple | Temperature (° C.) | Time (hours) |
| 5-center | 6.6 | 21.1 | 1-edge | −2.3 | 15 |
| 6-center | −7 | 21.1 | 2-edge | −1.2 | 16.3 |
| 7-center | −6.6 | 27.3 | 3-edge | −2.3 | 16.8 |
| 8-center | −5.7 | 28.3 | 4-edge | −3 | 15.4 |
| 9-center | −6.7 | 29.3 | | | |
| 10-center | −6.6 | 37.4 | | | |
| Average | −6.5 | 27.4 | Average | −2.2 | 15.9 |
| Minimum | −7 | 21.1 | Minimum | −3 | 15 |
| Maximum | −5.7 | 37.4 | Maximum | −1.2 | 16.8 |

Figure 17:
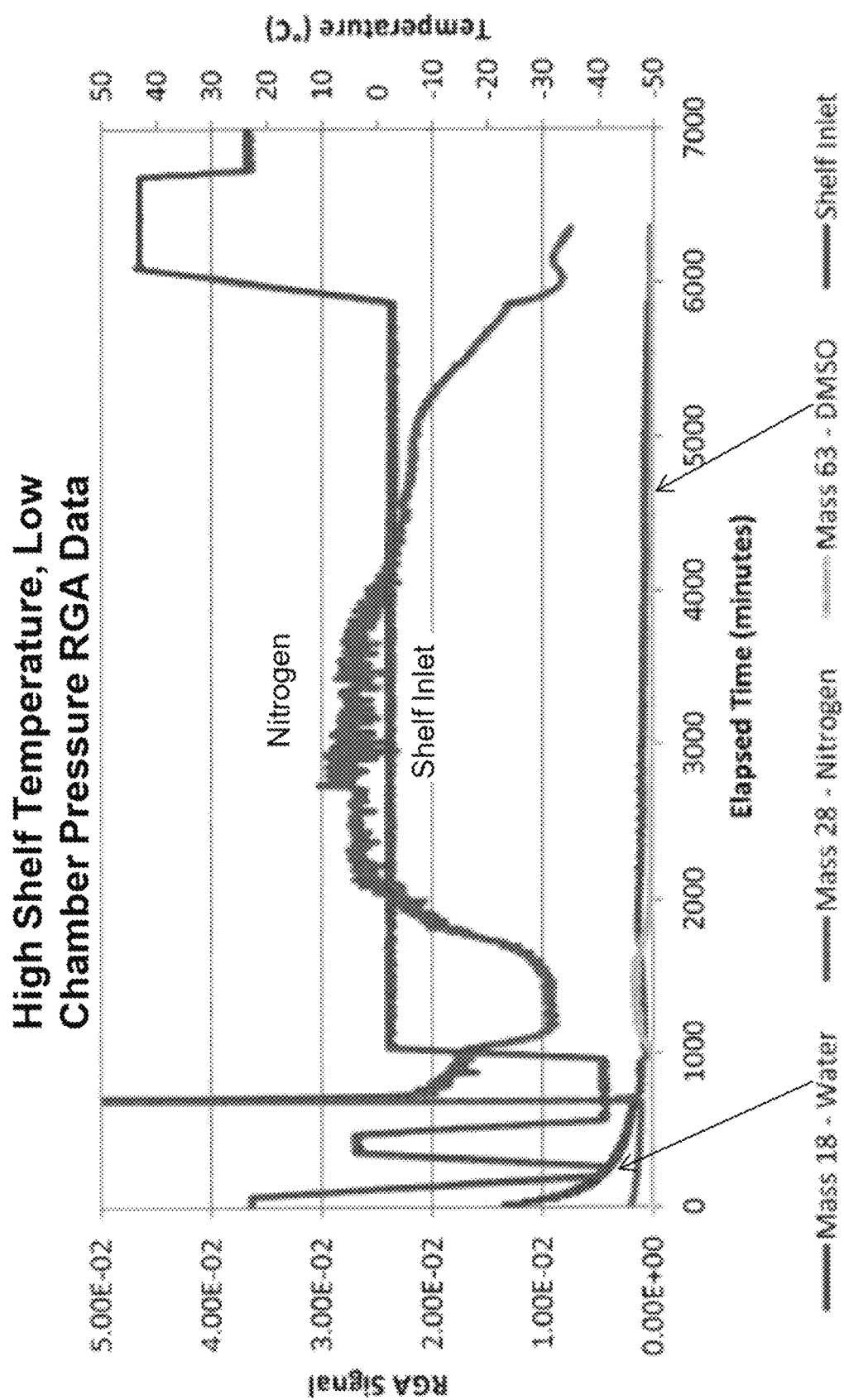
FIG. 17 depicts the residual gas analyzer results for a high shelf temperature, low chamber pressure lyophilization process as described herein.

The RGA data are shown in FIG. 17. The RGA data showed an increase in the DMSO signal at the beginning of primary drying. The DMSO levels returned to baseline levels after approximately 49 hours in primary drying.

Figure 18:
FIG. 18 provides a top view of a lyophilized product for a high shelf temperature, low chamber pressure lyophilization process as described herein.

At the completion of the study, a 100% inspection for physical appearance was performed. Reconstitution was performed on 9 vials. Turbidity testing was performed by pooling 3 reconstituted vials per sample. DSC and TGA were performed on two vials. FIG. 18 shows the top view of a vial of the lyophilized product. Physical appearance for the product vials showed a uniform, dense, white cake with uniform shrinkage around the sides.

Reconstitution was performed by extruding 1 mL of the diluent into each vial using a vial adapter or syringe and allowing the vials to sit undisturbed until clear. All the samples resulted in clear and colorless solutions. Reconstitution times are reported in minutes for this study. TABLE 34 provides the average reconstitution time for this study. Reconstitution took about 16 to 18 minutes for the solution to clear. Turbidity testing on all samples showed NTU values below 3, which are considered a clear solution with no more turbidity than the diluent.

TABLE 34

| Average Recon Time (min) | Turbidity (NTU) |
|---|---|
| 16.5 to 18 | (0.857, 0.793, 2.29) |

The TGA analysis results are provided in TABLE 35 below.

TABLE 35

| Vial | Weight Loss (% w/w) | Temperature Range (° C.) |
|---|---|---|
| 1 | 2.2 | 31 to 76 |
|   | 4.77 | 76 to 122 |
|   | 10.15 | 122 to 195 |
|   | Total: 17.12 | |
| 2 | 1.65 | 32 to 72 |
|   | 6.42 | 72 to 135 |
|   | 9.4 | 135 to 198 |
|   | Total: 17.47 | |

Figure 19:
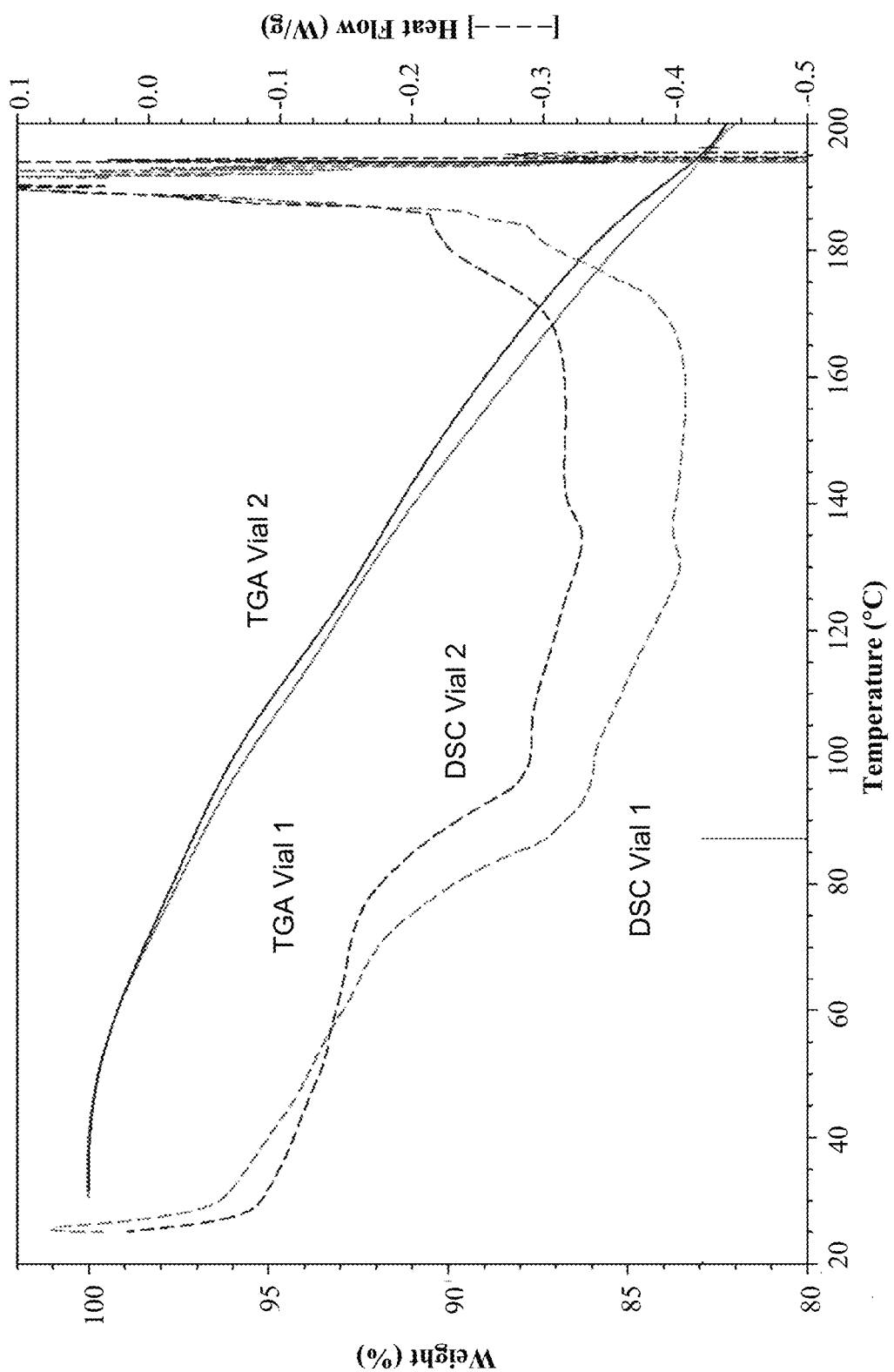
FIG. 19 provides an overlay of differential scanning calorimetry and thermogravimetric analysis thermograms for a high shelf temperature, low chamber pressure lyophilization process as described herein.

The DSC results are provided in FIG. 19 below. FIG. 19 provides an overlay between the DSC and TGA thermograms. TGA results showed approximately 17% w/w mass loss. The DSC showed a shift in baseline that correlated to the various weight loss events by TGA, which was consistent with the target study.

Product temperatures remained below the critical temperature of −4° C. prior to reaching a break for all the monitored vials. The edge thermocouples had break temperatures between −3° C. and −1° C.; however, there no effect on the finished product was detected. The center thermocouple product temperatures were all on the warmer end of the target range of −8° C. to −6° C., as recommended, based on thermal analysis data. Product temperatures reached a steady state after approximately 51 hours in primary drying.

This study demonstrated that the low shelf temperature and high chamber pressure boundary conditions with the chamber pressure lower than 25 microns in secondary drying achieved finished product similar to the target study.

Study E: Low Shelf Temperature, Low Chamber Pressure

This study was the fourth of four boundary studies to show that the target lyophilization process was safe, effective, and robust. Bulk solution was filled at a target fill volume of 1 mL into approximately 400 vials on one tray. Bulk trays with DMSO were used to emulate full load conditions. Thermocouples were placed into 4 edge vials and 6 center vials. Upon completion of loading, the chamber was evacuated to within 11-13 PSIA to ensure a proper seal of the chamber. The product was freeze dried according to the Low Shelf Temperature; Low Chamber Pressure (LL) process parameters. Thus, the chamber pressure remained at 15 microns in secondary drying.

During compounding, one of the lots of the compound of Formula (1) took about seven hours to achieve complete dissolution, while another lot of the compound of Formula (1) took slightly less than 2.5 hours. The rate of dissolution was attributed to the low volume formulated for the first lot and the mixing achieved in the vessel by the magnetic stir bar as the first lot had previously dissolved in as little as 1 hour.

Figure 20:
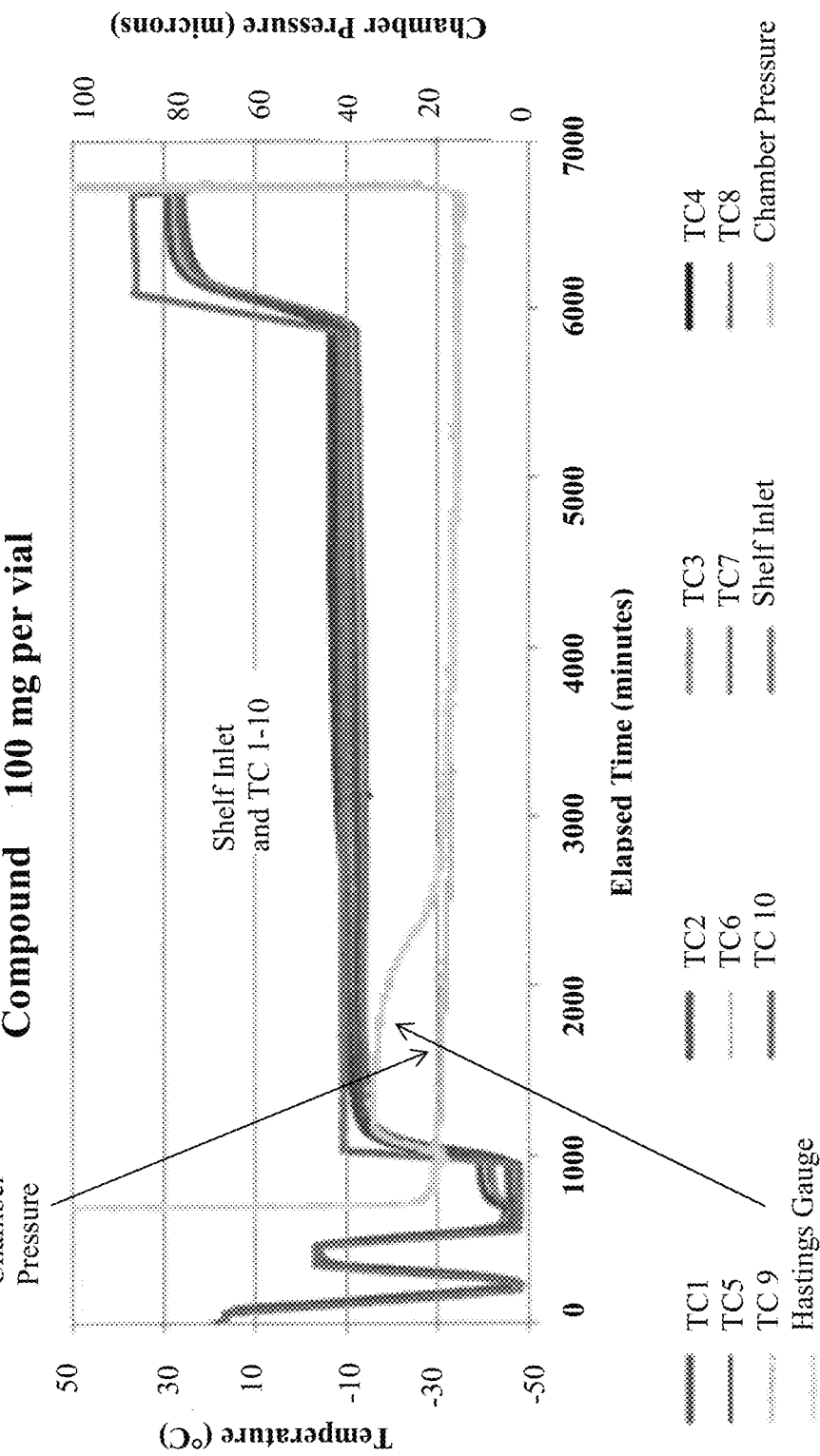
FIG. 20 depicts the lyophilization parameters for a low shelf temperature, low chamber pressure lyophilization process as described herein.

The lyophilization cycle parameter results are shown in FIG. 20.

A summary of the product temperatures at equilibrium are provided in TABLE 36 below:

TABLE 36

| Step | Target Shelf Temperature (° C.) | Product Temperatures[1] (° C.) Average (Min to Max) | |
|---|---|---|---|
| | | Center (T/C 5-10) | Edge (T/C 1-4) |
| Loading | 17 | 15.9 (15.7 to 16) | 15.7 (15.6 to 15.7) |
| Freeze | −48 | −45.8 (−46.5 to −45.1) | −44.8 (−45.6 to −43.6) |
| Annealing | −3 | −4.2 (−4.3 to 4.1) | −4.1 (−4.2 to −4.1) |
| Freeze[2] | −48 | −46.8 (−47.1 to −46.3) | −45.9 (−46.4 to −45.1) |
| Freeze | −48 | −45.8 (−46.3 to −45.2) | −40.4 (−41.8 to −39.1) |
| Primary Drying | −9 | −10.7 (−12.2 to −9.7) | −7 (−7.8 to −6.2) |
| "Break" | — | −13.1 (−14.2 to −12.3) | −9.9 (−10.8 to −9.5) |
| Secondary Drying | 37 | 28 (26.2 to 29.3) | 27.4 (26 to 28.3) |

[1]Product Temperatures indicate temperature at end of segment.
[2]Indicates product temperatures immediately prior to evacuation.

A summary of product break temperatures is shown in TABLE 37 below:

TABLE 37

| Center | | | Edge | | |
|---|---|---|---|---|---|
| Thermocouple | Temperature (° C.) | Time (hours) | Thermocouple | Temperature (° C.) | Time (hours) |
| 5-center | −12.6 | 26.7 | 1-edge | −9.6 | 25.3 |
| 6-center | −13.1 | 26.7 | 2-edge | −9.6 | 26.1 |
| 7-center | −13.4 | 50.9 | 3-edge | −10.8 | 27.9 |
| 8-center | −14.2 | 40.4 | 4-edge | −9.5 | 29.6 |
| 9-center | −12.7 | 52.6 | | | |
| 10-center | −12.3 | 44.4 | | | |
| Average | −13.1 | 40.3 | Average | −9.9 | 27.2 |
| Minimum | −14.2 | 26.7 | Minimum | −10.8 | 25.3 |
| Maximum | −12.3 | 52.6 | Maximum | −9.5 | 29.6 |

Figure 21:
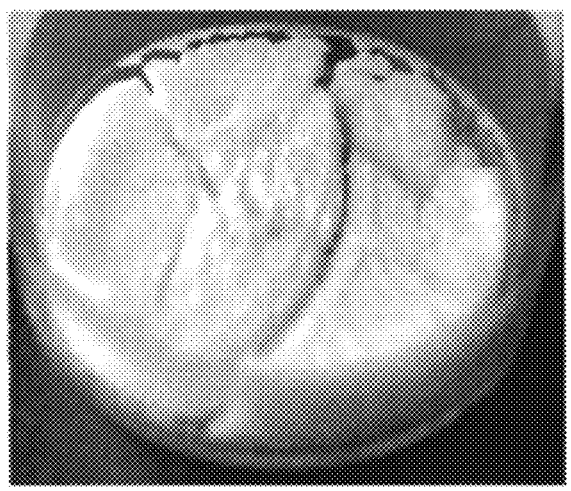
FIG. 21 PANEL A and FIG. 21 PANEL B provides a top view of a lyophilized product for Lot 1 and Lot 2 of a compound of Formula (1), respectively, used in a low shelf temperature, high chamber pressure lyophilization process as described herein.
Figure 21:
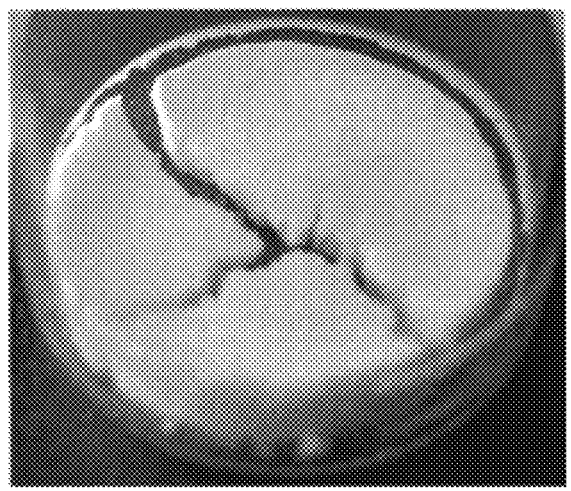

At the completion of the study, a 100% inspection for physical appearance was performed. Reconstitution was performed on 9 vials. Turbidity testing was performed by pooling 3 reconstituted vials per sample. DSC and TGA were performed on two vials per sublot. FIG. 21 PANEL A shows the top view of a vial of the lyophilized product from the first lot of a compound of Formula (1), which had difficulty dissolving, and FIG. 21 PANEL B shows the top view of a vial of the lyophilized product from the second lot, which dissolved faster than the first lot of a compound of Formula (1). Physical appearance for the product vials showed a uniform, dense, white cake with uniform shrinkage around the sides.

Reconstitution was performed by extruding 1 mL of the diluent into each vial using a vial adapter or syringe and allowing the vials to sit undisturbed until clear. All the samples resulted in clear and colorless solutions. Reconstitution times are reported in minutes for this study. TABLE 38 provides the average reconstitution time for this study. Reconstitution took 17 minutes for both sublots. Turbidity testing on all samples showed NTU values below 3, which are considered a clear solution with no more turbidity than the diluent.

TABLE 38

| Average Recon Time (min) | Turbidity (NTU) |
|---|---|
| Lot 1: 17 | (0.799, 0.833, 0.756) |
| Lot 2: 17 | (0.795, 0.808, 0.867) |

The TGA analysis results are provided in TABLE 39 below.

TABLE 39

| Vial | Weight Loss (% w/w) | Temperature Range (° C.) |
|---|---|---|
| Lot 1: Vial 1 | 8.42 | 31 to 98 |
|  | 4.03 | 98 to 133 |
|  | 9.73 | 133 to 198 |
|  | Total: 22.18 |  |
| Lot 1: Vial 2 | 2.15 | 32 to 74 |
|  | 5.29 | 74 to 123 |
|  | 10.37 | 123 to 196 |
|  | Total: 17.81 |  |
| Lot 2: Vial 1 | 6.28 | 32 to 92 |
|  | 4.18 | 92 to 129 |
|  | 9.34 | 129 to 197 |
|  | Total: 19.8 |  |
| Lot 2: Vial 2 | 4.38 | 32 to 84 |
|  | 5.5 | 84 to 133 |
|  | 9.36 | 133 to 197 |
|  | Total: 19.24 |  |

Figure 22:
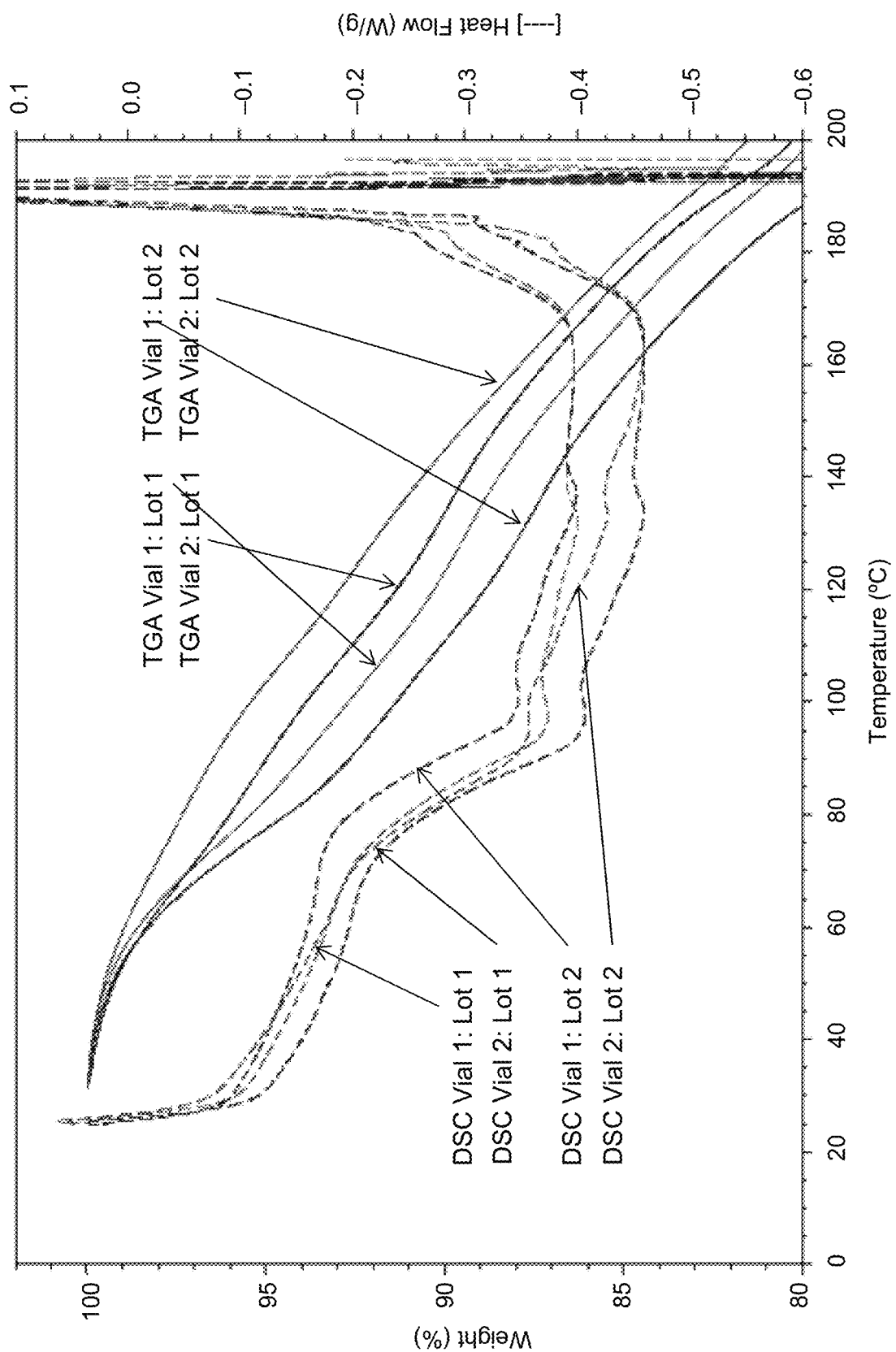
FIG. 22 provides an overlay of differential scanning calorimetry and thermogravimetric analysis thermograms for a low shelf temperature, low chamber pressure lyophilization process as described herein.

The DSC results are provided in FIG. 22 below. FIG. 22 provides an overlay between the DSC and TGA thermograms. TGA results showed more variability for the first lot mass loss but the second lot was consistent at approximately 19% w/w. The variability was likely due to the lower shelf temperature and lower chamber pressure as these conditions would reduce the desorption rate of the DMSO. No impact to the product was observed as the residual DMSO levels would still be within the acceptable levels for the compound of Formula (1) for Injection. The DSC showed a shift in baseline that correlated to the various weight loss events by TGA, which shift was consistent with the target study results.

Product temperatures remained below the critical temperature of −4° C. prior to reaching a break for all the monitored vials. The product temperatures were all below the target range of −8° C. to −6° C., as recommended, based on thermal analysis data. Product temperatures had nearly reached a steady state after about 80.5 hours in primary drying.

This study demonstrated that the low shelf temperature and low chamber pressure boundary conditions with the chamber pressure slightly below 25 microns in secondary drying achieved finished product similar to the target study.

Study F: Target Study

The objective of this study was to reproduce the target lyophilization process and to demonstrate that the target lyophilization process was safe, effective, and robust. Bulk solution was filled at a target fill volume of 1 mL into approximately 175 vials on one tray. Bulk trays with DMSO were used to emulate full load conditions. Thermocouples were placed into 4 edge vials and 6 center vials. Upon completion of loading, the chamber was evacuated to within 11-13 PSIA to ensure a proper seal of the chamber. The product was freeze dried according to the target process parameters in TABLE 18.

During compounding, Lot 1 of the compound of Formula (1) took about 30 minutes to achieve complete dissolution, while Lot 2 took about 1.5 hours.

Figure 23:
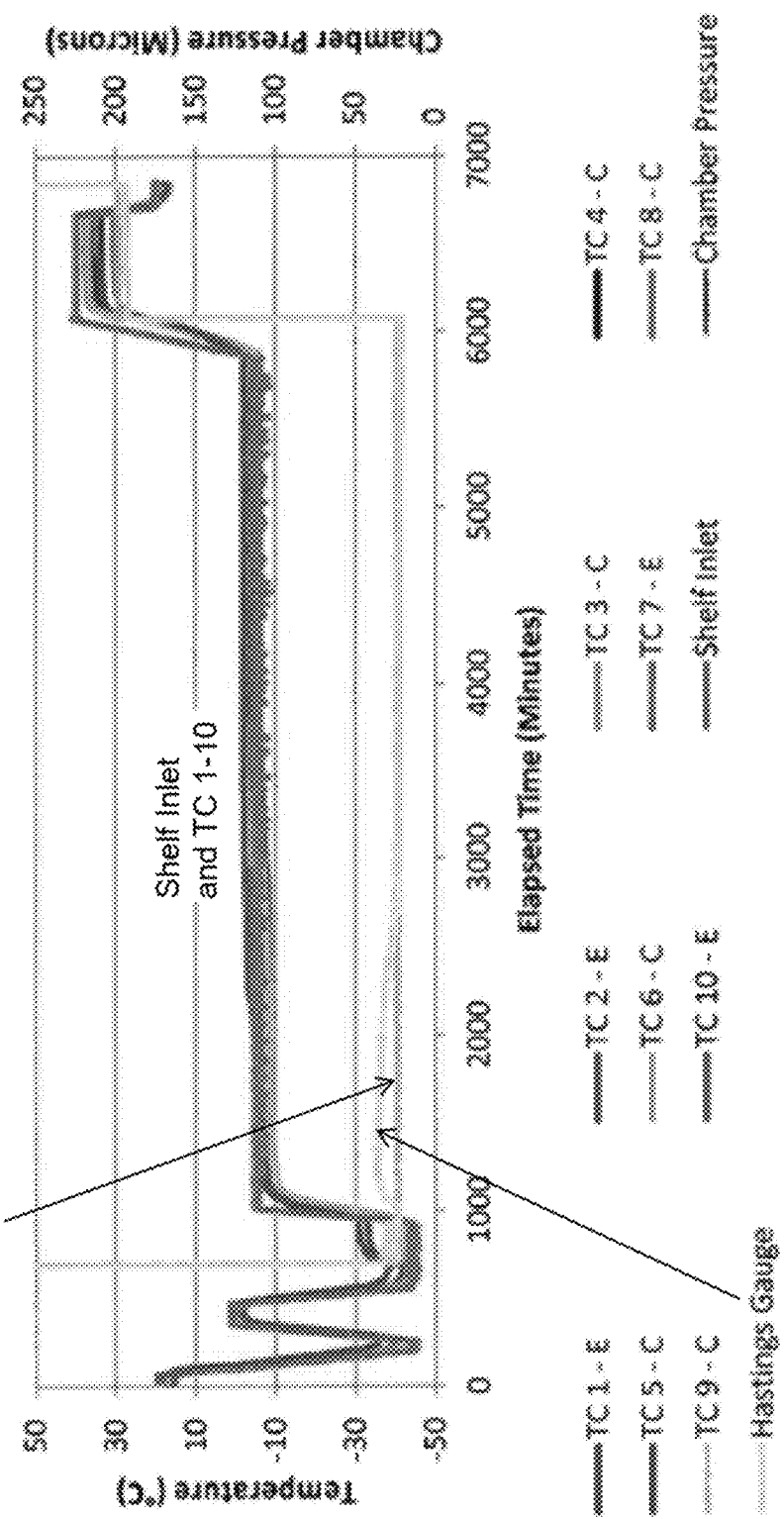
FIG. 23 depicts the lyophilization parameters for a target lyophilization process described herein.

The lyophilization cycle parameter results are shown in FIG. 23.

A summary of the product temperatures at equilibrium are provided in TABLE 40 below:

TABLE 40

| | | Product Temperatures[1] (° C.) Average (Min to Max) | |
|---|---|---|---|
| Step | Target Shelf Temperature (° C.) | Center (T/C 5-10) | Edge (T/C 1-4) |
| Loading | 20 | 18.6 (18.3 to 18.9) | 17.5 (15.1 to 18.5) |
| Freeze | −45 | −42.7 (−43 to −42) | −39.8 (−41.6 to −36) |
| Annealing | 0 | 0.4 (0.1 to 0.7) | −0.4 (−2.1 to 0.4) |
| Freeze[2] | −45 | −43.4 (−43.6 to −43) | −41.4 (−42.6 to −38.8) |
| Freeze | −45 | −42.4 (−42.7 to −42) | −35.1 (−39.1 to −30.6) |
| Primary Drying | −6 | −5.6 (−6.2 to −5.2) | −3.3 (−4.4 to −2.1) |
| "Break" | — | −8 (−8.5 to −7.5) | −5.6 (−6.4 to −4.4) |
| Secondary Drying | 40 | 37 (36.6 to 37.4) | 33.7 (30.1 to 36.1) |

[1]Product Temperatures indicate temperature at end of segment.
[2]Indicates product temperatures immediately prior to evacuation.

A summary of product break temperatures is shown in TABLE 41 below:

TABLE 41

| Center | | | Edge | | |
|---|---|---|---|---|---|
| Thermo-couple | Temperature (° C.) | Time (hours) | Thermo-couple | Temperature (° C.) | Time (hours) |
| 3-center | −7.8 | 21.1 | 1-edge | −6.3 | 26 |
| 4-center | −7.5 | 25.4 | 2-edge | −6.4 | 25.9 |
| 5-center | −8.5 | 27.3 | 7-edge | −4.4 | 23.9 |
| 6-center | −8.4 | 19.5 | 10-edge | −5.1 | 14.8 |
| 8-center | −7.7 | 24.4 | | | |
| 9-center | −8 | 25.9 | | | |
| Average | −8 | 23.9 | Average | −5.6 | 22.6 |
| Minimum | −8.5 | 19.5 | Minimum | −6.4 | 14.8 |
| Maximum | −7.5 | 27.3 | Maximum | −4.4 | 26 |

Figure 24:
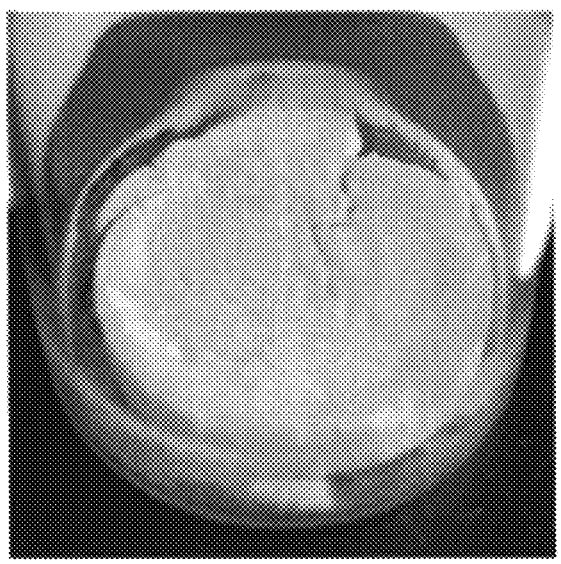
FIG. 24 PANEL A and FIG. 24 PANEL B provides a top view of a lyophilized product for Lot 1 and Lot 2 of a compound of Formula (1), respectively, used in a target lyophilization process as described herein.
Figure 24:
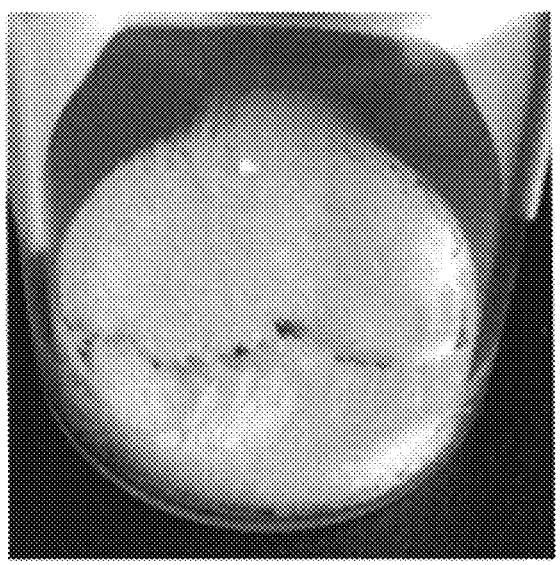

At the completion of the study, a 100% inspection for physical appearance was performed. Reconstitution was performed on 9 vials. Turbidity testing was performed by pooling 3 reconstituted vials per sample. DSC and TGA were performed on two vials per sublot. FIG. 24 PANEL A shows the top view of a vial of the lyophilized product from the first lot of a compound of Formula (1), and FIG. 24 PANEL B shows the top view of a vial of the lyophilized product from the second lot. Physical appearance for the product vials showed a uniform, dense, white cake with uniform shrinkage around the sides.

Reconstitution was performed by extruding 1 mL of the diluent into each vial using a vial adapter or syringe and allowing the vials to sit undisturbed until clear. All the samples resulted in clear and colorless solutions. Reconstitution times are reported in minutes for this study. TABLE 42 provides the average reconstitution time for this study. Reconstitution took about 17-18 minutes for the solution to clear. The reconstitution time was consistent or slightly shorter than previous studies with the compound of Formula (1) Injection. Turbidity testing showed NTU values below 1 NTU for Lot 1 and around 10 NTU for Lot 2, which are consistent with previous values for these two lots of API.

TABLE 42

| Average Recon Time (min) | Turbidity (NTU) |
|---|---|
| Lot 1: 17.3 | (0.513, 0.6, 0.638) |
| Lot 2: 18 | (9.04, 11.9, 10.5) |

The TGA analysis results are provided in TABLE 43 below.

TABLE 43

| Vial | Weight Loss (% w/w) | Temperature Range (° C.) |
|---|---|---|
| Lot 1 | 5 | 27 to 64 |
|  | 5.09 | 64 to 126 |
|  | 8.84 | 126 to 195 |
|  | Total: 18.93 |  |
| Lot 2 | 6.36 | 29 to 71 |
|  | 4.65 | 71 to 122 |
|  | 8.81 | 122 to 193 |
|  | Total: 19.82 |  |

Figure 25:
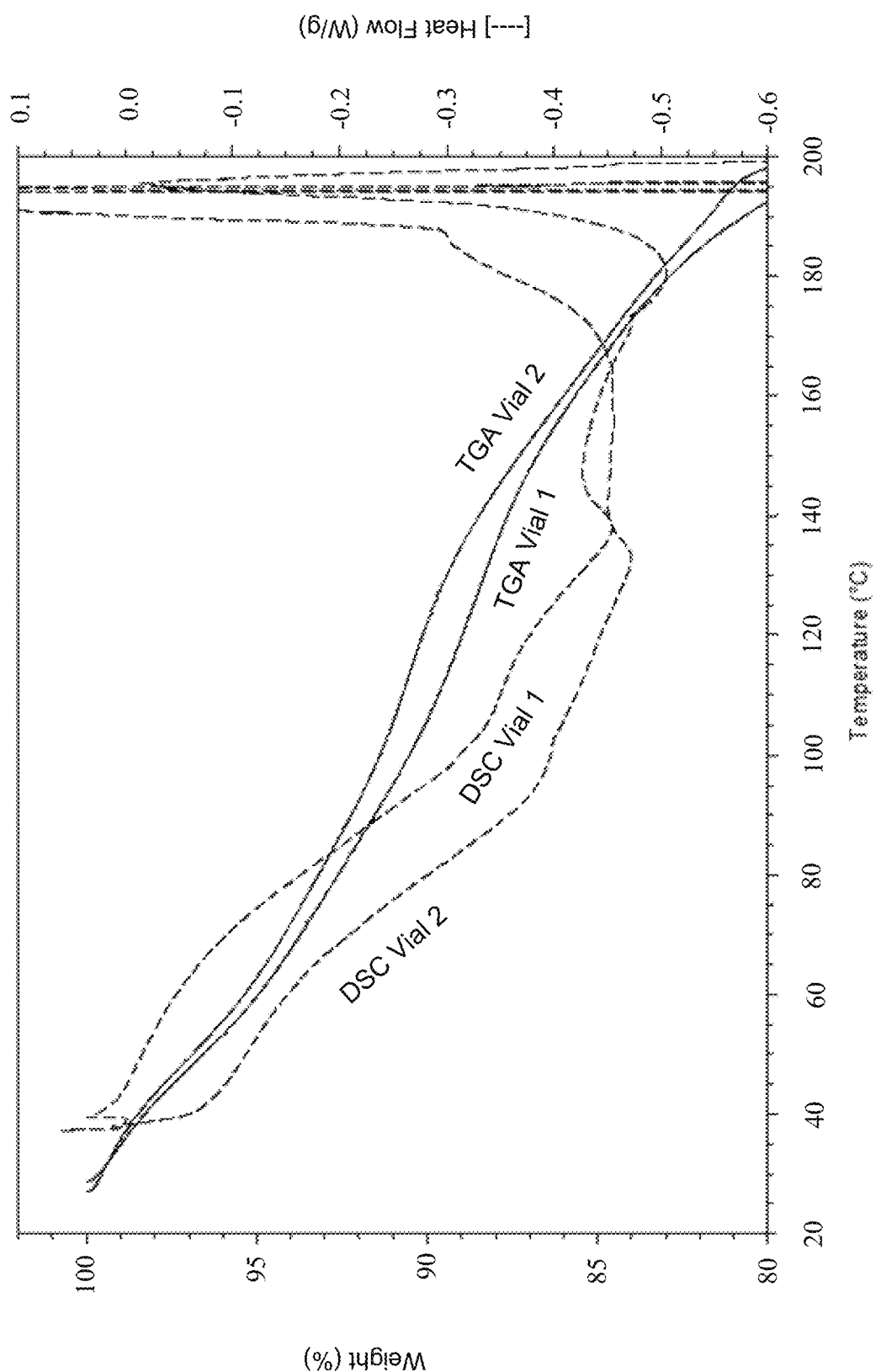
FIG. 25 provides an overlay of differential scanning calorimetry and thermogravimetric analysis thermograms for a target lyophilization process as described herein.

The DSC results are provided in FIG. 25 below. FIG. 25 provides an overlay between the DSC and TGA thermograms. TGA results showed approximately 19% w/w mass loss. The DSC showed a shift in baseline that correlated to the various weight loss events by TGA, which shift suggests the DSC changes were related to the evolution of residual DMSO from the samples.

Product reached a steady state after about 40 hours in primary drying.

This study demonstrated that the recommended target parameters achieved a product with consistent residual DMSO levels and low turbidity upon reconstitution.

Study G: Low Shelf Temperature, High Chamber Pressure

The objective of this study was to be the LH boundary study to show that the lyophilization process was safe, effective, and robust. Bulk solution was filled at a target fill volume of 1 mL into 140 vials on one tray. The remainder of the vials and bulk trays were filled with DMSO to emulate full load conditions. Thermocouples were placed into 4 edge vials and 6 center vials; however, one of the thermocouples in the center vials did not record throughout the lyophilization process. Upon completion of loading, the chamber was evacuated to within 11-13 PSIA to ensure a proper seal of the chamber. The product was freeze dried according to the LH process parameters in TABLE 18.

During compounding, the compound of Formula (1) was checked for larger chunks. The lot of the compound of Formula (1) used in the present study took about 3.3 hours to achieve dissolution.

Figure 26:
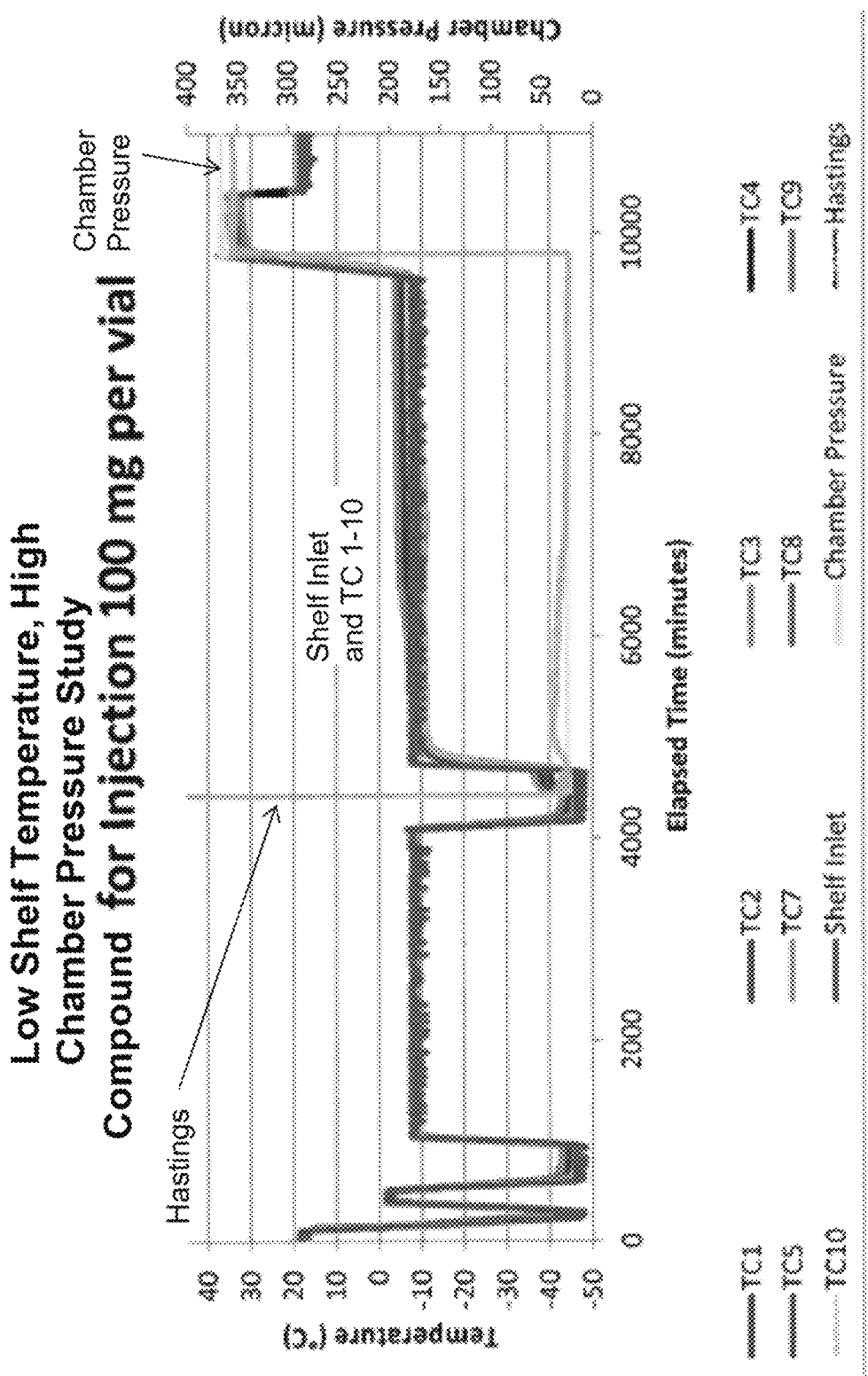
FIG. 26 depicts the lyophilization parameters for a low shelf temperature, high chamber pressure lyophilization process as described herein.

The lyophilization cycle parameter results are shown in FIG. 26. An extended hold occurred at −9° C. with the system near atmospheric pressure. No impact to the study arising from this hold was observed.

A summary of the product temperatures at equilibrium are provided in TABLE 44 below:

TABLE 44

| Step | Target Shelf Temperature (° C.) | Product Temperatures[1] (° C.) Average (Min to Max) | |
|---|---|---|---|
| | | Center (T/C 5-10) | Edge (T/C 1-4) |
| Loading | 17 | 17.8 (18.3 to 18.9) | 17.5 (15.1 to 18.5) |
| Freeze | −48 | −45.2 (−43 to −42) | −39.8 (−41.6 to −36) |
| Annealing | −3 | −2.7 (0.1 to 0.7) | −0.4 (-2.1 to 0.4) |
| Freeze | −48 | −46.1 (−46.2 to −45.8) | −43.6 (−44.5 to −42.9) |
| Extended Hold | −9 | −8.1 (−8.4 to −7.8) | −8.5 (−8.7 to −8.2) |
| Freeze[2] | −48 | −46.3 (−46.4 to −46) | −43.9 (−44.6 to −43.3) |
| Freeze | −48 | −45.1 (−45.5 to −44.8) | −37.9 (−40.1 to −36.2) |
| Primary Drying | −9 | −8.2 (−8.5 to −8) | −4.6 (−5.4 to −3.9) |
| "Break" | — | −10.4 (−10.8 to −10.1) | −8.4 (−9.2 to −7.6) |
| Secondary Drying | 37 | 34.8 (34.5 to 35) | 32.7 (32 to 33.5) |

[1]Product Temperatures indicate temperature at end of segment.
[2]Indicates product temperatures immediately prior to evacuation.

A summary of product break temperatures is shown in TABLE 45 below:

TABLE 45

| Center | | | Edge | | |
|---|---|---|---|---|---|
| Thermocouple | Temperature (° C.) | Time (hours) | Thermocouple | Temperature (° C.) | Time (hours) |
| 5-center | −10.2 | 43.2 | 1-edge | −9.2 | 9.6 |
| 7-center | −10.1 | 42.6 | 2-edge | −7.6 | 25.9 |
| 8-center | −10.2 | 46.5 | 3-edge | −8.2 | 23.9 |
| 9-center | −10.8 | 44.2 | 4-edge | −8.6 | 14.8 |
| 10-center | −10.6 | 44.2 | | | |
| Average | −10.4 | 44.1 | Average | −8.4 | 22.6 |
| Minimum | −10.8 | 42.6 | Minimum | −9.2 | 14.8 |
| Maximum | −10.1 | 46.5 | Maximum | −7.6 | 26 |

At the completion of the study, a 100% inspection for physical appearance was performed. Reconstitution was performed on 9 vials. Turbidity testing was performed by pooling 3 reconstituted vials per sample. DSC and TGA were performed on one vial.

Figure 27:
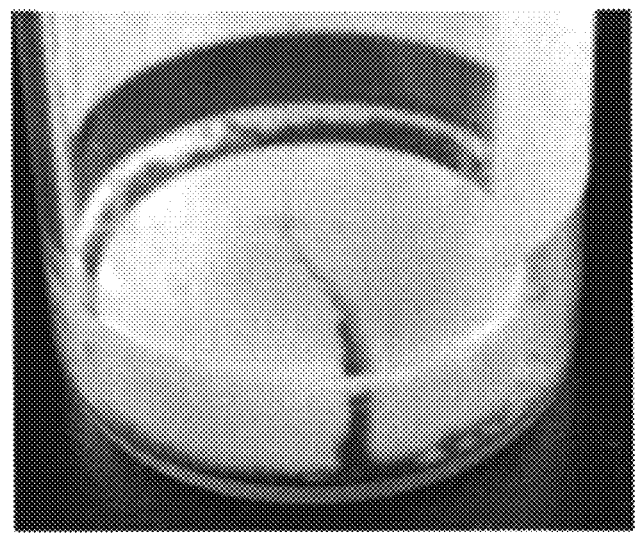
FIG. 27 provides a top view of a lyophilized product for a low shelf temperature, high chamber pressure lyophilization process as described herein.

FIG. 27 shows the top view of a vial of the lyophilized product. Physical appearance for the product vials showed a uniform, dense, white cake with uniform shrinkage around the sides.

Reconstitution was performed by extruding 1 mL of the diluent into each vial using a vial adapter or syringe and allowing the vials to sit undisturbed until clear. All the samples resulted in clear and colorless solutions. Reconstitution times are reported in minutes for this study. TABLE 46 provides the average reconstitution time for this study. Reconstitution took slightly less than 17 minutes for the solution to clear. Turbidity testing on all samples showed NTU values around 15-20 NTU, which values are consistent with previous results for this lot of the compound of Formula (1).

TABLE 46

| Average Recon Time (min) | Turbidity (NTU) |
|---|---|
| 16.7 | (16.9, 16, 19) |

The TGA analysis results are provided in TABLE 47 below.

TABLE 47

| Vial | Weight Loss (% w/w) | Temperature Range (° C.) |
|---|---|---|
| Lot 1 | 3.94 | 27 to 90 |
|  | 3.98 | 90 to 136 |
|  | 5.47 | 136 to 177 |
|  | 3.31 | 177 to 198 |
|  | Total: 16.7 |  |

Figure 28:
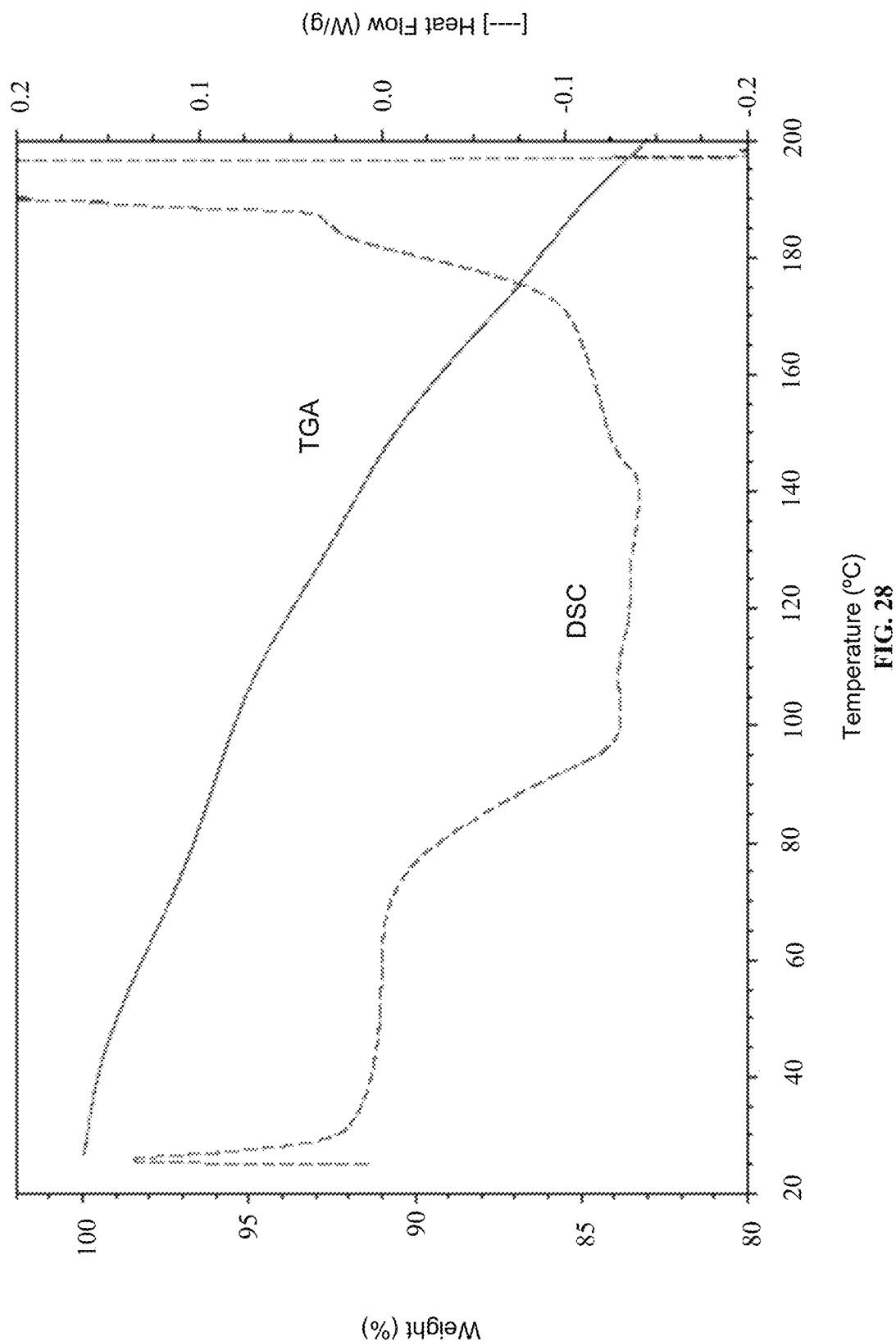
FIG. 28 provides an overlay of differential scanning calorimetry and thermogravimetric analysis thermograms for a low shelf temperature, high chamber pressure lyophilization process as described herein.

The DSC results are provided in FIG. 28 below. FIG. 28 provides an overlay between the DSC and TGA thermograms. TGA results showed approximately 17% w/w mass loss, which was slightly lower than the results from Target study. The DSC showed a shift in baseline that correlated to the various weight loss events by TGA, which shift was consistent with the target study results.

Product temperatures remained below the critical temperature of −4° C. prior to reaching a break for all the monitored vials. All the product temperatures were below the target range of −8° C. to −6° C. based on thermal analysis data. Product temperatures reached a steady state after approximately 75 hours in primary drying. The hastings gauge returned to match the chamber pressure after approximately 55 hours in primary drying.

This study demonstrated that the low shelf temperature and high chamber pressure boundary conditions achieved finished product similar to the target study.

Study H: High Shelf Temperature, High Chamber Pressure

The objective of this study was to be the HH boundary studies to show that the target lyophilization process was effective and robust. Bulk solution was filled at a target fill volume of 1 mL into 135 vials on one tray. The remaining vials and bulk trays were filled with DMSO to emulate full load conditions. Thermocouples were placed into 3 edge vials and 6 center vials, but one edge thermocouple did not record any data. Upon completion of loading, the chamber was evacuated to within 11-13 PSIA to ensure a proper seal of the chamber. The product was freeze dried according to the HH process parameters in TABLE 18; however, data were not collected during the freezing and annealing steps. The RGA was connected to the lyophilizer at a sample port located at the back of the lyophilizer chamber.

During compounding, the compound of Formula (1) was checked for larger chunks. The lot of the compound of Formula (1) used in the present study took 116 minutes to achieve complete dissolution. The initial bulk solution was placed into storage at 2° C. to 8° C., instead of controlled room temperature and inadvertently froze. A second bulk solution was prepared with a dissolution time of 46 minutes. The second bulk solution was filled into the vials.

Figure 29:
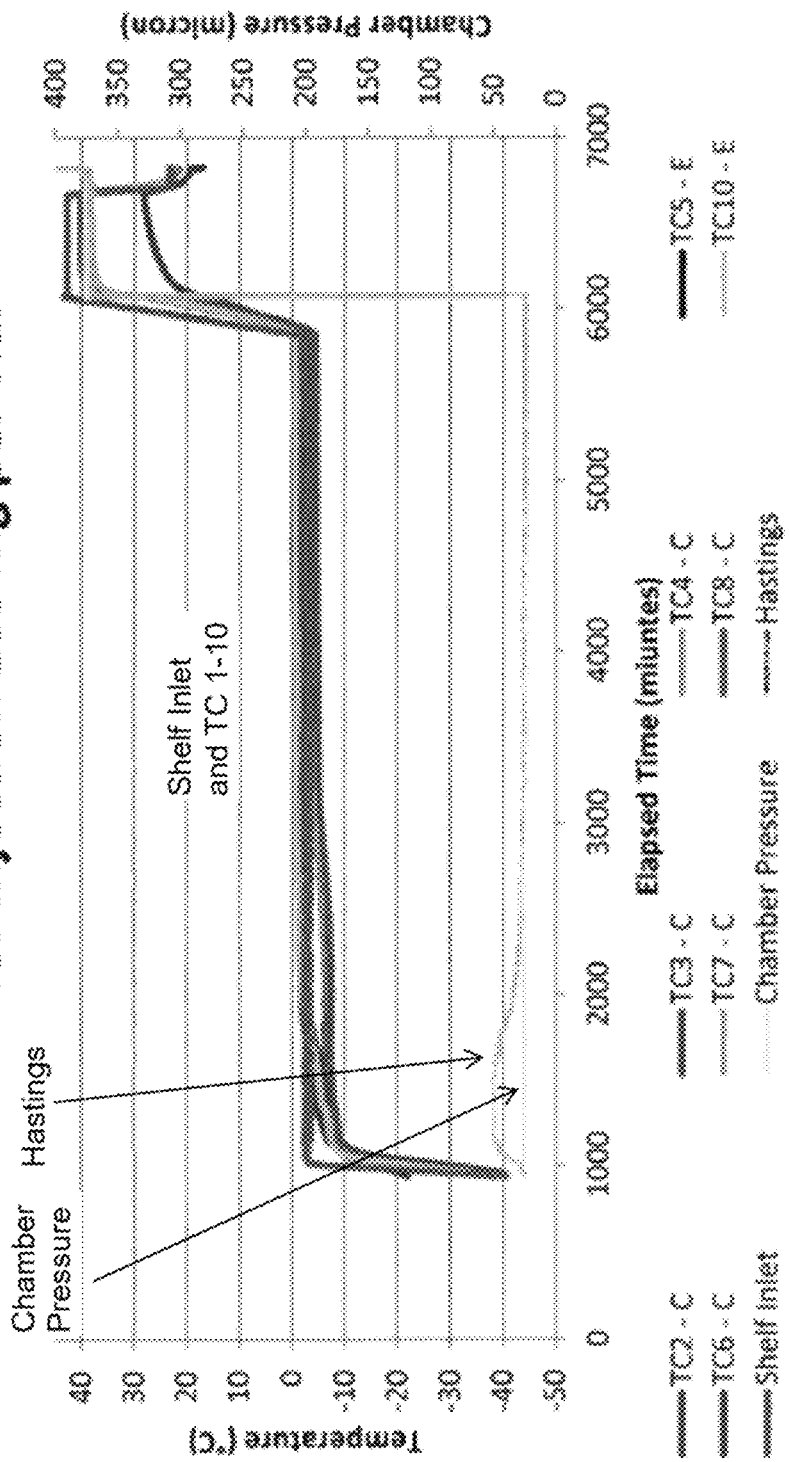
FIG. 29 depicts the lyophilization parameters for a high shelf temperature, high chamber pressure lyophilization process as described herein.

The lyophilization cycle parameter results are shown in FIG. 29. Note: TC-2 was excluded from further data analysis.

A summary of the product temperatures at equilibrium are provided in TABLE 48 below:

TABLE 48

| Step | Target Shelf Temperature (° C.) | Product Temperatures[1] (° C.) Average (Min to Max) | |
|---|---|---|---|
|  |  | Center (T/C 3, 4, 6, 7, 8) | Edge (T/C 5 and 10) |
| Loading | 23 |  |  |
| Freeze | −42 |  |  |
| Annealing | 3 |  |  |
| Freeze | −42 |  |  |
| Freeze | −42 | −40.7 (−41 to −40.4) | (−37.8 to −35.1) |
| Primary Drying | −3 | −4.1 (−4.6 to −3.8) | (−1.5 to −0.6) |
| "Break" | — | −7.1 (−7.5 to −6.6) | (−6.9 to −6.5) |
| Secondary Drying | 43 | 39.9 (39.7 to 40.1) | (38.3 to 39) |

[1]Product Temperatures indicate temperature at end of segment.

Figure 30:
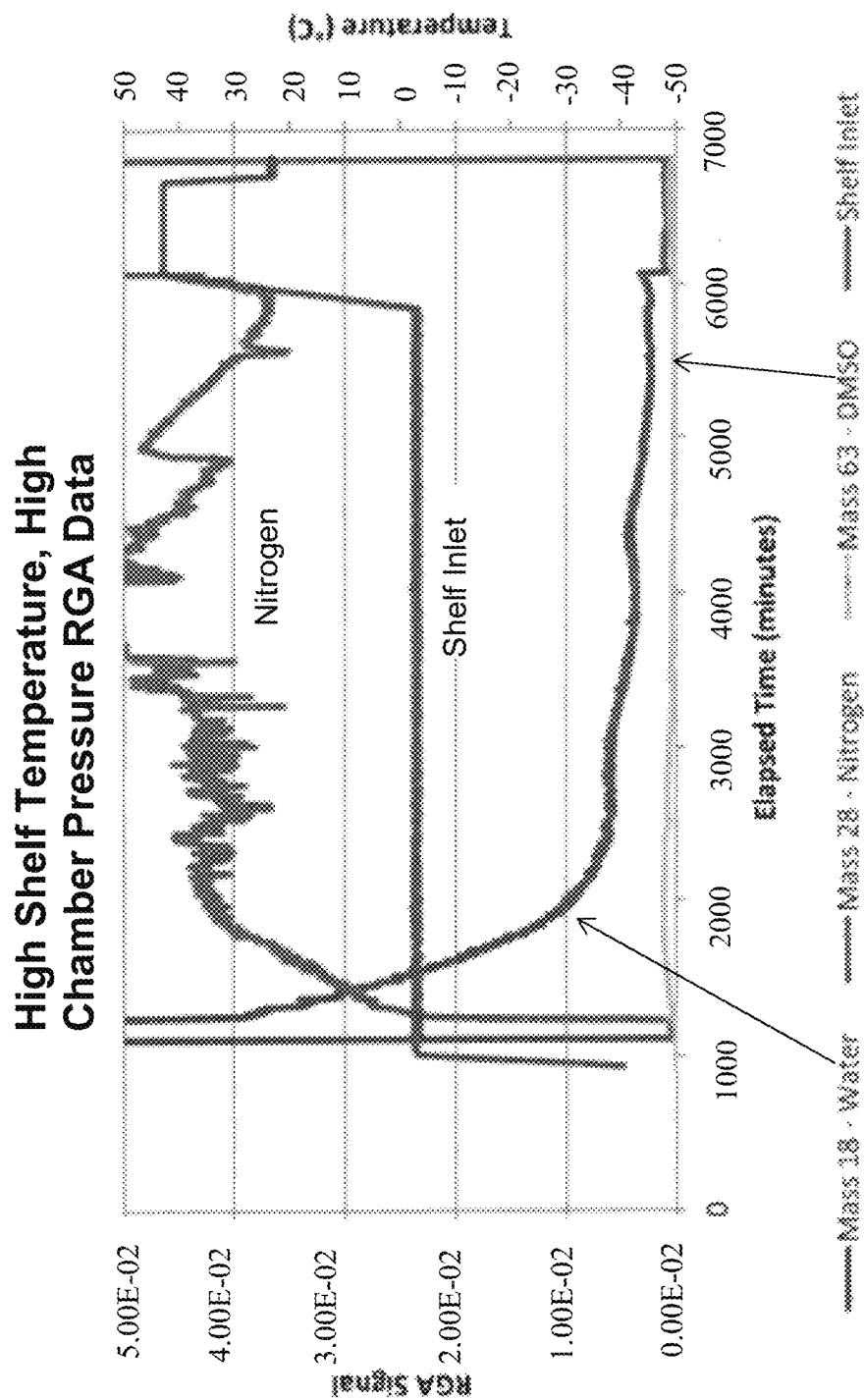
FIG. 30 depicts the residual gas analyzer results for a high shelf temperature, high chamber pressure lyophilization process as described herein.

The RGA data are shown in FIG. 30. The RGA data showed an increase in the DMSO signal at the beginning of primary drying. This DMSO level returned to baseline after approximately 61 hours in primary drying.

A summary of product break temperatures is shown in TABLE 49 below:

TABLE 49

| Center | | | Edge | | |
|---|---|---|---|---|---|
| Thermocouple | Temperature (° C.) | Time (hours) | Thermocouple | Temperature (° C.) | Time (hours) |
| 3 center | −6.6 | 18.1 | 5 edge | −6.5 | 8.1 |
| 4 center | −7.1 | 16.5 | 10 edge | −6.9 | 4.4 |
| 6 center | −7.5 | 19.5 |  |  |  |
| 7 center | −7.2 | 19.9 |  |  |  |
| 8 center | −7.2 | 20.7 |  |  |  |
| Average | −7.1 | 18.9 | Average |  |  |
| Minimum | −7.5 | 16.5 | Minimum | −6.9 | 4.4 |
| Maximum | −6.6 | 20.7 | Maximum | −6.5 | 8.1 |

At the completion of the study, a 100% inspection for physical appearance was performed. Reconstitution was performed on 9 vials. Turbidity testing was performed by pooling 3 reconstituted vials per sample. DSC and TGA were performed on one vial.

Figure 31:
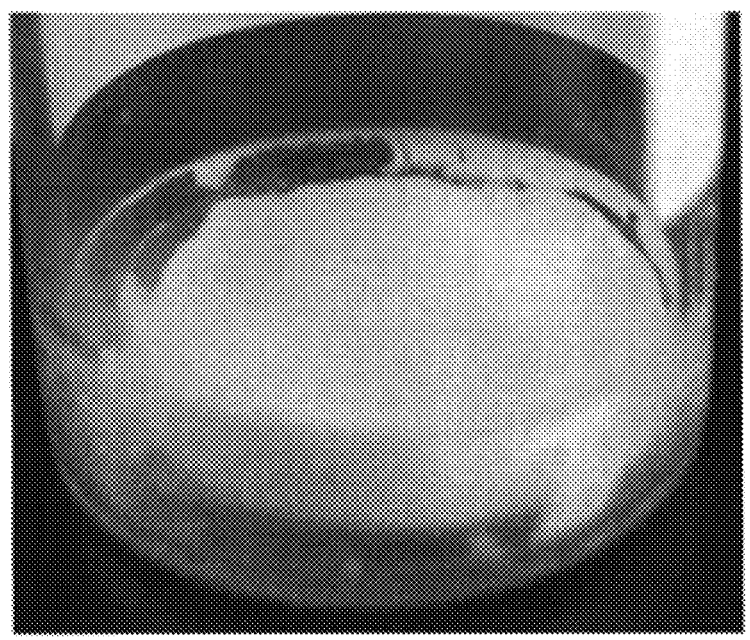
FIG. 31 provides a top view of a lyophilized product for a high shelf temperature, high chamber pressure lyophilization process as described herein.

FIG. 31 shows the top view of a vial of the lyophilized product. Physical appearance for the product vials showed a uniform, dense, white cake with uniform shrinkage around the sides.

Reconstitution was performed by extruding 1 mL of the diluent into each vial using a vial adapter or syringe and allowing the vials to sit undisturbed until clear. All the samples resulted in clear and colorless solutions. Due to the long reconstitution times, reconstitution times are reported in minutes for this study. TABLE 50 provides the average reconstitution time for this study. Reconstitution took about 17 minutes for the solution to fully clear, which was slightly faster than previous results. Turbidity testing on all samples showed NTU values from 3 to 32 NTU. The values were slightly more variable than previous studies but still within the same range consistent with previous results for this lot of the compound of Formula (1).

TABLE 50

| Average Recon Time (min) | Turbidity (NTU) |
|---|---|
| 17.2 | 32.4, 27.2, 2.91 |

The TGA analysis results are provided in TABLE 51 below.

TABLE 51

| Vial | Weight Loss (% w/w) | Temperature Range (° C.) |
|---|---|---|
| 1 | 3.69 | 28 to 87 |
|   | 3.47 | 87 to 125 |
|   | 9.53 | 125 to 194 |
|   | Total: 16.69 | |

Figure 32:
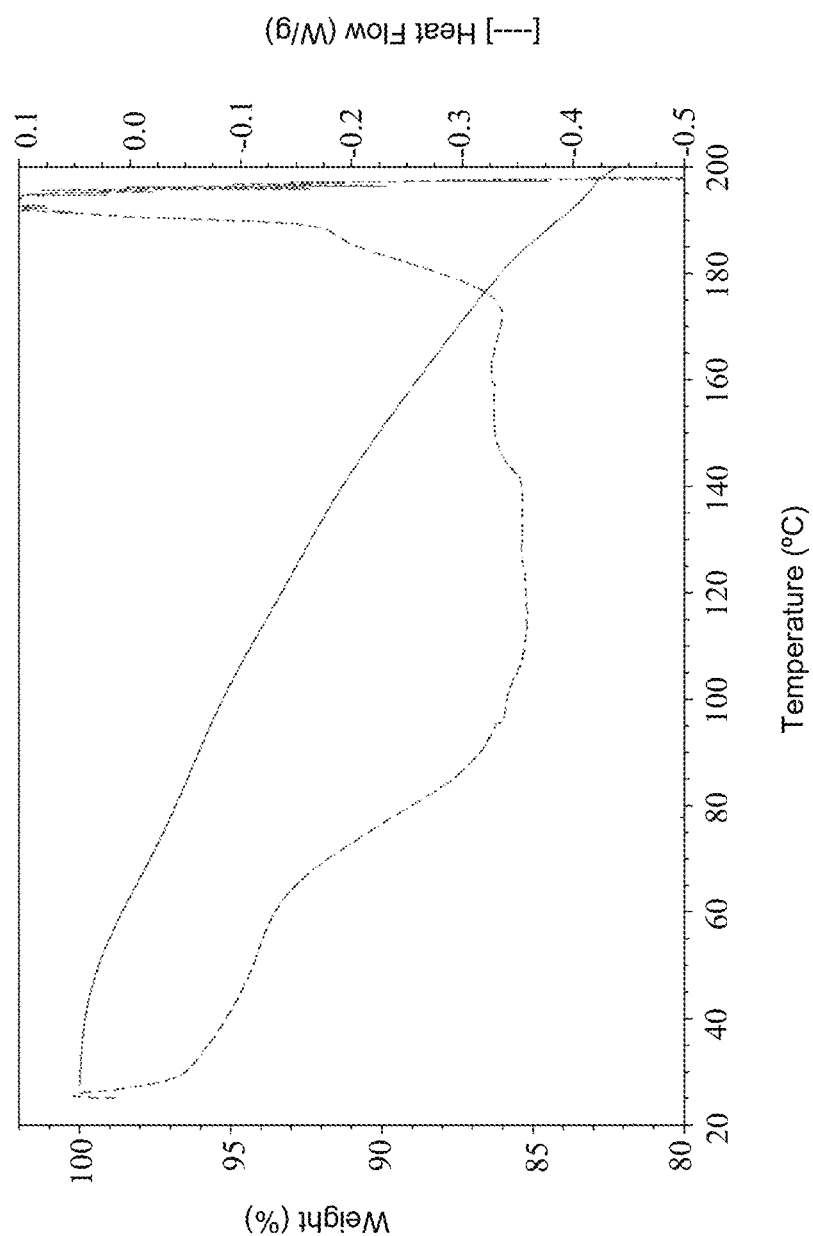
FIG. 32 provides an overlay of differential scanning calorimetry and thermogravimetric analysis thermograms for a high shelf temperature, high chamber pressure lyophilization process as described herein.

The DSC results are provided in FIG. 32 below. FIG. 32 provides an overlay between the DSC and TGA thermograms. TGA results showed approximately 17% w/w mass loss, which was slightly lower than the results from Target study. The DSC showed a shift in baseline that correlated to the various weight loss events by TGA, which shift was consistent with the target study results.

Product temperatures remained below the critical temperature of −4° C. prior to reaching a break for all the center thermocouples. The thermocouple product temperatures were all within a range of −8° C. to −6° C. Product temperatures reached a steady state after approximately 42 hours in primary drying.

This study demonstrated that the high shelf temperature and high chamber pressure boundary conditions achieved finished product similar to the target study.

As described above, for the high shelf temperature, high chamber pressure study, the data during freezing was not collected. Thus, the study was repeated, and the results are provided below.

The cycling parameters used in the repeat of the study are shown in TABLE 52.

TABLE 52

| Step | Shelf Temp. Setpoint (° C.) | Soak Time (hours) | Ramping Rate (° C./hour) | Pressure Set point (micron) |
|---|---|---|---|---|
| Loading | 23 | 1 | | Evacuate to about 12 |
| Freezing | −42 | 1 | 30 | |
| Annealing | 3 | 2 | 30 | PSIA |
| Freezing | −42 | 2 | 30 | 25 |
| Primary Drying | −42 | 4 | 30 | |
|  | −3 | 80.5 | | |
| Secondary Drying | 43 | 20.0 | 12 | 375 |
| Stoppering | 23 | | 30 | 14.7 PSIA |

Figure 33:
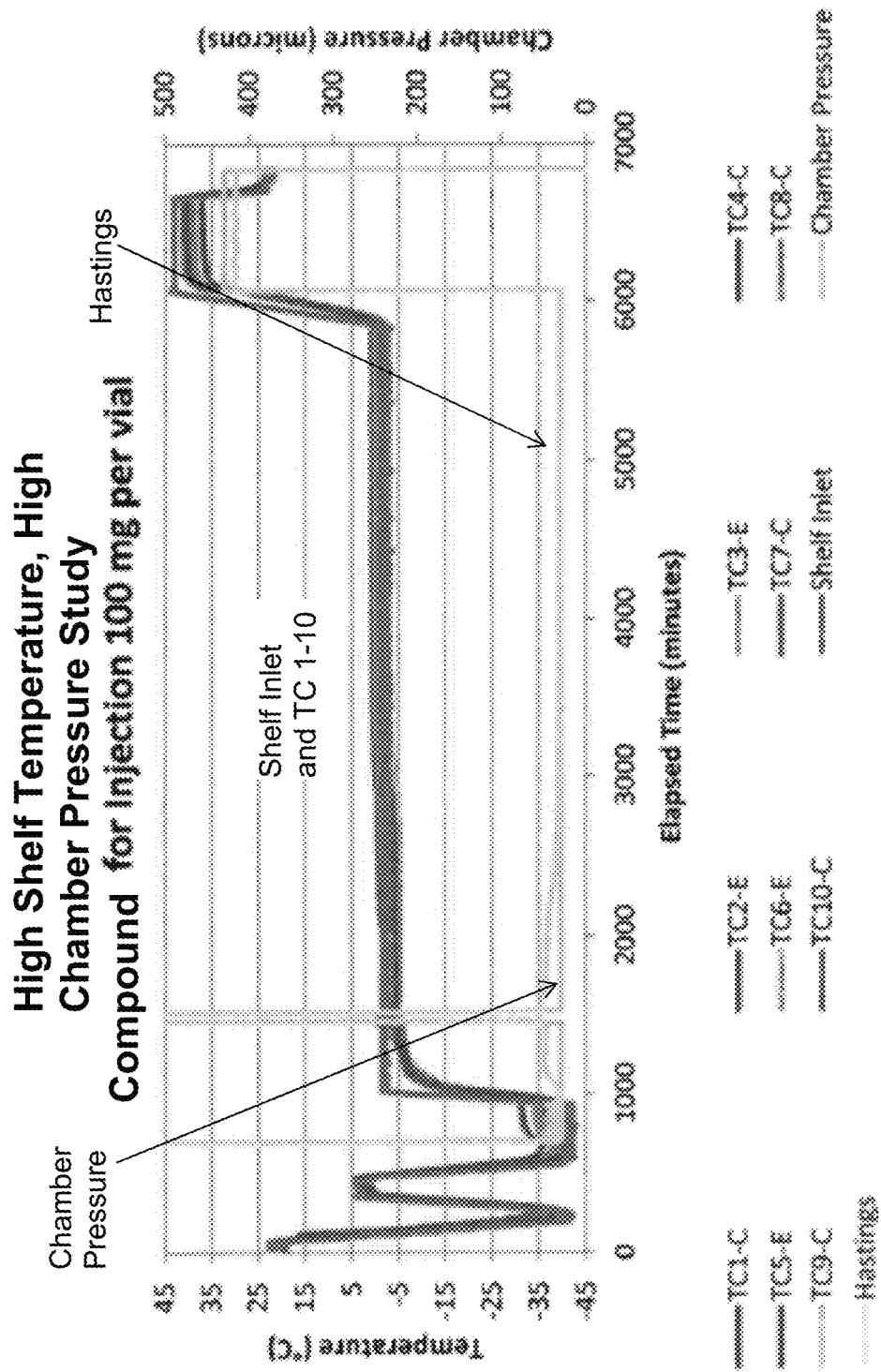
FIG. 33 depicts the lyophilization parameters for a repeated study of a high shelf temperature, high chamber pressure lyophilization process as described herein.

The lyophilization cycle parameters are also provided in FIG. 33.

A summary of the product temperatures at equilibrium are provided in TABLE 53 below:

TABLE 53

| Step | Target Shelf Temperature (° C.) | Shelf Temperature Average (° C.) (Min to Max) | Product Temperatures (° C.) Average (Min to Max) | |
|---|---|---|---|---|
| | | | Center (T/C 1,4, 7-10) | Edge (T/C 2, 3, 5, 6) |
| Loading | 23 | 22.6 (22.6 to 22.6) | 21.9 (21.6 to 22.2) | 17.5 (15.1 to 18.5) |
| Freeze | −42 | −41.4 (−42.2 to −39.1) | −39.9 (−40.5 to −39.4) | −39.8 (−41.6 to −36) |
| Annealing | 3 | 3.8 (3.2 to 4.5) | 3.8 (3.4 to 3.9) | −0.4 (−2.1 to 0.4) |
| Freeze | −42 | −41.3 (−42.7 to −40) | −40.6 (−41 to −40.3) | −43.6 (−44.5 to −42.9) |
| Freeze | −42 | −41.4 (−42.8 to −40.3) | −39.7 (−40.3 to −38.7) | −37.9 (−40.1 to −36.2) |
| Primary Drying | −3 | −2.1 (−5.6 to 0.4) | −2.4 (−2.7 to −1.7) | −4.6 (−5.4 to −3.9) |
| Secondary Drying | 43 | 42.9 (42.7 to 43.6) | 40.9 (40.4 to 41.3) | 38.7 (37.1 to 39.6) |

TABLE 54 provides a summary of the sublimation for the repeated study:

TABLE 54

| Study | "Break" Temperature | "Break" Times | Hastings Gauge[1] |
|---|---|---|---|
| Repeated HH Study | <−3° C. | <30 hours | 42 hours |

[1]Indicates the time the Hastings Gauge reading reached a steady state at chamber pressure during primary drying.

At the completion of the study, a 100 percent inspection for physical appearance was performed. Reconstitution was performed on 9 vials. Turbidity testing was performed by pooling 3 reconstituted vials per sample. DSC and TGA were performed on 1 vial.

Figure 34:
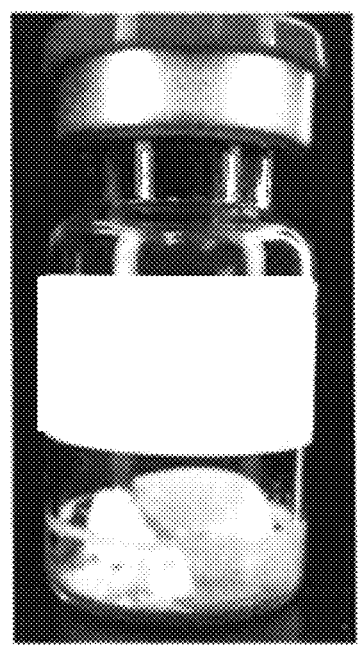
FIG. 34 provides a side view of a lyophilized product for a repeated study of a high shelf temperature, high chamber pressure lyophilization process as described herein.
Figure 35:
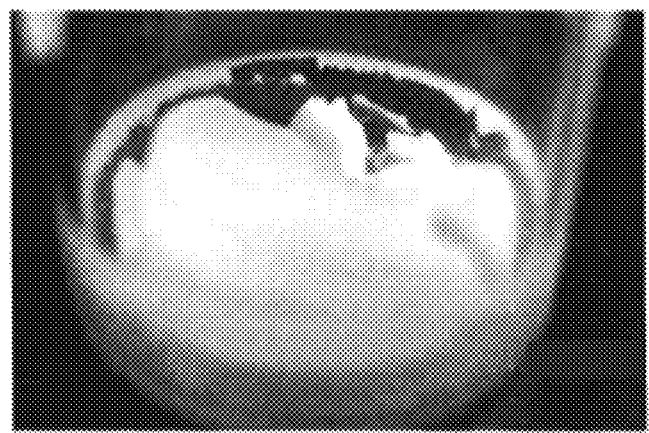
FIG. 35 provides a top view of a lyophilized product for a repeated study of a high shelf temperature, high chamber pressure lyophilization process as described herein.

FIG. 34 provides a side view of the lyophilized product. FIG. 35 provides a close-up top view of the product depicted in FIG. 34. The cakes appeared dense with a uniform white color. The original fill height was 4-5 mm while the product height was 4 mm with 1 mm uniform shrinkage observed around the sides of the cakes. The top, bottom, and sides of the cakes appeared sheen with some matte on the bottom.

The tops of the cakes were textured and concave with cracks through the entire cake height. Upon inversion and jarring, the cake pieces moved to the top of the vial broke up more. Residual material as a thin white film was observed around the sides and bottom of the vial where the cake was originally seated.

Reconstitution was performed by extruding 1 mL of the diluent into each vial using a vial adapter or syringe and allowing the vials to sit undisturbed until clear. All the samples resulted in clear and colorless solutions. Due to the long reconstitution times, reconstitution times are reported in minutes for this study. TABLE 55 provides the average reconstitution time for this study. Reconstitution took about 12.5 minutes for the solution to fully clear. Turbidity testing on all samples showed NTU values less than or equal to 5 NTU, which was in the same range as previous results for this lot of the compound of Formula (1).

TABLE 55

| Average Rerun Time (min) | Turbidity (NTU) |
|---|---|
| 12.5 | 4.88, 0.839 0.782 |

The TGA analysis results are provided in TABLE 56 below.

TABLE 56

| Vial | Weight Loss (% w/w) | Temperature Range (° C.) |
|---|---|---|
| 1 | 2.09 | 30 to 89 |
|  | 4.84 | 89 to 136 |
|  | 9.59 | 136 to 199 |
|  | Total: 16.52 |  |

Figure 36:
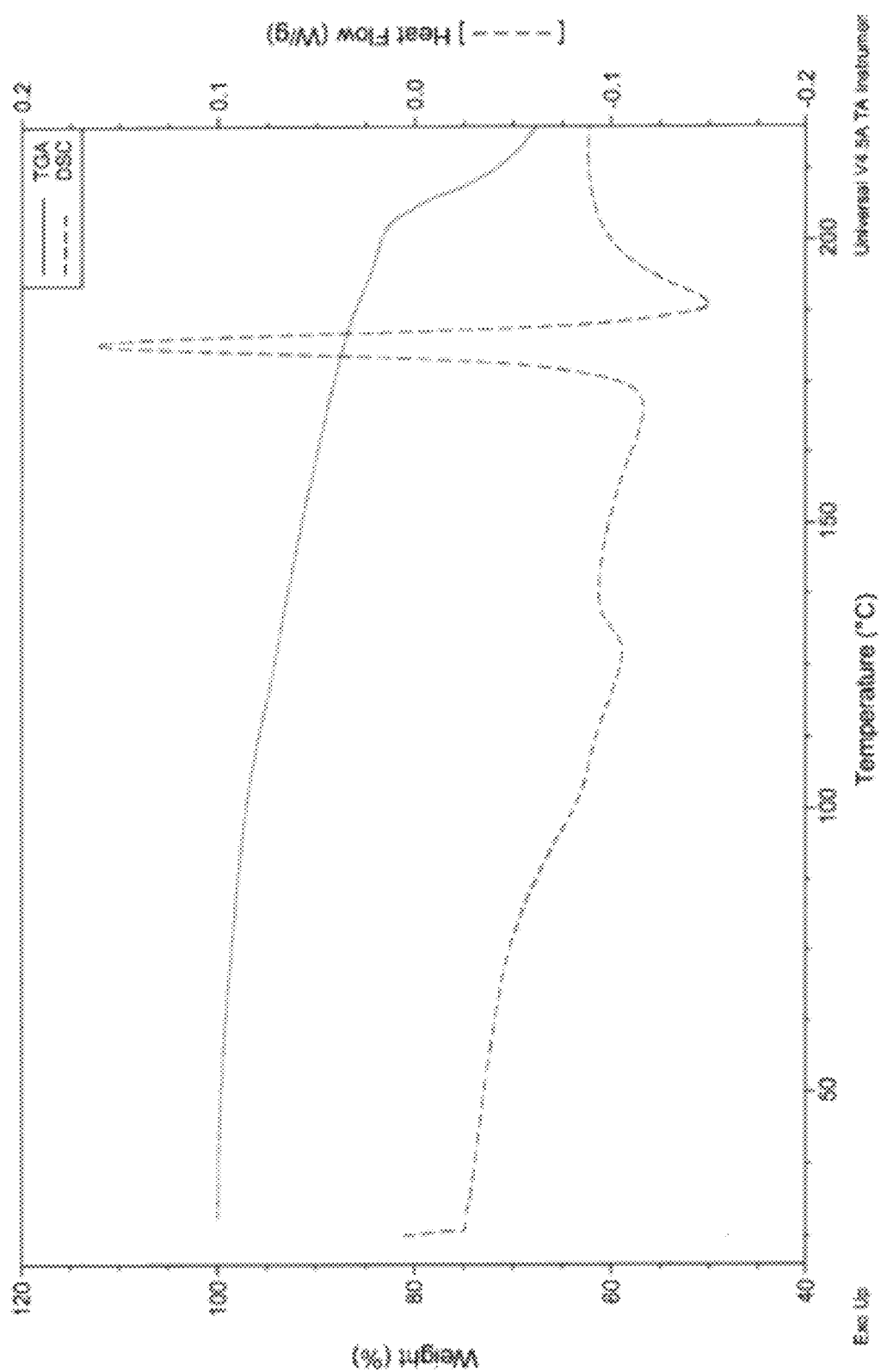
FIG. 36 provides an overlay of differential scanning calorimetry and thermogravimetric analysis thermograms for a repeated study of a high shelf temperature, high chamber pressure lyophilization process as described herein.

The DSC results are provided in FIG. 36 below. FIG. 36 provides an overlay between the DSC and TGA thermograms. TGA results showed about 17% w/w mass loss, which was slightly lower than the results from Target study, but consistent with the previous HH study. The DSC showed a shift in baseline that correlated to the various weight loss events by TGA, which was consistent with the target study results.

Product temperatures remained below the critical temperature of −4° C. prior to reaching a break for all the center thermocouples. The edge thermocouples had break temperatures as warm as −3° C.; however, no effect on the finished product was detected. The thermocouple product temperatures in the center vials were all slightly above the range of −8° C. to −6° C. Product temperatures reached a steady state after approximately 42 hours in primary drying.

This study demonstrated that the high shelf temperature and high chamber pressure boundary conditions achieved finished product similar to the target study.

TABLE 57 below provides a summary of the product temperatures and TGA mass loss studies for all of the foregoing studies:

TABLE 57

| Study | Average Center Product Temperature (° C.) "Break" | Average Center Product Temperature (° C.) Secondary Drying | TGA Mass Loss (% w/w) |
|---|---|---|---|
| A: Target | −9 | 33.1 | (18.9, 18.6) |
| B: HH | −6.5 | 36.5 | (18.1, 17.4) |
| C: LH | −11.3 | 30.4 | (18.4, 19.1) |
| D: HL | −6.5 | 35.1 | (17.1, 17.5) |
| E: LL | −13.1 | 28 | (22.2, 17.8) (19.8, 19.2) |
| F: Target | −8 | 37 | (18.9, 19.8) |
| G: LH | −10.4 | 34.8 | 16.7 |
| H: HH | −7.1 | 39.9 | 16.7 |

TABLE 58 below provides a summary of sublimation for all of the foregoing studies:

TABLE 58

| Study | Time to Complete Sublimation (Hours) Thermocouples | Time to Complete Sublimation (Hours) RGA |
|---|---|---|
| A: Target | 64 | — |
| B: HH | 54 | 54 |

TABLE 58-continued

| Study | Time to Complete Sublimation (Hours) Thermocouples | Time to Complete Sublimation (Hours) RGA |
|---|---|---|
| C: LH | 76 | 64 |
| D: HL | 51 | 49 |
| E: LL | 80.5 | — |
| F: Target | 40 | — |
| G: LH | 75 | — |
| H: HH | 42 | 61 |

Example 9: Guadecitabline Lyophilization Cycle Parameters

The process provided in TABLE 59 below was used to lyophilize up to 30,000 vials of compound of formula (1). All the analytical test results including, but not limited to, assay, related substances, residual DMSO content, and reconstitution time, met the acceptance criteria.

TABLE 59

| Step | | Time (min) | Shelf Temperature Set point (° C.) | Chamber Pressure Set Point (μbar) |
|---|---|---|---|---|
| Loading | | NA | 20 | Atmospheric Pressure |
| Freezing | Freezing | 60 | 20 | Atmospheric Pressure |
|  | Freezing Ramp | 130 | −45 | Atmospheric Pressure |
|  | Hold | 60 | −45 | Atmospheric Pressure |
|  | Annealing Ramp | 90 | 0 | Atmospheric Pressure |
|  | Hold | 120 | 0 | Atmospheric Pressure |
|  | Freezing Ramp | 90 | −45 | Atmospheric Pressure |
|  | Freezing | 120 | −45 | Atmospheric Pressure |
| Evacuation | | NA | −45 | 27 |
| Primary drying | Soak | 240 | −45 | 27 |
|  | Ramp | 78 | −6 | 27 |
|  | Hold | 4830 | −6 | 27 |
| Secondary drying | Ramp (Stage 1) | 230 | 40 | 267 |
|  | Hold (Stage 1) | 600 | 40 | 267 |
|  | Ramp (Stage 2) | 40 | 20 | 267 |
| Pre-aeration (with nitrogen) | N/A | 20 | | 900 mbar |
| Stoppering | N/A | 20 | | 900 mbar |
| Total time | | 6688 min (4.64 day) | | |

Results from example batches at two different scales were compared and the comparisons are provided in TABLE 60 below.

TABLE 60

| Test | Batch #1 | Batch #2 |
|---|---|---|
| Assay | 97% | 98.2% |
| Impurities | Specified and unspecified impurities met acceptance criteria | Specified and unspecified impurities met acceptance criteria |
| Reconstitution time | 180 sec | 123 seconds |
| Residual solvents (DMSO) | 24 mg/vial | 28 mg/vial |

Example 10: Impurities in the Lyophilized Pharmaceutical Product

Batches of the lyophilized product were analyzed to determine the purity of the product, types and amounts of impurities, water content (mg/vial), and DMSO content (mg/vial). The impurities detected in the batches of the lyophilized product included the following compounds:

Impurity 1

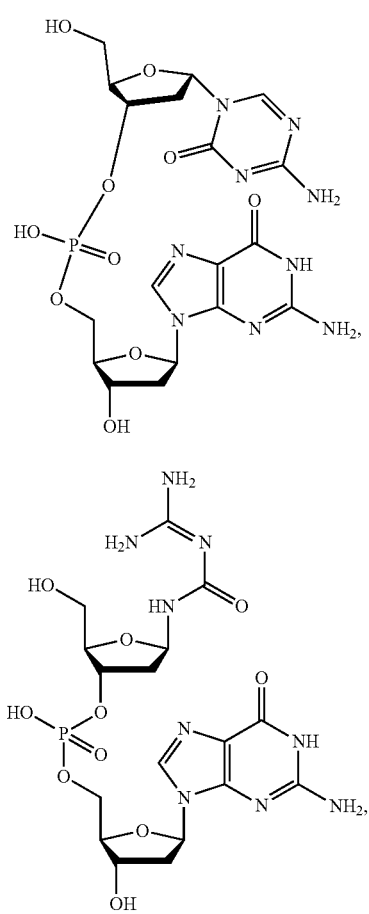

Impurity 2

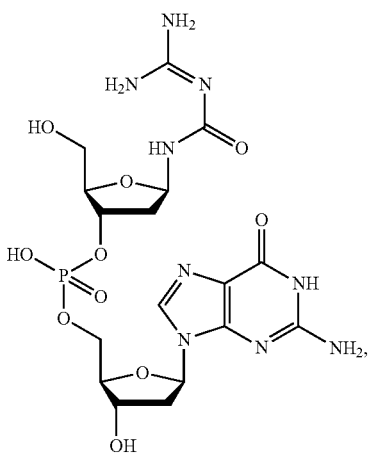

Impurity 3

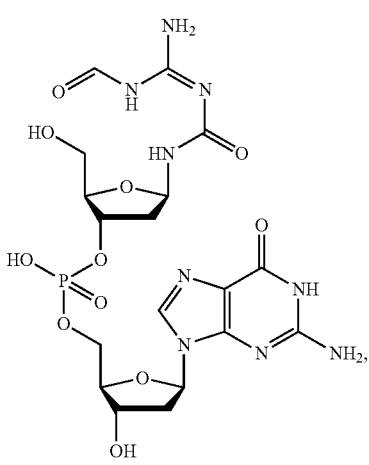

Impurity 4

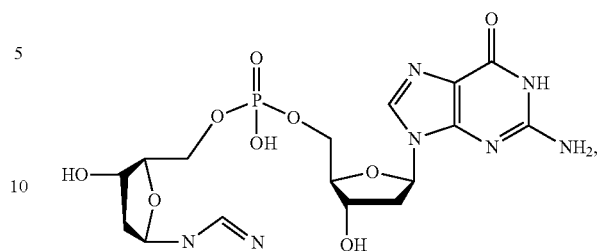

Impurity 5

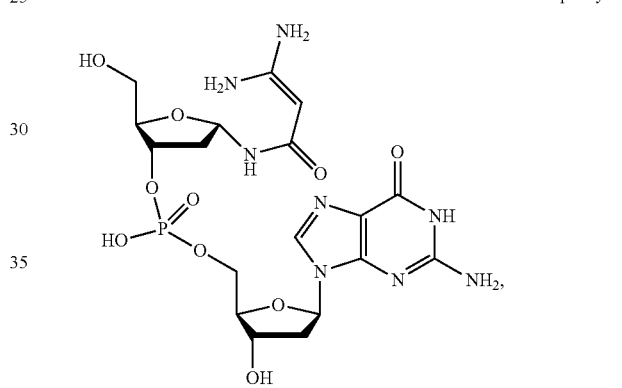

Impurity 6

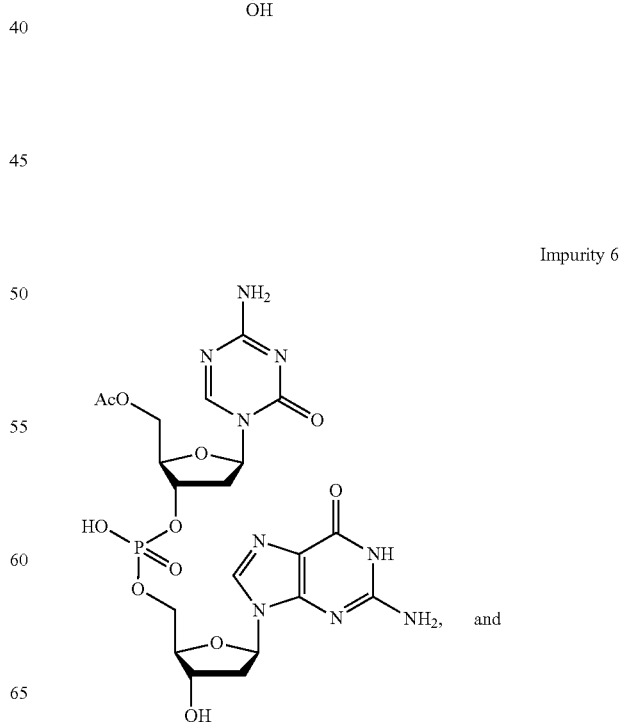

and

Impurity 7

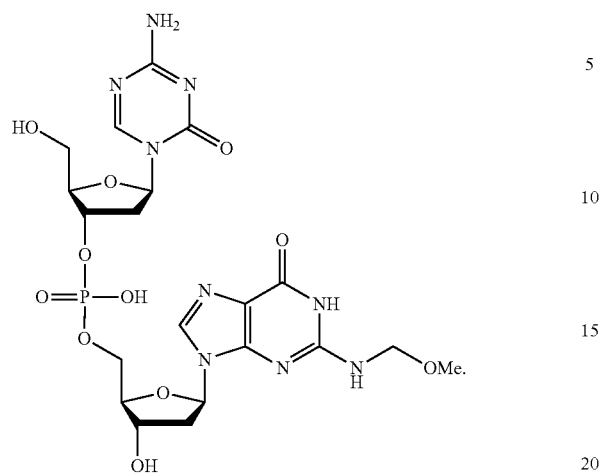

TABLE 60 and TABLE 61 show the contents of 7 batches of the lyophilized pharmaceutical product disclosed herein.

TABLE 60

|  | Batch 1 | | | Batch 2 | | |
| --- | --- | --- | --- | --- | --- | --- |
|  | Vial 1 | Vial 2 | Mean | Vial 1 | Vial 2 | Mean |
| Assay (%) | 97.5 | 97.0 | 97.2 | 96.1 | 96.5 | 96.3 |
| Related substances (%): | | | | | | |
| Impurity 1 | <0.05% | <0.05% | <0.05% | <0.05% | <0.05% | <0.05% |
| Impurity 2 | 0.11 | 0.11 | 0.11 | 0.11 | 0.11 | 0.11 |
| Impurity 3 | <0.05% | <0.05% | <0.05% | <0.05% | <0.05% | <0.05% |
| Impurity 4 | <0.05% | <0.05% | <0.05% | <0.05% | <0.05% | <0.05% |
| Impurity 5 | 0.08 | 0.09 | 0.08 | 0.09 | 0.09 | 0.09 |
| Impurity 6 | 0.12 | 0.12 | 0.12 | 0.12 | 0.12 | 0.12 |
| Impurity 7 | <0.05% | <0.05% | <0.05% | <0.05% | <0.05% | <0.05% |
| Sum of impurities | 0.32 | 0.32 | 0.32 | 0.32 | 0.32 | 0.32 |
| Water content (mg/vial) | 0.3 | 0.3 | 0.3 | 0.3 | 0.3 | 0.3 |
| DMSO by HPLC (mg/vial) | 28.4 | 28.5 | 28.5 | 27.0 | 27.7 | 27.4 |
|  | Batch 3 | | | Batch 4 | | |
|  | Vial 1 | Vial 2 | Mean | Vial 1 | Vial 2 | Mean |
| Assay (%) | 94.2 | 92.8 | 93.5 | 95.8 | 95.7 | 95.7 |
| Related substances (%): | | | | | | |
| Impurity 1 | <0.05% | <0.05% | <0.05% | <0.05% | <0.05% | <0.05% |
| Impurity 2 | 0.10 | 0.10 | 0.10 | 0.09 | 0.09 | 0.09 |
| Impurity 3 | <0.05% | <0.05% | <0.05% | <0.05% | <0.05% | <0.05% |
| Impurity 4 | <0.05% | <0.05% | <0.05% | <0.05% | <0.05% | <0.05% |
| Impurity 5 | 0.09 | 0.09 | 0.09 | 0.10 | 0.10 | 0.10 |
| Impurity 6 | 0.13 | 0.12 | 0.13 | 0.13 | 0.12 | 0.12 |
| Impurity 7 | <0.05% | <0.05% | <0.05% | <0.05% | <0.05% | <0.05% |
| Sum of impurities | 0.32 | 0.31 | 0.32 | 0.32 | 0.31 | 0.31 |
| Water content (mg/vial) | 0.3 | 0.3 | 0.3 | 0.3 | 1.3 | 0.8 |
| DMSO by HPLC (mg/vial) | 27.2 | 26.2 | 26.7 | 28.7 | 26.2 | 27.5 |

TABLE 61

| | Batch 5 | | | Batch 6 | | | Batch 7 | | |
|---|---|---|---|---|---|---|---|---|---|
| | Vial 1 | Vial 2 | Mean | Vial 1 | Vial 2 | Mean | Vial 1 | Vial 2 | Mean |
| Assay (%) | 96.2 | 97.0 | 96.6 | 90.9 | 95.1 | 93.0 | 80.2 | 94.1 | 87.1 |
| Related substances (%): | | | | | | | | | |
| Impurity 1 | <0.05% | <0.05% | <0.05% | 0.05 | 0.05 | 0.05 | <0.05% | <0.05% | <0.05% |
| Impurity 2 | 0.08 | 0.07 | 0.07 | 0.27 | 0.27 | 0.27 | 0.08 | 0.09 | 0.09 |
| Impurity 3 | <0.05% | <0.05% | <0.05% | 0.08 | 0.08 | 0.08 | <0.05% | <0.05% | <0.05% |
| Impurity 4 | <0.05% | <0.05% | <0.05% | 0.06 | 0.06 | 0.06 | <0.05% | <0.05% | <0.05% |
| Impurity 5 | 0.10 | 0.10 | 0.10 | 0.27 | 0.27 | 0.27 | 0.10 | 0.09 | 0.09 |
| Impurity 6 | <0.05% | <0.05% | <0.05% | <0.05% | <0.05% | <0.05% | <0.05% | <0.05% | <0.05% |
| Impurity 7 | <0.05% | <0.05% | <0.05% | 0.06 | 0.06 | 0.06 | <0.05% | <0.05% | <0.05% |
| Sum of impurities | 0.18 | 0.17 | 0.17 | 0.80 | 0.79 | 0.79 | 0.18 | 0.18 | 0.18 |
| Water content (mg/vial) | 0.8 | 0.4 | 0.6 | 0.3 | 0.3 | 0.3 | 0.3 | 0.3 | 0.3 |
| DMSO by HPLC (mg/vial) | 30.7 | 27.4 | 29.1 | 30.5 | 31.3 | 30.9 | 30.9 | 31.1 | 31.0 |

EMBODIMENTS

The following non-limiting embodiments provide illustrative examples of the invention, but do not limit the scope of the invention.

Embodiment 1

A method of preparing a lyophilized pharmaceutical composition, the method comprising dissolving a compound of formula (1):

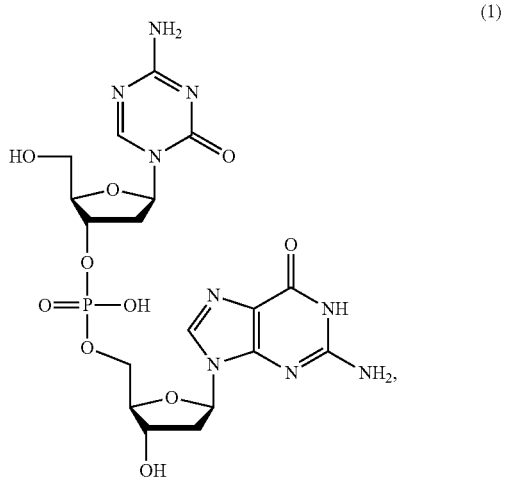

(1)

or a pharmaceutically-acceptable salt thereof, in a solvent comprising dimethylsulfoxide (DMSO) to form a solution, wherein the solvent is then removed by a freeze-drying process to give a lyophilized product, wherein the freeze-drying process comprises: (i) a first freezing stage in which the solution is frozen by reducing the temperature of the solution to about −45° C.; (ii) a first annealing stage in which the temperature of the frozen solution is raised to about 0° C., wherein the temperature of about 0° C. keeps the solution frozen; (iii) a second freezing stage in which the temperature of the solution is lowered to a temperature of about −45° C.; (iv) a primary drying stage in which the temperature of the solution is raised to about −6° C., wherein the primary drying stage comprises a sublimation step in which the DMSO is removed by sublimation from the solution in its frozen state under reduced pressure to give a partially dried product; and (v) a secondary drying stage in which the temperature of the solution is raised to about 40° C., wherein in the secondary drying stage the DMSO is removed by evaporation from the partially dried product in a non-frozen state under reduced pressure to give the lyophilized product.

Embodiment 2

The method of embodiment 1, wherein the compound of formula (1) is in the form of a sodium salt.

Embodiment 3

The method of any one of embodiments 1-2, wherein the solvent is non-aqueous.

Embodiment 4

The method of any one of embodiments 1-3, wherein the lyophilized pharmaceutical composition has a dissolution time, at ambient temperature, and without the aid of mechanised stirring, in a non-aqueous solvent containing 65% (v/v) propylene glycol; 25% (v/v) glycerine; and 10% (v/v) ethanol, of no greater than about 20 minutes.

Embodiment 5

The method of any one of embodiments 1-4, wherein an amount of the lyophilized pharmaceutical composition obtained from 1 gram of the solution has a residual DMSO content of no greater than about 20 mg.

Embodiment 6

The method of any one of embodiments 1-5, wherein any residual DMSO present in the lyophilized pharmaceutical composition is in an amount corresponding to no more than 35 mg per 100 mg equivalent of a free base of the compound of formula (1).

Embodiment 7

The method of any one of embodiments 1-6, further comprising packing the lyophilized pharmaceutical in a sealed pharmaceutical container.

Embodiment 8

The method of any one of embodiments 1-7, further comprising dissolving the lyophilized pharmaceutical composition in a solvent to form an injectable liquid composition.

Embodiment 9

The method of embodiment 8, wherein the solvent is a non-aqueous solvent.

Embodiment 10

The method of any one of embodiments 1-9, wherein the solution further comprises a co-solvent.

Embodiment 11

The method of any one of embodiments 1-10, further comprising reconstituting the lyophilized pharmaceutical composition in a pharmaceutically acceptable solvent to give a liquid formulation containing a compound of formula (1) or the pharmaceutically acceptable salt thereof.

Embodiment 12

The method of any one of embodiments 1-11, wherein the reduced pressure in the primary drying stage is from about 5 µBar to about 40 µBar.

Embodiment 13

The method of any one of embodiments 1-12, wherein a pressure in the secondary drying stage is from about 5 µBar to about 40 µBar.

Embodiment 14

The method of any one of embodiments 1-13, wherein a pressure in the first freezing stage is from about 750 µBar to about 850 µBar.

Embodiment 15

The method of any one of embodiments 1-14, wherein a pressure in the annealing stage is from about 750 µBar to about 850 µBar.

Embodiment 16

A pharmaceutical composition prepared by a process comprising the steps of: dissolving a compound of formula (1):

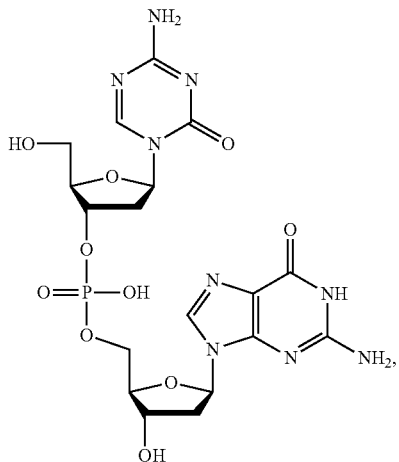

or a pharmaceutically-acceptable salt thereof, in a solvent comprising dimethylsulfoxide (DMSO) to form a solution, wherein the solvent is then removed by a freeze-drying process to give a lyophilized product, wherein the freeze-drying process comprises: (i) a first freezing stage in which the solution is frozen by reducing the temperature of the solution to about −45° C.; (ii) a first annealing stage in which the temperature of the frozen solution is raised to about 0° C., wherein the temperature of about 0° C. keeps the solution frozen; (iii) a second freezing stage in which the temperature of the solution is lowered to a temperature of about −45° C.; (iv) a primary drying stage in which the temperature of the solution is raised to about −6° C., wherein the primary drying stage comprises a sublimation step in which the DMSO is removed by sublimation from the solution in its frozen state under reduced pressure to give a partially dried product; and (v) a secondary drying stage in which the temperature of the solution is raised to about 40° C., wherein in the secondary drying stage the DMSO is removed by evaporation from the partially dried product in a non-frozen state under reduced pressure to give the lyophilized product.

Embodiment 17

The pharmaceutical composition of embodiment 16, wherein the compound of formula (1) is in the form of a sodium salt.

Embodiment 18

The pharmaceutical composition of any one of embodiments 16-17, wherein the solvent is non-aqueous.

Embodiment 19

The pharmaceutical composition of any one of embodiments 16-18, wherein the lyophilized pharmaceutical composition has a dissolution time, at ambient temperature, and without the aid of mechanised stirring, in a non-aqueous solvent containing 65% (v/v) propylene glycol; 25% (v/v) glycerine; and 10% (v/v) ethanol, of no greater than about 20 minutes.

Embodiment 20

The pharmaceutical composition of any one of embodiments 16-19, wherein an amount of the lyophilized pharmaceutical composition obtained from 1 gram of the solution has a residual DMSO content of no greater than about 20 mg.

Embodiment 21

The pharmaceutical composition of any one of embodiments 16-20, wherein any residual DMSO present in the lyophilized pharmaceutical composition is in an amount corresponding to no more than 35 mg per 100 mg equivalent of a free base of the compound of formula (1).

Embodiment 22

The pharmaceutical composition of any one of embodiments 16-21, the process further comprising packing the lyophilized pharmaceutical in a sealed pharmaceutical container.

Embodiment 23

The pharmaceutical composition of any one of embodiments 16-22, the process further comprising dissolving the lyophilized pharmaceutical composition in a solvent to form an injectable liquid composition.

Embodiment 24

The pharmaceutical composition of embodiment 23, wherein the solvent is a non-aqueous solvent.

Embodiment 25

The pharmaceutical composition of any one of embodiments 16-24, wherein the solution further comprises a co-solvent.

Embodiment 26

The pharmaceutical composition of any one of embodiments 16-25, the process further comprising reconstituting the lyophilized pharmaceutical composition in a pharmaceutically acceptable solvent to give a liquid formulation containing a compound of formula (1) or the pharmaceutically acceptable salt thereof.

Embodiment 27

The pharmaceutical composition of any one of embodiments 16-26, wherein the reduced pressure in the primary drying stage is from about 5 μBar to about 40 μBar.

Embodiment 28

The method of any one of embodiments 16-27, wherein a pressure in the secondary drying stage is from about 5 μBar to about 40 μBar.

Embodiment 29

The method of any one of embodiments 16-28, wherein a pressure in the first freezing stage is from about 750 μBar to about 850 μBar.

Embodiment 30

The method of any one of embodiments 16-29, wherein a pressure in the annealing stage is from about 750 μBar to about 850 μBar.

Embodiment 31

A composition comprising:
a) a compound of the formula:

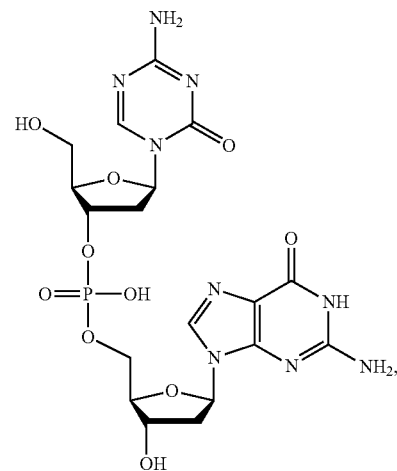

Formula (1)

or a pharmaceutically acceptable salt thereof,
wherein the composition comprises at least 95% of the compound of Formula (1); and
b) a nucleotide-based compound that is not a compound of Formula (1).

Embodiment 32

The composition of embodiment 31, wherein the nucleotide-based compound is a compound of formula (2):

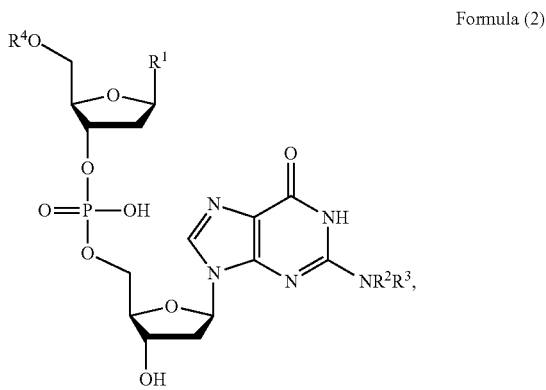

Formula (2)

or a pharmaceutically acceptable salt thereof,
wherein:
$R^1$ is a heteroaryl or a carbamide, each of which is independently substituted or unsubstituted;
each $R^2$ and $R^3$ is independently alkyl, which is substituted or unsubstituted; or hydrogen; and R⁴ is hydrogen or an acyl group, each of which is independently substituted or unsubstituted.

Embodiment 33

The composition of embodiment 32, wherein $R^1$ is a carbamide that is substituted.

Embodiment 34

The composition of embodiment 32, wherein $R^1$ is heteroaryl.

Embodiment 35

The composition of embodiment 32 or 34, wherein $R^1$ is 4-amino-2H-1$\lambda^2$,3,5-triazin-2-one.

Embodiment 36

The composition of any one of embodiments 32-35, wherein each $R^2$ and $R^3$ is substituted alkyl or hydrogen.

Embodiment 37

The composition of any one of embodiments 32-36, wherein $R^2$ is H and $R^3$ is methyl substituted with methoxy.

Embodiment 38

The composition of any one of embodiments 32-37, wherein $R^4$ is hydrogen.

Embodiment 39

The composition of any one of embodiments 32-37, wherein $R^4$ is an acyl group.

Embodiment 40

The composition of embodiment 32, wherein the compound of formula (2) is

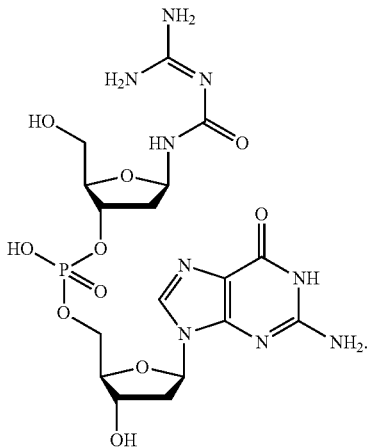

Embodiment 41

The composition of embodiment 32, wherein the compound of formula (2) is

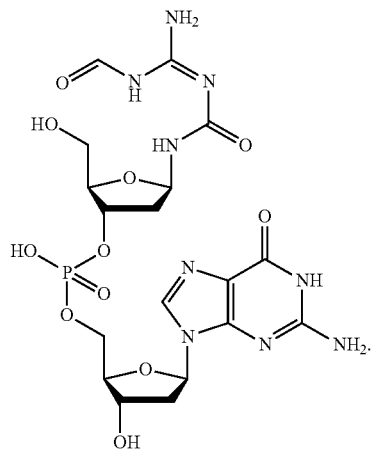

Embodiment 42

The composition of embodiment 32, wherein the compound of formula (2) is

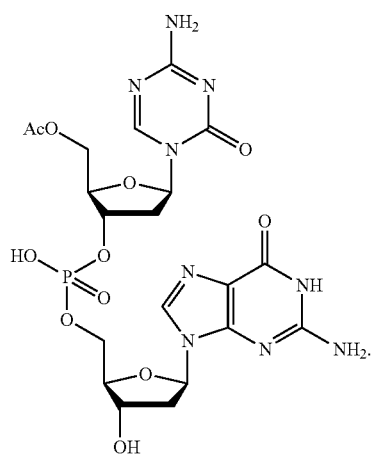

Embodiment 43

The composition of embodiment 32, wherein the compound of formula (2) is

87

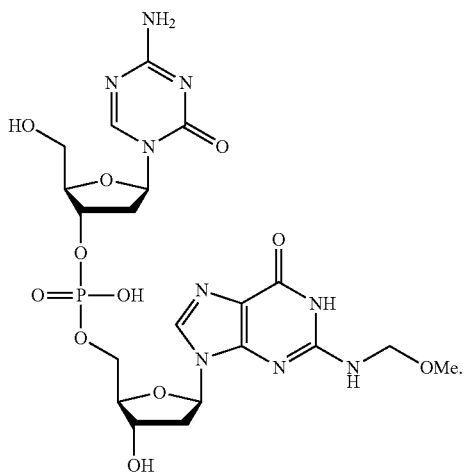

Embodiment 44

The composition of embodiment 31, wherein the nucleotide-based compound is a compound of formula (3):

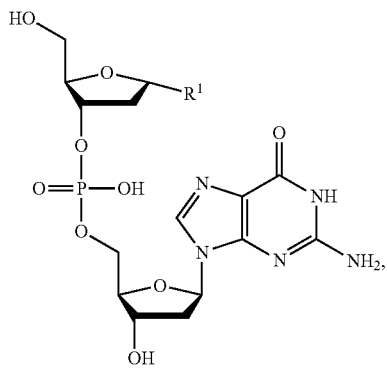

Formula (3)

or a pharmaceutically acceptable salt thereof, wherein $R^1$ is heteroaryl or a carbamide, each of which is independently substituted or unsubstituted.

Embodiment 45

The composition of embodiment 44, wherein $R^1$ is heteroaryl.

Embodiment 46

The composition of embodiment 44 or 45, wherein $R^1$ is 4-amino-2H-1$\lambda^2$,3,5-triazin-2-one.

Embodiment 47

The composition of embodiment 44, wherein $R^1$ is a carbamide that is substituted.

Embodiment 48

The composition of embodiment 44, wherein the compound of formula (3) is

88

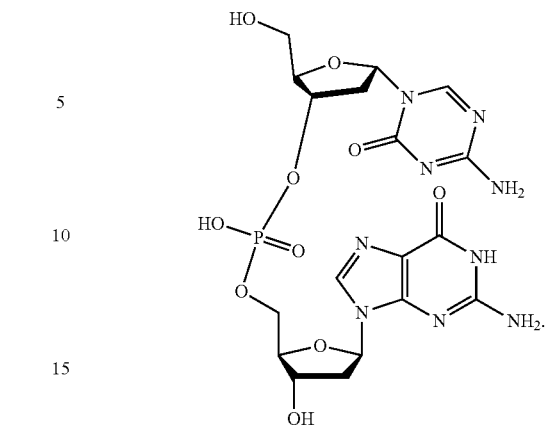

Embodiment 49

The composition of embodiment 44, wherein the compound of formula (3) is

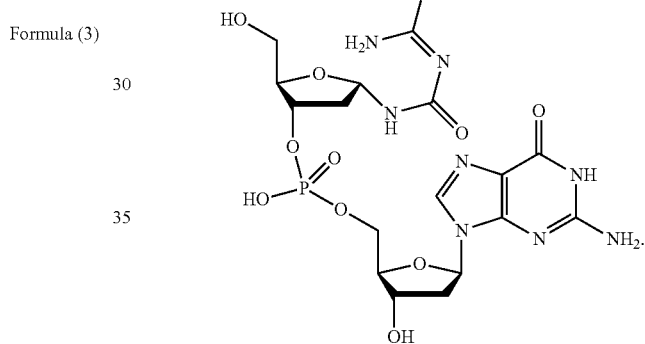

Embodiment 50

The composition of embodiment 31, wherein the nucleotide-based compound is a compound of formula (4):

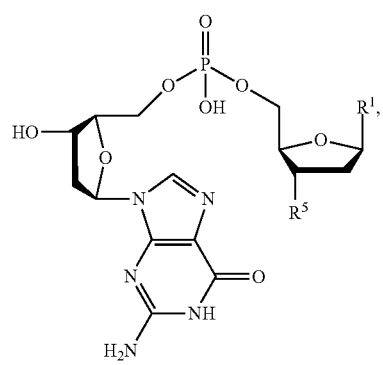

Formula (4)

or a pharmaceutically acceptable salt thereof, wherein $R^1$ is heteroaryl, which is substituted or unsubstituted; and $R^5$ is hydroxy or a nucleotide.

Embodiment 51

The composition of embodiment 50, wherein $R^1$ is heteroaryl that is substituted.

Embodiment 52

The composition of embodiments 50 or 51, wherein $R^1$ is 4-amino-2H-1$\lambda^2$,3,5-triazin-2-one.

Embodiment 53

The composition of embodiments 50 or 51, wherein $R^1$ is 2-amino-9$\lambda^2$-purin-6(1H)-one.

Embodiment 54

The composition of any one of embodiments 50-53, wherein $R^5$ is a hydroxyl group.

Embodiment 55

The composition of any one of embodiments 50-53, wherein $R^5$ is a nucleotide.

Embodiment 56

The composition of any one of embodiments 50-53 and 55, wherein the nucleotide has the formula:

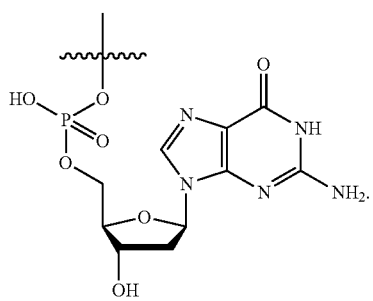

Embodiment 57

The composition of embodiment 50, wherein the compound of formula (4) is

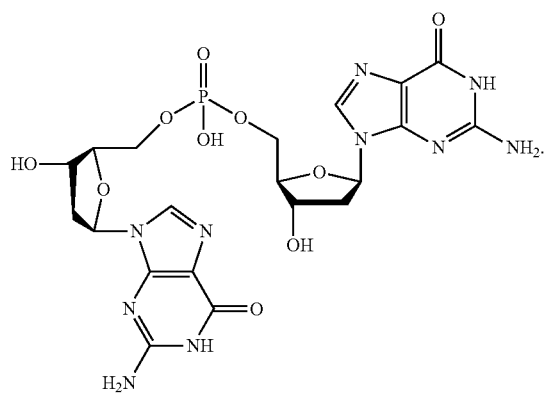

Embodiment 58

The composition of embodiment 50, wherein the compound of formula (4) is

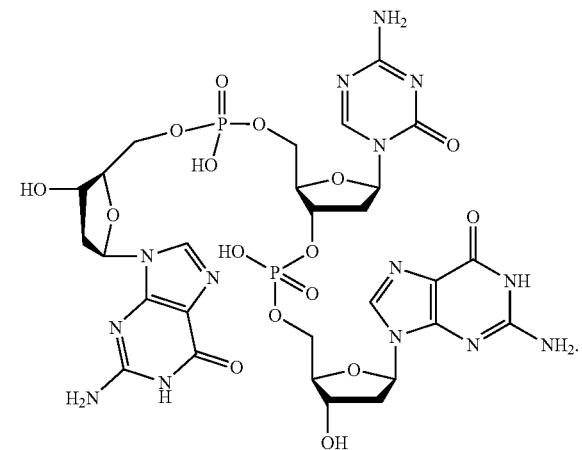

Embodiment 58a

A pharmaceutical composition comprising, in unit dosage form:

a) a compound of formula (1):

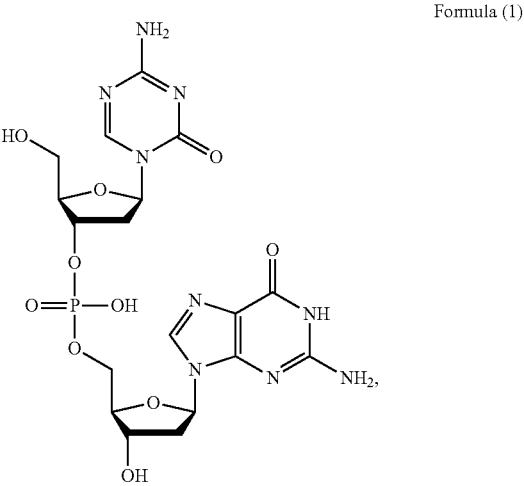

Formula (1)

or a pharmaceutically acceptable salt thereof;

b) a nucleotide-based compound that is not a compound of Formula (1); and c) a pharmaceutically acceptable excipient.

Embodiment 59

The pharmaceutical composition of Embodiment 58a, wherein the nucleotide-based compound is a compound of formula (2):

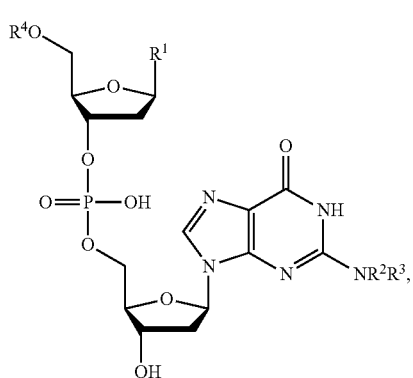

Formula (2)

or a pharmaceutically acceptable salt thereof, wherein: $R^1$ is a heteroaryl or a carbamide, each of which is independently substituted or unsubstituted; each $R^2$ and $R^3$ is independently alkyl, which is substituted or unsubstituted; or hydrogen; and $R^4$ is hydrogen or an acyl group, each of which is independently substituted or unsubstituted.

Embodiment 60

The pharmaceutical composition of embodiment 59, wherein $R^1$ is a carbamide that is substituted.

Embodiment 61

The pharmaceutical composition of embodiment 59, wherein $R^1$ is heteroaryl.

Embodiment 62

The pharmaceutical composition of embodiment 59 or 61, wherein $R^1$ is 4-amino-2H-1$\lambda^2$,3,5-triazin-2-one.

Embodiment 63

The pharmaceutical composition of any one of embodiments 59-62, wherein each $R^2$ and $R^3$ is substituted alkyl or hydrogen.

Embodiment 64

The pharmaceutical composition of any one of embodiments 59-63, wherein $R^2$ is H and $R^3$ is methyl substituted with methoxy.

Embodiment 65

The pharmaceutical composition of any one of embodiments 59-64, wherein $R^4$ is hydrogen.

Embodiment 66

The pharmaceutical composition of any one of embodiments 59-64, wherein $R^4$ is an acyl group.

Embodiment 67

The pharmaceutical composition of embodiment 59, wherein the compound of formula (2) is

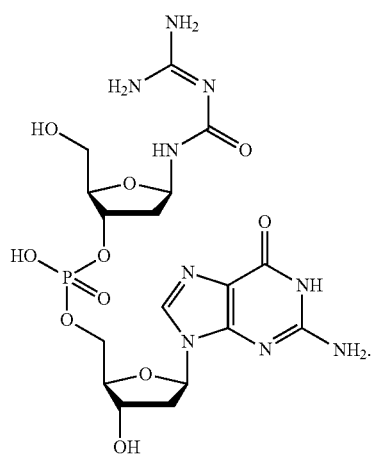

Embodiment 68

The pharmaceutical composition of embodiment 59, wherein the compound of formula (2) is

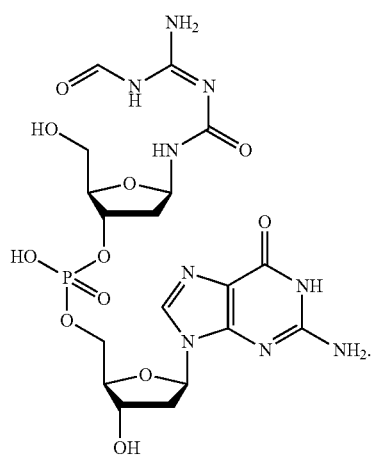

Embodiment 69

The pharmaceutical composition of embodiment 59, wherein the compound of formula (2) is

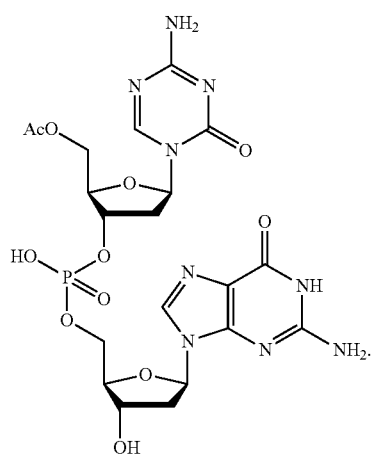

Embodiment 70

The pharmaceutical composition of embodiment 59, wherein the compound of formula (2) is

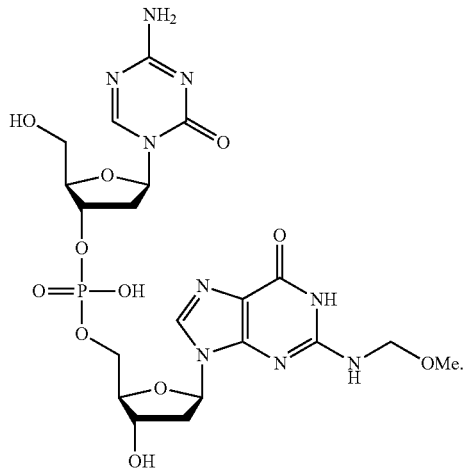

Embodiment 71

The pharmaceutical composition of Embodiment 58a, wherein the nucleotide-based compound is a compound of formula (3):

Formula (3)

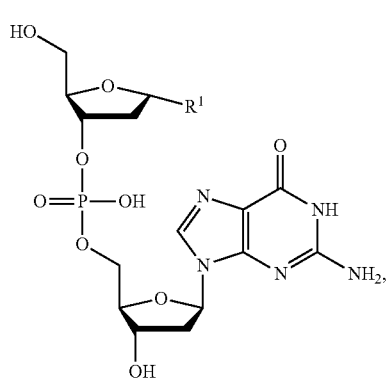

or a pharmaceutically acceptable salt thereof, wherein $R^1$ is heteroaryl or a carbamide, each of which is independently substituted or unsubstituted.

Embodiment 72

The pharmaceutical composition of embodiment 71, wherein $R^1$ is heteroaryl.

Embodiment 73

The pharmaceutical composition of embodiment 71 or 72, wherein $R^1$ is 4-amino-2H-1$\lambda^2$,3,5-triazin-2-one.

Embodiment 74

The pharmaceutical composition of embodiment 71, wherein $R^1$ is a carbamide that is substituted.

Embodiment 75

The pharmaceutical composition of embodiment 71, wherein the compound of formula (3) is

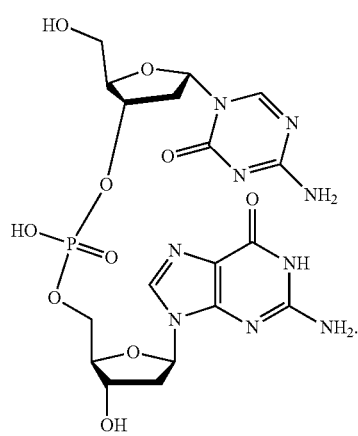

Embodiment 76

The pharmaceutical composition of embodiment 71, wherein the compound of formula (3) is

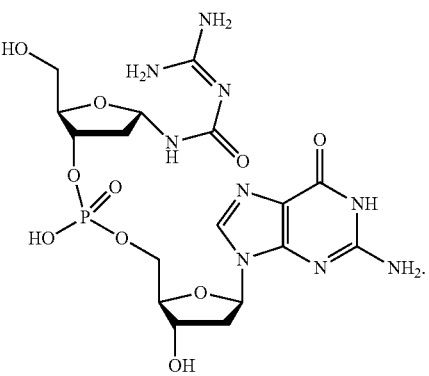

Embodiment 77

The pharmaceutical composition of Embodiment 58a, wherein the nucleotide-based compound is a compound of formula (4):

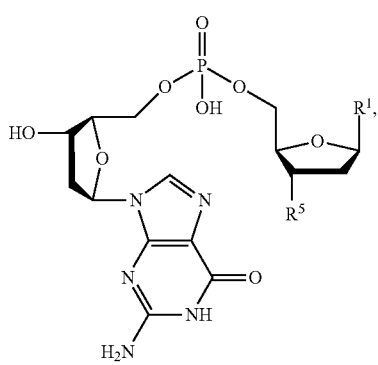

Formula (4)

or a pharmaceutically acceptable salt thereof, wherein $R^1$ is heteroaryl, which is substituted or unsubstituted; and $R^5$ is hydroxy or a nucleotide.

Embodiment 78

The pharmaceutical composition of embodiment 77, wherein $R^1$ is heteroaryl that is substituted.

Embodiment 79

The pharmaceutical composition of embodiment 77 or 78, wherein $R^1$ is 4-amino-2H-1$\lambda^2$,3,5-triazin-2-one.

Embodiment 80

The pharmaceutical composition of embodiment 77 or 78, wherein $R^1$ is 2-amino-9$\lambda^2$-purin-6(1H)-one.

Embodiment 81

The pharmaceutical composition of any one of embodiments 77-80, wherein $R^5$ is a hydroxyl group.

Embodiment 82

The pharmaceutical composition of any one of embodiments 77-80, wherein $R^5$ is a nucleotide.

Embodiment 83

The pharmaceutical composition of any one of embodiments 77-80 or 82, wherein the nucleotide has the formula:

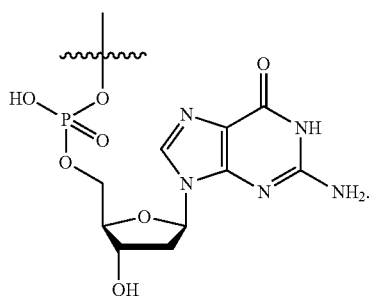

Embodiment 84

The pharmaceutical composition of embodiment 77, wherein the compound of formula (4) is

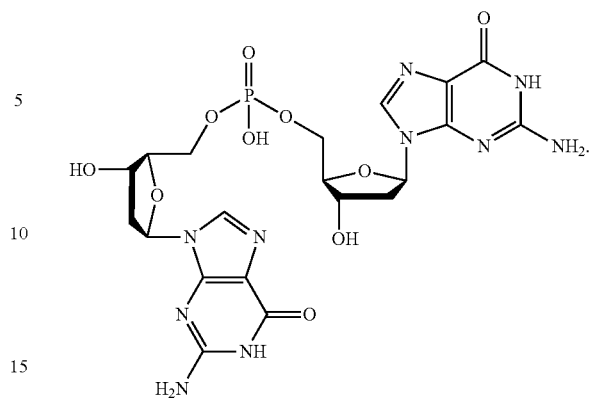

Embodiment 85

The pharmaceutical composition of embodiment 77, wherein the compound of formula (4) is Embodiment 85a The pharmaceutical composition of any one of embodiments 58a-85, wherein the compound of Formula (1) and the nucleotide-based compound are present in a ratio of about 20,000:about 1, about 19,000:about 1, about 18,000:about 1, about 17,000:about 1, about 16,000:about 1, about 15,000:about 1, about 14,000:about 1, about 13,000:about 1, about 12,000:about 1, about 11,000:about 1, about 10,000:about 1, about 9,900:about 1, about 9,800:about 1, about 9,700:about 1, about 9,600:about 1, about 9,500:about 1, about 9,400:about 1, about 9,300:about 1, about 9,200:about 1, about 9,100:about 1, about 9,000:about 1, about 8,900:about 1, about 8,800:about 1, about 8,700:about 1, about 8,600:about 1, about 8,500:about 1, about 8,400:about 1, about 8,300:about 1, about 8,200:about 1, about 8,100:about 1, about 8,000:about 1, about 7,900:about 1, about 7,800:about 1, about 7,700:about 1, about 7,600:about 1, about 7,500:about 1, about 7,400:about 1, about 7,300:about 1, about 7,200:about 1, about 7,100:about 1, about 7,000:about 1, about 6,900:about 1, about 6,800:about 1, about 6,700:about 1, about 6,600:about 1, about 6,500:about 1, about 6,400:about 1, about 6,300:about 1, about 6,200:about 1, about 6,100:about 1, about 6,000:about 1, about 5,900:about 1, about 5,800:about 1, about 5,700:about 1, about 5,600:about 1, about 5,500:about 1, about 5,400:about 1, about 5,300:about 1, about 5,200:about 1, about 5,100:about 1, about 5,000:about 1, about 4,900:about 1, about 4,800:about 1, about 4,700:about 1, about 4,600:about 1, about 4,500:about 1, about 4,400:about 1, about 4,300:about 1, about 4,200:about 1, about 4,100:about 1, about 4,000:about 1, about 3,900:about 1, about 3,800:about 1, about 3,700:about 1, about 3,600:about 1, about 3,500:about 1, about 3,400:about 1, about 3,300:about 1, about 3,200:about 1, about 3,100:about 1, about 3,000:about 1, about 2,900:about 1, about 2,800:about 1, about 2,700:about 1, about 2,600:about 1, about 2,500:about 1, about 2,400:about 1, about 2,300:about 1, about 2,200:about 1, about 2,100:about 1, about 2,000:about 1, about 1,900:about 1, about 1,800:about 1, about 1,700:about 1, about 1,600:about 1, about 1,500:about 1, about 1,400:about 1, about 1,300:about 1, about 1,200:about 1, about 1,100:about 1, about 1,000:about 1, about 990:about 1, about 980:about 1, about 970:about 1, about 960:about 1, about 950:about 1, about 800:about 1, about 700:about 1, about 600:1, about 500:about 1, about 400:about 1, about 300:about 1, about 200:about 1, about 100:about 1, about 95:about 1, about 90:about 1, about 85:about 1, about 80:about 1, about 75:about 1, about 70:about 1, about 65:about 1, about 60:about 1, about 55:about 1, about 50:about 1, about 45:about 1, about 40:about 1, about 35:about 1, about 30:about 1, about 25:about 1, about 20:about 1, about 19:about 1, about 18:about 1, about 17:about 1, about 16:about 1, about 15:about 1, about 14:about 1, about 13:about 1, about 12:about 1, about 11:about 1, or about 10:about 1.

Embodiment 85b

The pharmaceutical composition of any one of embodiments 58a-85, wherein the nucleotide-based compound is present in the pharmaceutical composition at an amount that is about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1%, about 4.2%, about 4.3%, about 4.4%, about 4.5%, about 4.6%, about 4.7%, about 4.8%, about 4.9%, about 5%, about 5.5%, about 6%, about 6.5%, about 7%, about 7.5%, about 8%, about 8.5%, about 9%, about 9.5%, about 10%, about 11%, about 12%, about 13%, about 14%, about 15%, about 16%, about 17%, about 18%, about 19%, about 20%, about 25%, about 30%, about 35%, about 40%, about 45%, about 50%, about 55%, about 60%, about 65%, about 70%, about 75%, about 80%, about 85%, about 90%, about 95%, or about 100% by mass of a compound of formula (1).

Embodiment 86

A compound of the formula:

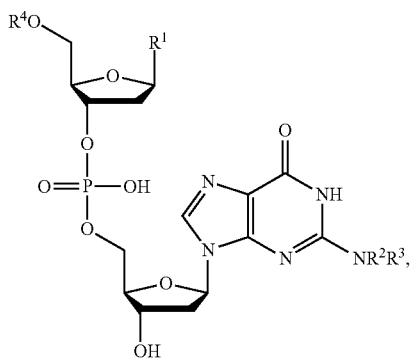

Formula (2)

or a pharmaceutically acceptable salt thereof, wherein: $R^1$ is a heteroaryl or a carbamide, each of which is independently substituted or unsubstituted; each $R^2$ and $R^3$ is independently alkyl, which is substituted or unsubstituted; or hydrogen; and $R^4$ is hydrogen or an acyl group, each of which is independently substituted or unsubstituted, wherein the compound is not a compound of Formula (1).

Embodiment 87

The compound of embodiment 86, wherein $R^1$ is a carbamide that is substituted.

Embodiment 88

The compound of embodiment 86, wherein $R^1$ is heteroaryl.

Embodiment 89

The compound of embodiments 86 or 88, wherein $R^1$ is 4-amino-2H-1$\lambda^2$,3,5-triazin-2-one.

Embodiment 90

The compound of any one of embodiments 86-89, wherein each $R^2$ and $R^3$ is substituted alkyl or hydrogen.

Embodiment 91

The compound of any one of embodiments 86-89, wherein $R^2$ is H and $R^3$ is methyl substituted with methoxy.

Embodiment 92

The compound of any one of embodiments 86-91, wherein $R^4$ is hydrogen.

Embodiment 93

The compound of any one of embodiments 86-91, wherein $R^4$ is an acyl group.

Embodiment 94

The compound of embodiment 86, wherein the compound of formula (2) is

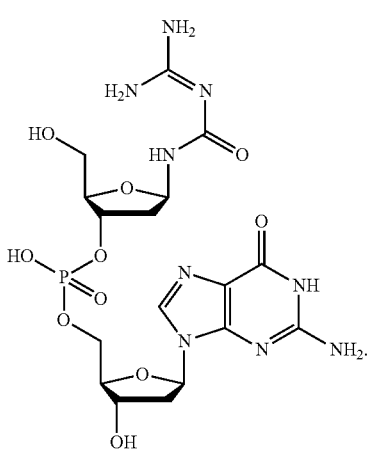

Embodiment 95

The compound of embodiment 86, wherein the compound of formula (2) is

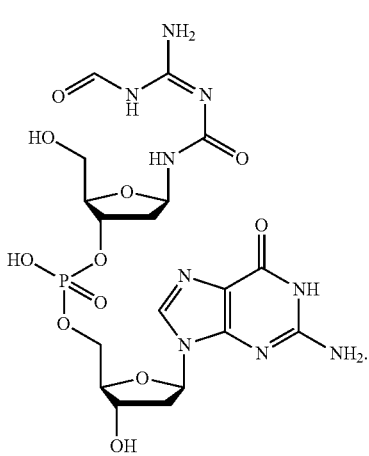

Embodiment 96

The compound of embodiment 86, wherein the compound of formula (2) is

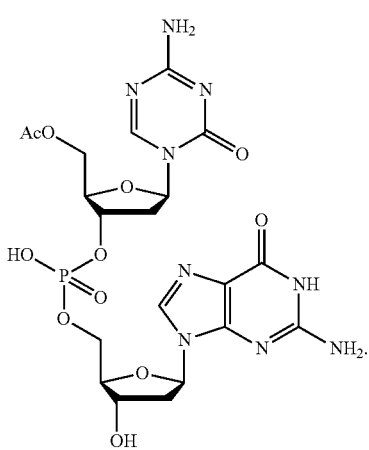

Embodiment 97

The compound of embodiment 86, wherein the compound of formula (2) is

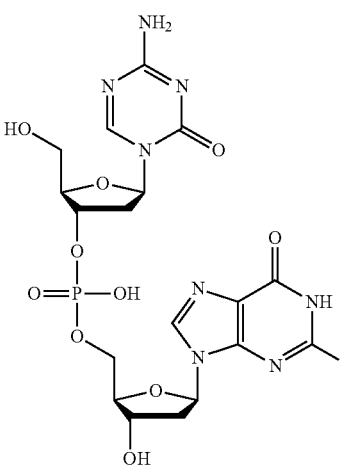

Embodiment 98

A compound of the formula:

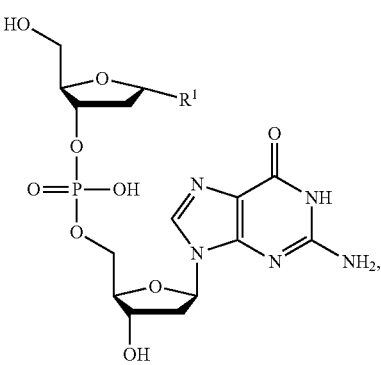

Formula (3)

or a pharmaceutically acceptable salt thereof, wherein $R^1$ is heteroaryl or a carbamide, each of which is independently substituted or unsubstituted.

Embodiment 99

The compound of embodiment 98, wherein $R^1$ is heteroaryl.

Embodiment 100

The compound of embodiment 98 or 99, wherein $R^1$ is 4-amino-2H-1$\lambda^2$,3,5-triazin-2-one.

Embodiment 101

The compound of embodiment 98, wherein $R^1$ is a carbamide that is substituted.

101

Embodiment 102

The compound of embodiment 98, wherein the compound is

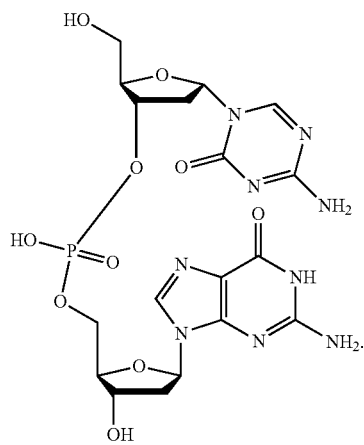

Embodiment 103

The compound of embodiment 98, wherein the compound is

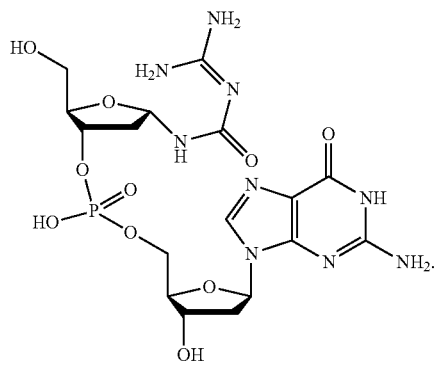

Embodiment 104

A compound of the formula:

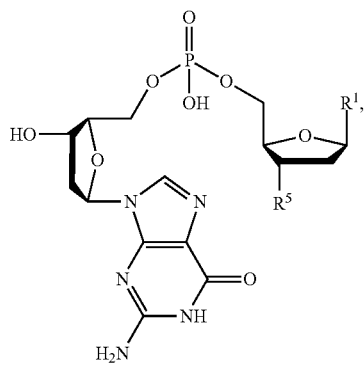

Formula (4)

102 or a pharmaceutically acceptable salt thereof, wherein $R^1$ is heteroaryl, which is substituted or unsubstituted; and $R^5$ is hydroxy or a nucleotide.

Embodiment 105

The compound of embodiment 104, wherein $R^1$ is heteroaryl that is substituted.

Embodiment 106

The compound of embodiments 104 or 105, wherein $R^1$ is 4-amino-2H-1$\lambda^2$,3,5-triazin-2-one.

Embodiment 107

The composition of embodiments 104 or 105, wherein $R^1$ is 2-amino-9$\lambda^2$-purin-6(1H)-one.

Embodiment 108

The compound of any one of embodiments 104-107, wherein $R^5$ is a hydroxyl group.

Embodiment 109

The compound of any one of embodiments 104-107, wherein $R^5$ is a nucleotide.

Embodiment 110

The compound of embodiments 104, wherein the nucleotide has the formula:

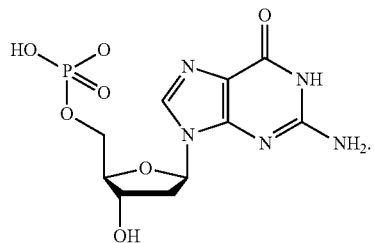

Embodiment 111

The compound of embodiment 104, wherein the compound is

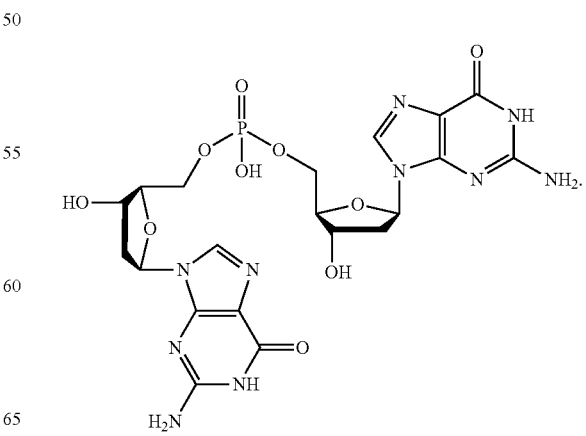

Embodiment 112

The compound of embodiment 104, wherein the compound is

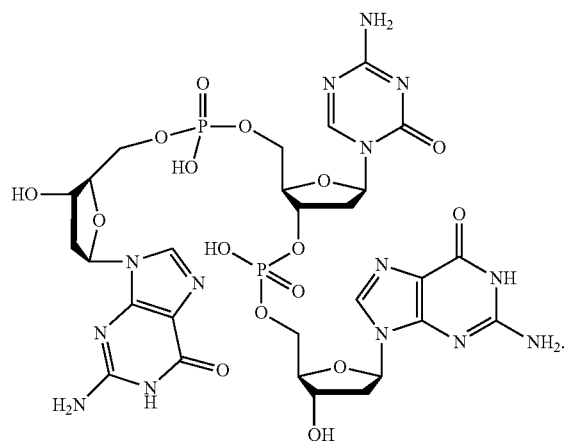

Embodiment 113

A method of treating a condition in a subject in need thereof, the method comprising administering to the subject a therapeutically-effective amount of the composition of any one of embodiments 31-58.

Embodiment 114

A method of treating a condition in a subject in need thereof, the method comprising administering to the subject a therapeutically-effective amount of the pharmaceutical composition of any one of embodiments 58a-85b.

Embodiment 115

A method of treating a condition in a subject in need thereof, the method comprising administering to the subject a therapeutically-effective amount of the compound of any one of embodiments 86-112.

Embodiment 116

The method of any one of embodiments 113-115, wherein the condition is cancer.

Embodiment 117

The method of embodiment 116, wherein the cancer is cancer of the bladder, breast, colon, kidney, epidermis, liver, lung, oesophagus, gall bladder, ovary pancrease, stomach, cervix, thyroid, prostate, gastrointestinal system, or skin.

What is claimed is:

1. A method of preparing a lyophilized pharmaceutical product, the method comprising removing a portion of a solvent by a freeze-drying process from a solution, thereby generating the lyophilized pharmaceutical product, wherein the solution comprises:

a) a compound of formula (1)

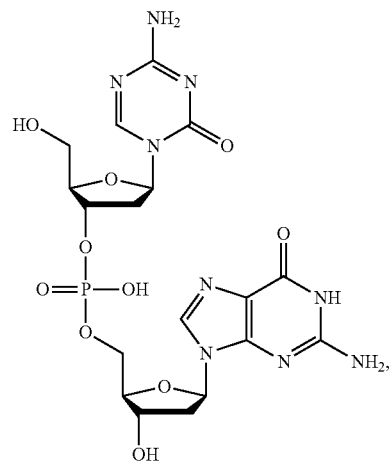

Formula (1)

or a pharmaceutically acceptable salt thereof; and b) the solvent, wherein the solvent comprises DMSO, wherein the lyophilized pharmaceutical product comprises a compound of formula (2):

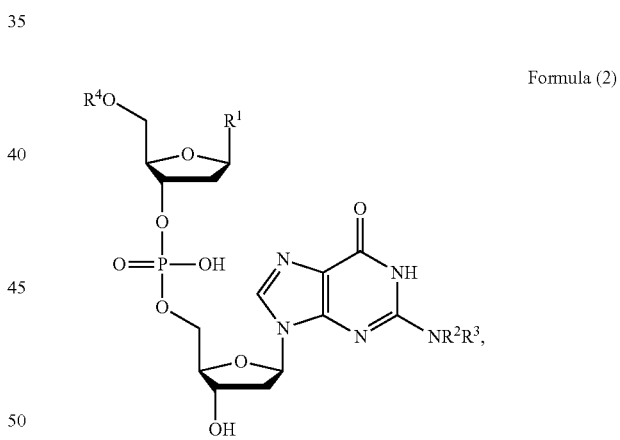

Formula (2)

or a pharmaceutically-acceptable salt thereof, wherein:

$R^1$ is a 4-amino-2H-1$\lambda^2$,3,5-triazin-2-one or a carbamide, each of which is independently substituted or unsubstituted;

each $R^2$ and $R^3$ is independently alkyl, which is substituted or unsubstituted; or hydrogen; and $R^4$ is hydrogen or an acyl group, each of which is independently substituted or unsubstituted.

2. The method of claim 1, wherein the compound of formula (2) is

3. The method of claim 1, wherein the compound of formula (2) is

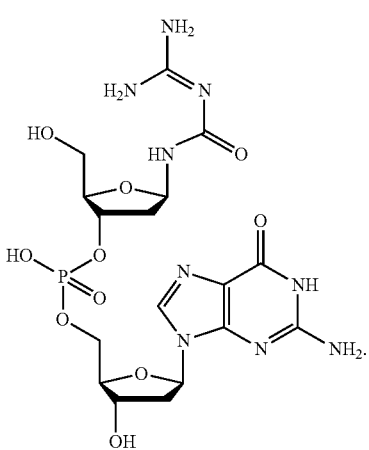

4. The method of claim 1, wherein the compound of formula (2) is

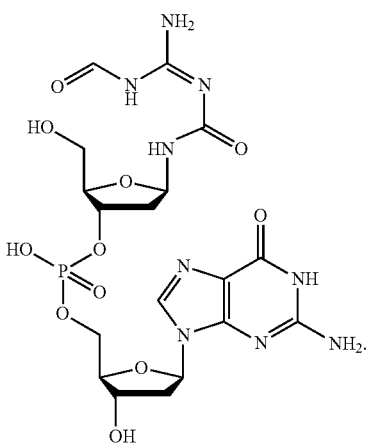

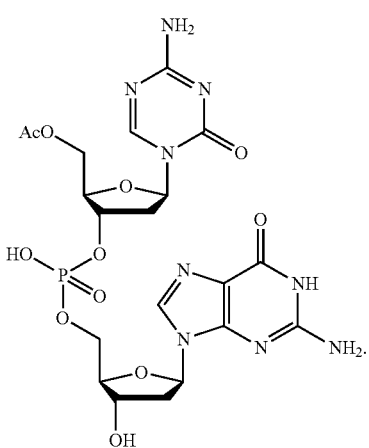

5. The method of claim 1, wherein the compound of formula (2) is

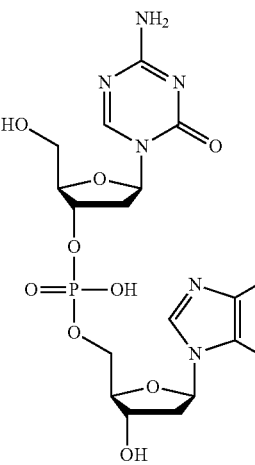

6. The method of claim 1, wherein the freeze-drying process comprises:

(a) a first freezing stage in which the solution is frozen by reducing a temperature of the solution to about −45° C. to form a frozen solution.

7. The method of claim 6, wherein the freeze-drying process further comprises:

(b) a first warming stage in which the temperature of the solution is raised from about −45° C. to about 0° C., wherein the solution remains frozen when the temperature of the solution is about 0° C.

8. The method of claim 7, wherein the freeze-drying process further comprises:

(c) a second freezing stage in which the temperature of the solution is lowered from about 0° C. to about −45° C.

9. The method of claim 8, wherein the freeze-drying process further comprises:

(d) a primary drying stage in which the temperature of the solution is raised from about −45° C. to about −6° C., wherein the primary drying stage comprises a sublimation step in which the DMSO is removed by sublimation from the solution in a frozen state of the solution under reduced pressure to give a partially dried product.

10. The method of claim 9, wherein the freeze-drying process further comprises:

(e) a secondary drying stage in which the temperature of the solution is raised from about −6° C. to about 40° C., wherein in the secondary drying stage the DMSO is removed by evaporation from the partially dried product in a non-frozen state under reduced pressure to give the lyophilized pharmaceutical product.

11. A method of preparing a lyophilized pharmaceutical product, the method comprising removing a portion of a solvent by a freeze-drying process from a solution, thereby generating the lyophilized pharmaceutical product, wherein the solution comprises:

a) a compound of formula (1)

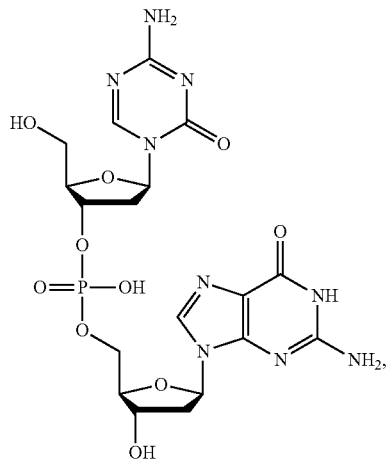

Formula (1)

or a pharmaceutically acceptable salt thereof; and
b) the solvent, wherein the solvent comprises DMSO, wherein the lyophilized pharmaceutical product comprises a compound of formula (3):

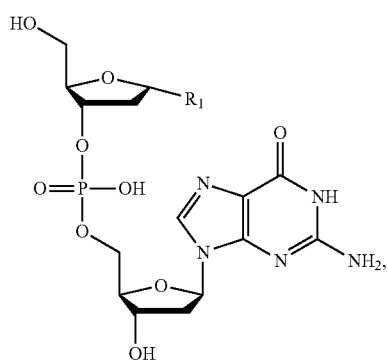

Formula (3)

or a pharmaceutically acceptable salt thereof, wherein $R^1$ is 4-amino-2H-1$\lambda^2$,3,5-triazin-2-one or a carbamide, each of which is independently substituted or unsubstituted.

12. The method of claim 11, wherein the compound of formula (3) is

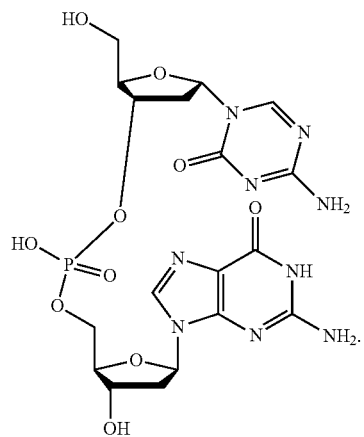

13. The method of claim 11, wherein the compound of formula (3) is

14. The method of claim 11, wherein the freeze-drying process comprises:
   (a) a first freezing stage in which the solution is frozen by reducing a temperature of the solution to about −45° C. to form a frozen solution.

15. The method of claim 14, wherein the freeze-drying process further comprises:
   (b) a first warming stage in which the temperature of the solution is raised from about −45° C. to about 0° C., wherein the solution remains frozen when the temperature of the solution is about 0° C.

16. The method of claim 15, wherein the freeze-drying process further comprises:
   (c) a second freezing stage in which the temperature of the solution is lowered from about 0° C. to about −45° C.

17. The method of claim 16, wherein the freeze-drying process further comprises:
   (d) a primary drying stage in which the temperature of the solution is raised from about −45° C. to about −6° C., wherein the primary drying stage comprises a sublimation step in which the DMSO is removed by sublimation from the solution in a frozen state of the solution under reduced pressure to give a partially dried product.

18. The method of claim 17, wherein the freeze-drying process further comprises:
   (e) a secondary drying stage in which the temperature of the solution is raised from about −6° C. to about 40° C., wherein in the secondary drying stage the DMSO is removed by evaporation from the partially dried product in a non-frozen state under reduced pressure to give the lyophilized pharmaceutical product.

19. A method of preparing a lyophilized pharmaceutical product, the method comprising removing a portion of a solvent by a freeze-drying process from a solution, thereby generating the lyophilized pharmaceutical product, wherein the solution comprises:

a) a compound of formula (1)

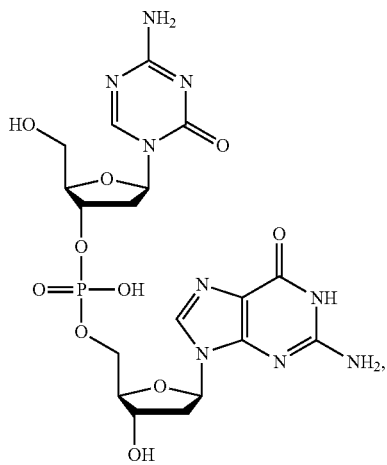

Formula (1)

or a pharmaceutically acceptable salt thereof; and b) the solvent, wherein the solvent comprises DMSO, wherein the lyophilized pharmaceutical product comprises a compound of formula (4):

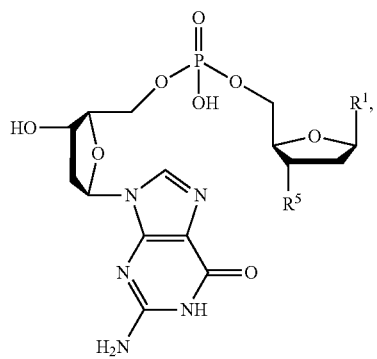

Formula (4)

or a pharmaceutically acceptable salt thereof, wherein $R^1$ is 4-amino-2H-1$\lambda^2$,3,5-triazin-2-one, which is substituted or unsubstituted; and $R^5$ is hydroxy or a nucleotide.

20. The method of claim 19, wherein the nucleotide has the formula:

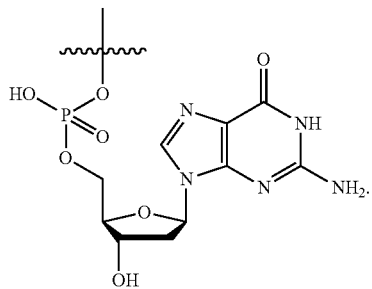

21. The method of claim 19, wherein the compound of formula (4) is

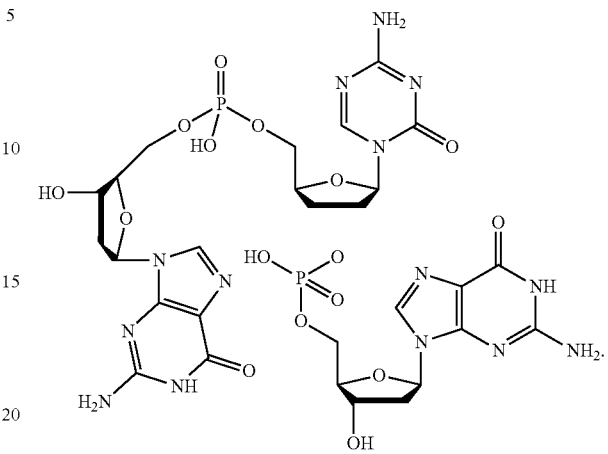

22. The method of claim 19, wherein the freeze-drying process comprises:

(a) a first freezing stage in which the solution is frozen by reducing a temperature of the solution to about −45° C. to form a frozen solution.

23. The method of claim 22, wherein the freeze-drying process further comprises:

(b) a first warming stage in which the temperature of the solution is raised from about −45° C. to about 0° C., wherein the solution remains frozen when the temperature of the solution is about 0° C.

24. The method of claim 23, wherein the freeze-drying process further comprises:

(c) a second freezing stage in which the temperature of the solution is lowered from about 0° C. to about −45° C.

25. The method of claim 24, wherein the freeze-drying process further comprises:

(d) a primary drying stage in which the temperature of the solution is raised from about −45° C. to about −6° C., wherein the primary drying stage comprises a sublimation step in which the DMSO is removed by sublimation from the solution in a frozen state of the solution under reduced pressure to give a partially dried product.

26. The method of claim 25, wherein the freeze-drying process further comprises:

(e) a secondary drying stage in which the temperature of the solution is raised from about −6° C. to about 40° C., wherein in the secondary drying stage the DMSO is removed by evaporation from the partially dried product in a non-frozen state under reduced pressure to give the lyophilized pharmaceutical product.

27. A method of preparing a lyophilized pharmaceutical product, the method comprising removing a portion of a solvent by a freeze-drying process from a solution, thereby generating the lyophilized pharmaceutical product, wherein the solution comprises:

a) a compound of formula (1):

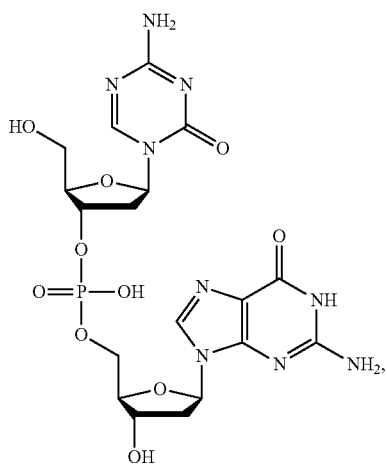

Formula (1)

or a pharmaceutically-acceptable salt thereof; and
b) the solvent, wherein the solvent comprises DMSO, wherein the freeze-drying process comprises:
(i) a first freezing stage in which the solution is frozen by reducing a temperature of the solution to about −45° C. to form a frozen solution;
(ii) a first annealing stage in which the temperature of the solution is raised from about −45° C. to about 0° C., wherein the solution remains frozen when the temperature of the solution is about 0° C.;
(iii) a second freezing stage in which the temperature of the solution is lowered from about 0° C. to about −45° C.;
(iv) a primary drying stage in which the temperature of the solution is raised from about −45° C. to about −6° C., wherein the primary drying stage comprises a sublimation step in which the DMSO is removed by sublimation from the solution in a frozen state of the solution under reduced pressure to give a partially dried product; and
(v) a secondary drying stage in which the temperature of the solution is raised from about −6° C. to about 40° C., wherein in the secondary drying stage the DMSO is removed by evaporation from the partially dried product in a non-frozen state under reduced pressure to give the lyophilized pharmaceutical product, wherein the lyophilized pharmaceutical product comprises a compound of formula (2):

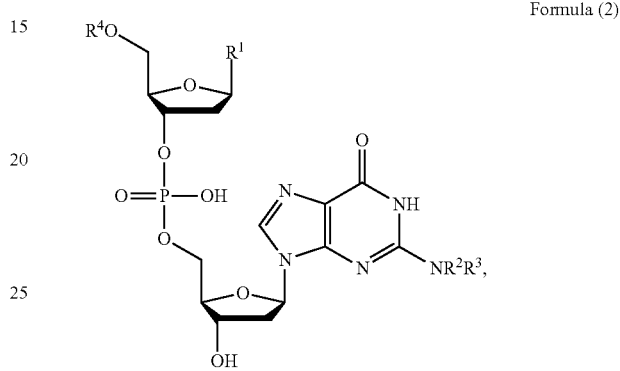

Formula (2)

or a pharmaceutically-acceptable salt thereof, wherein:
$R^1$ is 4-amino-2H-1$\lambda^2$,3,5-triazin-2-one or a carbamide, each of which is independently substituted or unsubstituted;
each $R^2$ and $R^3$ is independently alkyl, which is substituted or unsubstituted; or hydrogen; and
$R^4$ is hydrogen or an acyl group, each of which is independently substituted or unsubstituted.

\* \* \* \* \*